(12) United States Patent
Eisenbach et al.

(10) Patent No.: US 7,906,620 B2
(45) Date of Patent: Mar. 15, 2011

(54) TUMOR ASSOCIATED ANTIGEN, PEPTIDES THEREOF, AND USE OF SAME AS ANTI-TUMOR VACCINES

(75) Inventors: Lea Eisenbach, Rehovot (IL); Boaz Tirosh, Brighton, MA (US); Lior Carmon, Tel-Aviv (IL); Arthur Machlenkin, Kiryat Ekron (IL); Adrian Paz, Petach Tikva (IL); Esther Tzehoval, Nes Ziona (IL); Matityahu Fridkin, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 254 days.

(21) Appl. No.: 10/524,787

(22) PCT Filed: Jul. 28, 2003

(86) PCT No.: PCT/US03/23503
§ 371 (c)(1),
(2), (4) Date: Sep. 23, 2005

(87) PCT Pub. No.: WO2004/016643
PCT Pub. Date: Feb. 26, 2004

(65) Prior Publication Data
US 2006/0263342 A1 Nov. 23, 2006

Related U.S. Application Data

(60) Provisional application No. 60/403,657, filed on Aug. 16, 2002.

(51) Int. Cl.
*A61K 39/00* (2006.01)
*A61K 48/00* (2006.01)
*C07K 14/82* (2006.01)
*C12N 5/08* (2006.01)

(52) U.S. Cl. .................. 530/350; 424/93.21; 424/185.1; 435/366

(58) Field of Classification Search .................. 530/350; 424/93.21, 185.1; 435/366
See application file for complete search history.

(56) References Cited

U.S. PATENT DOCUMENTS

| 6,329,503 | B1 * | 12/2001 | Afar et al. | 530/350 |
| 6,833,438 | B1 * | 12/2004 | Afar et al. | 530/350 |
| 2003/0092037 | A1 * | 5/2003 | Matsuzaki et al. | 435/6 |
| 2003/0148410 | A1 * | 8/2003 | Berger et al. | 435/7.23 |
| 2004/0037840 | A1 * | 2/2004 | Beier et al. | 424/185.1 |
| 2005/0063975 | A1 * | 3/2005 | Afar et al. | 424/155.1 |

OTHER PUBLICATIONS

Sequence search alignment for SEQ ID No. 41 (pp. 1-3).*
Lazar et al Molecular and Cellular Biology Mar. 1988 vol. 8 No. 3 1247-1252).*
Schwartz et al, Proc Natl Acad Sci USA vol. 84:6408-6411 (1987).*
Lin et al Biochemistry USA vol. 14:1559-1563 (1975).*
Sequence search alignment for residues 31-426 of SEQ ID No. 58 (pp. 1-2).*
Machlenkin (Can. Res. 65:6435-6442 (2005)).*
Machlenkin (Can. Immunol. Immunother.56:217-226 (2007).*
Bar-Haim (Br. J. Can. 91:398-407 (2004).*
Carmon (Int. J. Can. 85:391-397 (2000)).*
Carmon (J. Clin. Invest. 110:453-462 (2002).*
Stepensky (Clin. Exp. Immunol. 143:139-149 (2005).*
Tirosh et al. Brit. J. Can. 97:1655-1663 (2007).*
Lesterhuis et al. (Critical Reviews in Oncology/Hematology 66:118-134 (2008).*
Trojan et al. (Lung Can. 36(2):151-158 (May 2002)).*
Abrams et al. (Cell. Immunol. 182:137-1515 (1997)).*
Tsang et al. (Can. Res. 61:7568-7576 (Oct. 15, 2001)).*
Smith et al. (Nature Biotechnology 15:1222-1223 (1997)).*
Brenner (Trends in Genetics 15:132-133 (1999)).*
Sequence search alignment for residues 31-426 of SEQ ID No. 58 (pp. 1-2), (Jul. 10, 2007).*
Sequence search alignment for SEQ ID No. 41 (pp. 1-3), (Apr. 12, 2007).*
Schirle et al. (J. Immunol. Methods. 2001; 257: 1-16).*
Anderson et al. (Tissue Antigens. Jun. 2000; 55 (6): 519-531).*
Feltkamp et al. (Mol. Immunol. Dec. 1994; 31 (18): 1391-1401).*
Burgess et al, Journal of Cell Biology vol. 111 Nov. 1990 2129-2138).*
Behr, Thomas M., "Radioimmunotherapy of Small-Volume Disease of Metastatic Colorectal Cancer: Results of a Phase II Trial with the Iodine-131-Labeled Humanized Anti-Carcinoembryonic Antigen Antibody hMN-14", Cancer (2002), vol. 94, No. 4, pp. 1373-1381.
Chames, Patrick, "Direct selection of a human antibody fragment directed against the tumor T-cell epitope HLA-A1-MAGE-A1 from a nonimmunized phage-Fab library", PNAS (2000) 97:14, pp. 7969-7974.
Fishman, Pnina et al., "Autoantibodies to Tyrosinase: The Bridge between Melanoma and Vitiligo", Cancer (1997), Vo. 79, No. 8, pp. 1461-1464.
Govorko, Dimitri et al., "Single-chain antibody against the common epitope of mutant p53: isolation and intracytosolic expression in mammalian cells", Journal of Immunological Methods (2001), vol. 258, pp. 169-181.
Huang, Sharon K.S., "Antibody Responses to Melanoma/Melanocyte Autoantigens in Melanoma Patients", (1998), vol. III, No. 4, The Journal of Investigative Dermatology, Inc., pp. 662-667.

(Continued)

*Primary Examiner* — Lynn Bristol
(74) *Attorney, Agent, or Firm* — Browdy and Neimark, PLLC

(57) ABSTRACT

The invention relates to colon and prostate tumor associated antigen peptides obtainable from prostate specific G protein-coupled receptor (PSGR), six-transmembrane epithelial antigen of prostate (STEAP) and proteins encoded by genes found overexpressed in colon carcinoma cells, such as human 1-8D interferon induced transmembrane protein 2. The invention further relates to a polynucleotide encoding the tumor associated antigen peptides and to pharmaceutical compositions, which are preferably anti-tumor vaccine compositions, containing a tumor associated antigen, at least one tumor associated antigen peptide thereof, or encoding polynucleotide thereof as an active ingredient. The pharmaceutical compositions can be administered to a patient in need thereof to treat or inhibit the development of colon or prostate cancer.

15 Claims, 18 Drawing Sheets

OTHER PUBLICATIONS

Jager, Elke et al., "Humoral Immune Responses of Cancer Patients Against Cancer-Testis" Antigen NY-ESO-1: Correlation with Clinical Events, (1999) 84, Int. J. Cancer (Pred. Oncol.), pp. 506-510.

Lev, A. et al., "Isolation and Characterization of Human Recombinant Antibodies Endowed with the Antigen-specific, Major Histocompatibility Complex-restricted Specificity of T Cells Directed toward the Widely Expressed Tumor T-cell Epitopes of the Telomerase Catalytic Subunit", (2002), Cancer Research, vol. 62, pp. 3184-3194.

Moase, E.H. et al., "Anti-MUC-1 Immunoliposomal doxorubicin in the treatment of murine models of metasttic breast cancer", (2001), Biochimica et Biohysica Acta 1510, pp. 43-55.

Niethammer, Andreas G. et al., "An oral DNA vaccine against human carcinoembryonic antigen (CEA) prevents growth and dissemination of Lewis lung carcinoma in CEA transgenic mice", (2002), Vaccine 20, pp. 421-429.

Okamoto, Tetsuro et al., "Anti-Tyrosinase-Related Protein-2 Immune Response in Vitiligo patients and Melanoma Patients Receiving Active-Specific Immunotherapy", (1998), The Journal of Investigative Dermatology, Inc., pp. 1034-1039.

Parker, Kenneth C., "Scheme for Ranking Potential HLA-A2 Binding Peptides Based on Independent Binding of Individual Peptide Side-Chains", (1994), Journal of Immunology, pp. 163-175.

Reddish, Mark A., "Anti-MUC1 Class I Restricted CTLs in Metastatic Breast Cancer Patients Immunized with a Synthetic Muc1 Peptide", (1998), vol. 76, Int. J. Cancer, pp. 817-823.

Ullenhag, Gustav J. et al., "Induction of IgG Subclass Responses in Colorectal Carcinoma Patients Vaccinated with Recombinant Carcinoembryonic Antigen", (2002), Cancer Research, vol. 62, pp. 1364-1369.

Yip, Yum L., "Anti-ErbB-2 monoclonal antibodies and ErbB-2-directed vaccines", (2002), vol. 50, Cancer Immunol Immunother, pp. 569-587.

Carmon, L et al "Novel Breast-Tumor-Associated MUC1-Derived Peptides: Characterization in Db-/-X β2 Microglobulin (β2m) Null Mice Transgenic for a Chimeric HLA-A2.1/$D^b$-β2 Microglobulin Single Chain" Int. J. Cancer 85 (2000) pp. 391-397.

Carmon, L et al Characterization of novel breast carcinoma-associated BA46-derived peptides in HLA-A2.1$D^b$-β2m transgenic mice: J. Clin. Invest. 110 (2002) pp. 453-462.

Celis, Esteban et al "Induction of anti-tumor cytotoxic T lymphocytes in normal humans using primary cultures and synthetic peptide epitopes" Proc. Natl. Acad. Sci. vol. 91, (Mar. 1984) pp. 2105-2109.

Conroy, R.M. et al "Phase I Trial of a Recombinant Vaccinia Virus Encoding Carcinoembryonic Antigen in Metastatic Adencarcinoma: Comparison of Intradermal versus Subcutaneous Administration" Clin Cancer Res. 5 (1999) pp. 2330-2337.

Deblandre, Gisele A. et al "Expression Cloning of an Interferon-inducible 17-kDa Membrane Protein Implicated in the Control of Cell Growth" The J. of Biological Chemistry vol. 270, No. 40 (Oct. 1995) pp. 23860-23866.

Firat, H et al "Comparative analysis of the $CD8^+$ T cell repertoires of H-2 class I wild-type/HLA-A2.1 and H-2 class I knockout/HLA-A2.1 transgenic mice" Int. Immunol. 14 (2002) pp. 925-934.

Fong, Lawrence, et al "Induction of Tissue-Specific Autoimmune Prostatitis with Prostatic Acid Phosphatase Immunization: Implications for Immunotherapy of Prostate Cancer" The J. of Immunology (1997) pp. 3113-3117.

Hisamatsu, Tadakazu, et al "Interferon-inducible Gene Family 1-8U Expression in Colitis associated Colon Cancer and Severely Inflamed Mucosa in Ulcerative Colitis" J. Cancer Research 59 (1999) pp. 5927-5931.

Kawakami, Yutaka et al "Recognition of Multiple Epitopes in the Human Melanoma Antigen gp100 by Tumor-Infiltrating T Lymphocytes Associated with In Vivo Tumor Regression" The J. of Immunology (1995) pp. 3961-3968.

Lewin, Andrew R. et al "Molecular Analysis of a Human interferon-inducible gene family" J. Biochem. 199 (1991) pp. 417-423.

Machlenkin, A et al "Human CTL Epitopes Prostatic Acid Phosphates-3 and Six-Transmembrane Epithelial Antigen of Prostate-3 as Candidates for Prostate Cancer Immunotherapy" Cancer Res. 65 (2005) pp. 6435-6442.

Mandelboim, Ofer et al "Regression of established murine carcinoma metastases following vaccination with tumour-associated antigen peptides" Nature Medicine, vol. 1, No. 11, (Nov. 1995) pp. 1179-1183.

Moller, P. et al "Small ISGs Coming Forward" J. Interferon Cytokine Res. 24 (2004) pp. 1-19.

Murphy, G.P. et al "Infusion of Dendritic Cells pulsed with HLA-A2-Specific Prostate-Specific Membrane Antigen Peptides: A Phasse II Prostate Cancer Vaccine Trial Involving Patients with Hormone-Refractory Metastatic Disease" Prostate 38 (1999) pp. 73-78.

Pascolo, Steve et al "HLA-A2.1-restricted Education and Cytolytic Activity of CD8+ T Lymphocytes from β2 Microglobulin (β2m) HLA-A2.1 Monochain Transgenic H-2$D^b$β2m Double Knockout Mice" J. Exp. Med. vol. 185, No. 12, (Jun. 1997) pp. 2043-2051.

Tjoa, B.A. "Follow-Up Evaluation of a Phase II Prostate Cancer Vaccine Trial" The Prostate 40 (1999) pp. 125-129.

Xu, Linda L. et al "PSGR, a Novel Prostate-specific Gene with Homology to a G Protein-coupled Receptor, is Overexpressed in Prostate Cancer" Cancer Research 60 (Dec. 2000) pp. 6568-6572.

Zhang, Lin et al "Gene Expression Profiles in Normal and Cancer Cells" Science vol. 276 (May 1997) pp. 1268-1272.

* cited by examiner

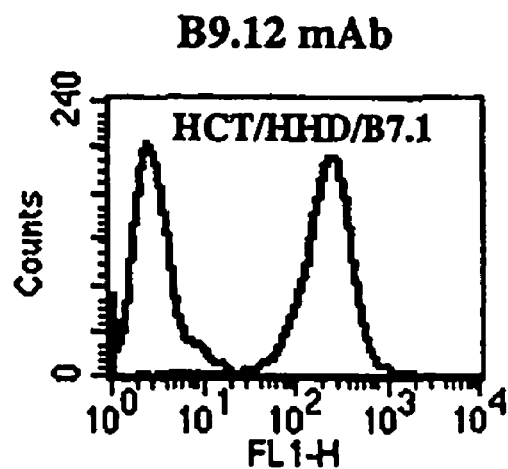
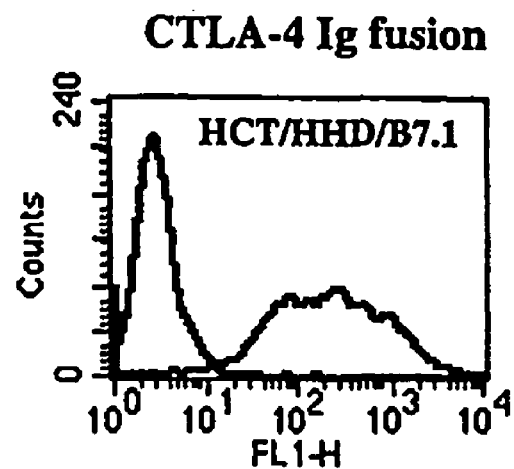
FIG.1A   FIG.1B
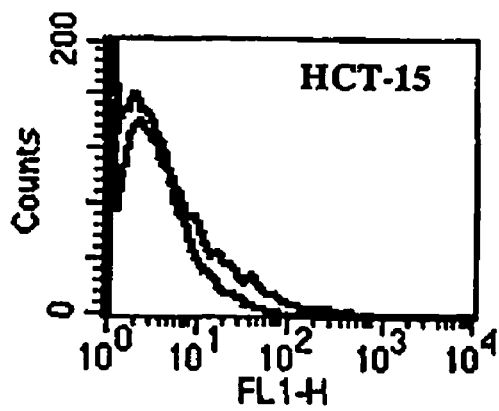
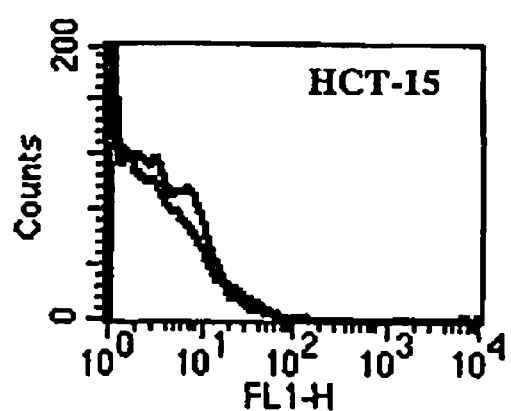
FIG.1C   FIG.1D

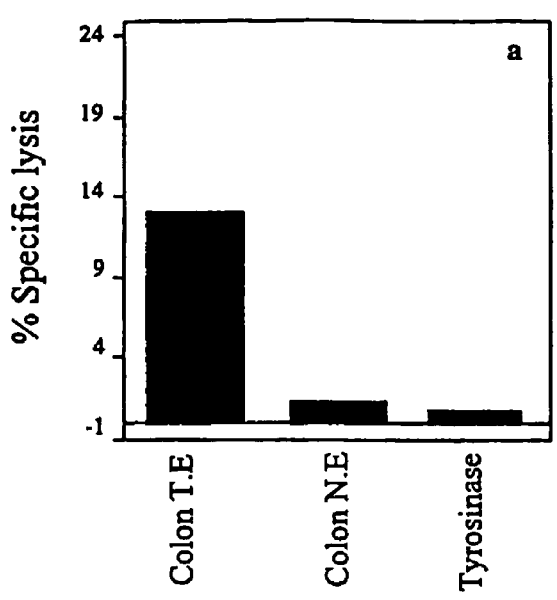
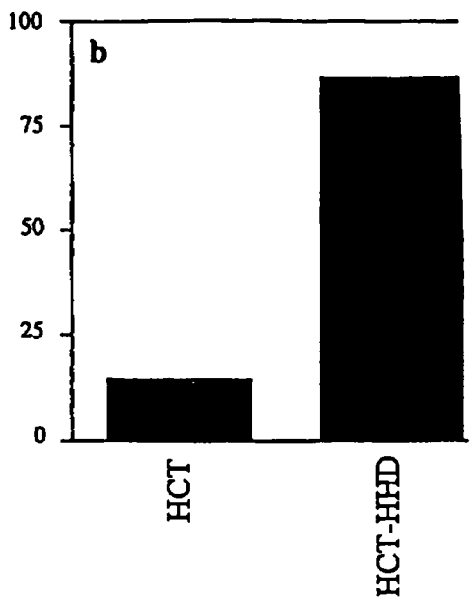
FIG. 2A  FIG. 2B
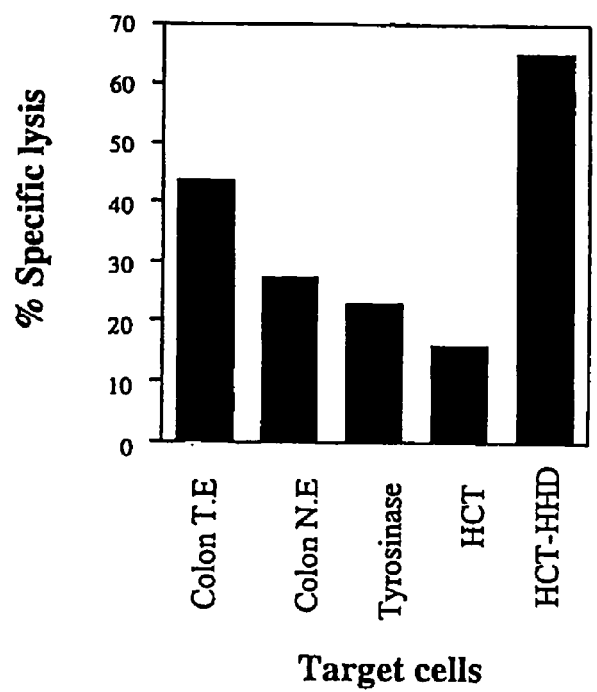
FIG. 3 a-c
1 – Marker
2 – BPH1
3 – BPH2
4 – BPH4
5 – BPH5
6 – BPH6
7 – BPH7
8 – CaP6
9 – CaP7
10 – CaP8
11 – CaP9
12 – CaP10
13 – LNCaP
14 – Du-145
15 – PC3 d-e
1 – BPH1
2 – BPH2
3 – BPH4
4 – BPH5
5 – CaP6
6 – CaP7
7 – Marker
8 – LNCaP
9 – Du-145HHD
10 – Du-145
11 – PC3
12 – T24
13 – control (no cDNA)

Positive Control

PAP-1

PSMA-1

PSA-1

PAP-2

PSMA-2

PSA-2

PAP-3

PSMA-3

STEAP-3

PSGR-3

PSGR-4

TUMOR ASSOCIATED ANTIGEN, PEPTIDES THEREOF, AND USE OF SAME AS ANTI-TUMOR VACCINES

BACKGROUND OF THE INVENTION

1. Field of the Invention

The present invention relates to tumor associated antigens (TAA) and TAA peptides, to the use thereof, to the use of polynucleotides encoding same, and to the use of cells presenting same as anti-tumor vaccines. More particularly, the present invention relates to tumor associated antigen peptides derived from prostate specific G protein-coupled receptor (PSGR), six-transmembrane epithelial antigen of prostate (STEAP) and proteins encoded by polynucleotides overexpressed in colon carcinoma cells and the use of same for diagnosis and as anti-tumor vaccines to treat or inhibit the development of colon and prostate cancers, particularly carcinomas. More particularly, the present invention relates to tumor associated antigen peptides which are presentable to the immune system by HLA-A2 molecules.

2. Description of the Related Art

Local therapy such as surgical excision or ablation by radiation is a mainstay for the treatment of primary cancer and is curative for a percentage of patients. However, many malignancies will recur locally or at a distant site. Thus the prevention or cure of metastases remains a major focus in clinical oncology (Fidler et al., 1987). Although early detection followed by surgery provides good prognosis for a number of major cancer types, a large fraction of patients would need adjuvant therapy. Part of these patients will, with time, succumb to metastasis (Abeloff, 1996; Andriole, 1997; and Nseyo et al., 1997). Alternative approaches based on gene therapy and immunotherapy have been the focus of attention in the last years. One such approach is specific active immunotherapy (SAI; Kedar et al., 1995). The objective of SAI is to stimulate a tumor specific cytotoxic T lymphocytes (CTL) immune response that is capable of eliminating residual metastatic disease and induce a state of immunity to protect the patients from recurrent disease. The underlying assumption of SAI is that tumor cells express tumor antigens which are sufficiently distinct in structure or context to induce an effective CTL response (Urban et al., 1992). Although the validity of these assumptions was questioned, a number of studies in the last decade have demonstrated the rationale of SAI. In a landmark study, van Pel and Boon have shown that tumor associated antigens (TAAs) can be isolated and defined (Van Pel et al., 1982). Importantly, ex-vivo manipulations of "non-immunogenic" animal tumor cells can be used to elicit effective immune responses which will also recognize parental "non-immunogenic" tumor cells (Pardoll, 1993). Studies employing rodent tumor models with little intrinsic immunogenicity have shown that in genetically modified tumor cells transduced to express MHC class I, cytokines such as IL-1, IL-2, IL-4, IL-6, IL-7, IL-12, γIFN or GM-CSF or costimulatory molecules such as B7-1 or B7-2 were capable of preventing or causing regression of tumors or metastases (Qin et al., 1996). Although gene modified tumor vaccine (GMTV) clinical trials with improved retroviral vectors or other transfer methodologies are currently tested, it becomes clear that GMTV using autologous tumor cells might be limited by its complexity, high cost and ineffective gene transfer methodologies (Pardoll, 1996). One alternative approach would be vaccination with tumor associated antigens (TAAs) presented in an effective way to the patient's immune system, to induce antigen specific CTL (Boon et al., 1996).

Cytotoxic T lymphocytes (CTL), directed against peptides presented by MHC class I molecules, constitute powerful effectors of the immune system against tumors or infectious agents (Townsend et al., 1989). These peptides are usually 8-10 amino acids long with 2-3 primary anchor residues that interact with the MHC class I molecules and 2-3 amino acid residues which bind to the T cell receptor (Rammensee et al., 1993). Several methods have been employed to identify CTL epitopes. If the amino acid sequence of a protein antigen is known, like in the case of viral proteins, oncogenes, suppressor genes or growth factor receptors, overlapping peptides of 8-10 amino acids in length can be synthesized and screened as CTL targets (Feltkamp et al., 1993). CTL epitopes may also be identified subsequent to the search for MHC binding motifs in known proteins (Kast et al., 1994). If the tumor antigen is not known, isolation of the TAA peptides from total acid extract or from MHC class I molecules followed by HPLC fractionation steps and Edman sequencing (Mandelboim et al., 1994) or mass spectrometry (Cox et al., 1994) provide a direct way of identifying CTL epitopes. A synthetic combinatorial library approach, in which defined amino acids in two MHC anchor positions are fixed and all other positions are subgrouped for CTL screening has led to the description of novel EL4 TAA peptide mimotopes (Blake et al., 1996).

The most fruitful method, so far, designed by T. Boon and his colleagues is the genetic approach in which cDNA expression libraries are pool transfected into COS7 cells with the appropriate HLA and screened by CTL lines. This approach led to the discovery of several human melanoma and mouse mastocytoma antigens recognized by specific CTL (Boon et al., 1994). The first report of a phase I clinical trial with the synthetic MAGE3 melanoma peptide, restricted by HLA-A1, showed regression of cutaneous, subcutaneous and lung metastases in 3/6 patients (Marchand et al., 1995). Recently, two reports of clinical trials have shown that treatment of patients with a melanoma gp100 TAA peptide together with IL-2 resulted in significant tumor regression in 13/31 (42%) patients and that vaccination with defined peptides or total peptide extracts on autologous dendritic cells (DC) resulted in complete or partial cures (Rosenberg et al., 1998 and Nestlel et al., 1998). Regression of lung carcinoma established metastases or small established tumors was demonstrated in a murine model by peptide vaccination (Mandelboim et al., 1995 and Mayordomo et al., 1995). These observations suggest that TAA peptide vaccines may constitute a reasonable therapeutic modality in advanced cancer. In studies with murine tumors, CTL are induced in vivo by immunization with irradiated tumor cells, often gene modified by MHC class I; cytokine or costimulatory molecules like B7-1 or B7-2 genes (Mandelboim et al., 1994; Blake et al., 1996 and Fearon et al., 1990). In melanomas, CTL lines were mostly induced from peripheral blood mononuclear cells (PBMC) of patients or from tumor infiltrated lymphocytes (TIL, Boon et al., 1994 and Bakker et al., 1994). Yet, most metastatic tumors are non-immunogenic tumors and it is extremely difficult to derive CTL lines or clones from TIL or patient's PBL. Moreover, in vitro propagated CTL clones do not always represent dominant anti-tumor specificities but rather sporadic clones surviving culture conditions. Lately, a number of studies have compared the CTL repertoire of viral or other defined peptides, restricted by HLA-A2.1 in human PBL from HLA-A2.1 expressing patients to CTL induced in HLA-A2.1 transgenic mice. Good concordance between human HLA-A2.1 and murine transgenic HLA-A2.1 CTL repertoire was found, confirming the potential of such transgenics in identification of human CTL epitopes (Wentworth et al., 1996). Although vaccination with defined peptides of HLA transgenic mice shows an overlapping repertoire to human CTL, vaccination of such mice with multi-epitope proteins shows that murine H-2 restricted responses are dominant and obliterate, as a rule, cytolytic responses with direct recognition of human HLA (Barra et al., 1993). Thus, by combining classical HLA class I transgenesis with selective destruction of murine H-2, it is possible to derive useful mouse strains for the study of HLA class I restricted responses.

Murine H-2 knockout mice transgenic for a single human HLA seem to be a suitable model for induction of anti-tumor CTL. Classical β2 microglobulin knockout mice ($\beta_2$m−/−) do not express H-2$K^b$ or other non-classical class I molecules, yet they express low levels of H-2$D^b$ heavy chain in the absence of $\beta_2$m. To derive fully H-2 knockout mice, Prof. F. Lemonnier (Pasteur Institute, Paris), prepared H-2$D^{b-/-}$ mice. These mice were crossed with $\beta_2 m^{-/-}$ mice and bred to derive homozygous $\beta_2 m^{-/-}$, $D^{b-/-}$ mice that do not express any H-2 class I. These mice are practically depleted of CD8$^+$ splenocytes, as well as other CD8$^+$ cells. To reconstitute in these mice expression of a stable HLA-A2.1, expression of $\beta_2$m is necessary. A construct containing a leader sequence, domains α1 and α2 of HLA-A2.1 and α3, transmembrane and cytoplasmic domains of H-2$D^b$ fused to human $\beta_2$m (HhD) was prepared. The exchange of the α3 human domain by a murine domain in HhD is thought to improve the interaction of the class I molecule with CD8 molecules of the murine CTL (Vitiello et al., 1991). This HhD construct was transfected into RMA and RMA-S cells and shown to bind HLA-A2.1 restricted peptides. The HhD construct was used to produce transgenic mice in C57BL/6 recipients and positive founder mice were bred to the $\beta_2 m^{-/-}$, $D^{b-/-}$ mice (Pascolo et al., 1997).

The β2m−/−, Db−/−, HhD−/+ heterozygous mice show reconstitution of CD8+ cells in the periphery relative to $\beta_2$m−/− Db−/− mice. Moreover, preliminary data from Prof. Lemonnier's lab showed that CTL induced in HhD mice against influenza NP are directed to the same HLA-A2 dominant epitope as in the human repertoire. Homozygous HhD mice were derived and a colony was established in the Weizmann Institute of Science, Israel.

The identification of genes encoding unique tumor associated antigens (TAAs) has facilitated the development of novel immunotherapeutic strategies in cancer patients. Clinical investigations have focused on targeting these cancer antigens for the generation of anti-tumor T-cell responses. TAA epitopes come from differentiation antigens, from embryonal reexpressed or overexpressed proteins, from mutated proteins and from viral proteins in viral-associated tumors (Eisenbach et al., 2000 and Offringa et al., 2000).

CD8$^+$ cells, which recognize MHC class I molecules bearing oligopeptides that are generated in the cell cytosol, are a major arm of the cellular immune response against viral infections, intracellular bacteria and various types of malignancies. Upon appropriate vaccination, these cytotoxic T lymphocytes (CTL) constitute powerful effectors against tumors that present on their cell surface MHC class I molecules tumor associated antigenic (TAA) peptides (Eisenbach et al., 2000)

The human tumor antigens are currently categorized according to their function or origin: (a) Cancer-Testes antigens—these antigens are expressed in tumors but not in normal tissues with the exception of the testis; (b) Differentiation antigens—these antigens originally identified for melanoma and consist of several "self" antigens of normal melanocytes, like Melan A, gp100 and others. HLA restricted peptides of these antigens are major targets for immunotherapy against melanoma; (c) Mutational antigens—point mutations in normal genes that are frequent in many kinds of tumors like mutated p53 and ras oncoproteins, were shown to generate TAA peptides, which upon proper stimulation induce strong anti-tumor CTL responses; (d) Overexpressed "self" antigens—many tumors constitutively overexpress self genes. Although strong immune reactions against this type of antigens might result in the destruction of normal tissues, experiences with peptide immunization in patients as well as numerous animal studies have not shown prominent toxicity concerns; (e) Viral antigens—in some cervical and anal malignancies, for example, proteins of HPV are expressed in tight association with tumors and, therefore, can be used as targets for the immune system (Offringa et al., 2000).

Thus far, little is known about possible natural target antigens for CTL in colo-rectal carcinoma patients. The few potential targets that were identified belong to the overexpressed genes, such as: her-2/neu, CEA and the recent Ep-CAM discovered by applying SEREX technology (Melief et al., 2000). Despite the fact that these antigens show natural CTL responses in patients, there is a strong need to expand the armory against colon carcinoma by discovering new TAAs (Nagorsen et al., 2000).

Prostate cancer (CaP) is increasingly recognized as a major health problem; it is the most frequently diagnosed cancer in the Western male population and the second leading cause of cancer related death in this population. Although locally confined disease is treatable, recurrent and metastasized CaP is essentially incurable. Androgen ablation therapy may palliate advanced disease, as long as prostate cells are androgen-responsive. However, the majority of patients inevitably progress to incurable, androgen-independent disease (Hubert et al., 1999). Current efforts are now directed towards developments of immunotherapy based strategies for the treatment of CaP.

WO 00/06723, which is applicants' own published PCT International application, discloses tumor associated antigen (TAA) peptides derived from uroplakin Ia, Ib, II and III, prostate specific antigen (PSA), prostate acid phosphatase (PAP), prostate specific membrane antigen (PSMA), BA=46 (lactadherin), mucin (MUC-1), and teratocarcinoma-derived growth factor (CRIPTO-1) and the use of these TAA peptides in an anti-tumor vaccine to prevent or cure bladder, prostate, breast or other cancers, particularly carcinomas.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

The present invention provides a tumor associated peptide of eight to ten amino acid residues which is capable of promoting effective binding to a MHC class I-type molecule to elicit a CTL response, such as to colon or prostate cancer cells. The peptide according to the present invention is derived or obtainable from a protein encoded by a polynucleotide overexpressed in human colon cancer cells, where the second residue from the N-terminus and the C-terminal residue are preferably (1) hydrophobic or hydrophilic or (2) neutral, hydrophobic or aliphatic natural or non-natural amino acid residues, or is obtainable from the prostate-restricted antigens, STEAP (six-transmembrane epithelial antigen of prostate) and PSGR (prostate specific G protein-coupled receptor), and specifically those having the amino acid sequences of SEQ ID NO:40, 48, 49, 50, 51, 52 or 53.

The present invention also provides a polynucleotide encoding the tumor associated peptide of the invention and a pharmaceutical composition, that contains at least one tumor associated peptide according to the present invention or at least one encoding polynucleotide thereof as an active ingredient.

Another aspect of the present invention is more specifically directed to a pharmaceutical composition which contains the tumor associated antigen (TAA) encoded by a human 1-8D interferon inducible gene, an at least one eight to ten residue TAA peptide thereof, a polynucleotide comprising the coding sequence of a 1-8D gene, or a polynucleotide encoding at least one 1-8D TAA peptide. When containing at least one tumor associated peptide, the pharmaceutical compositions of the present invention are preferably vaccine compositions, which may be cellular vaccine compositions.

Further aspects of the present invention are directed to a method for treating or for inhibiting the development of colon or prostate cancer by administering the pharmaceutical composition of the present invention to a patient in need thereof, to a method for treating or for inhibiting the development of colon cancer by administering an antibody specific for the TAA encoded by a human 1-8D interferon inducible gene, and to a method for determining overexpression of human 1-8D interferon induced transmembrane protein 2.

The present invention is also directed to a human 1-8D interferon induced transmembrane protein 2 which includes the amino acid sequence of SEQ ID NO:61 and to an encoding polynucleotide which includes the nucleotide sequence of SEQ ID NO:60.

BRIEF DESCRIPTION OF THE DRAWINGS

FIGS. 1A-1D are FACS analyses showing that HCT/HHD/B7.1 cells highly express HHD and B7.1. Cells were stained with B9.12 (FIGS. 1A and 1C) or CTLA-4-Ig (FIGS. 1B and 1D) fusion protein and analyzed by flow cytometry.

FIGS. 2A and 2B are graphs showing HLA-A2.1-restricted and colon associated lysis induced by the colon carcinoma HCT/HHD transfectant. Mice were immunized with HCT/HHD/B7.1 cells. Lysis of colon-derived TE, NE and non-relevant peptides (FIG. 2A) as well as the transfectant itself and the parental cell-line (FIG. 2B) were monitored by CTL assays. Tumor extract (T.E), Normal extract (N.E). The specific lysis at E:T in 50:1 ratio is shown.

FIG. 3 is a graph showing colon carcinoma associated CTL responses in patient-derived tumor extract immunized mice. Colon cell line HCT/HHD or non-relevant tyrosinase synthetic peptides as well as tumor and normal-derived peptide extract loaded on RMA-S/HHD served as targets. Tumor extract (T.E), normal extract (N.E). The E:T of 25:1 is shown.

FIG. 5D is the tyrosinase peptide as the positive control. Cells were stained with BB7.2 mAb and analyzed by FACS. The number of positive cells above control level is indicated for each of the peptides.

FIG. 11A is STEAP, FIG. 11B is PAP, FIG. 11C is PSGR, FIG. 11D is PSA and FIG. 11E is PSMA. PCR products were analyzed on 1% agarose gel by ethidium bromide staining. In FIGS. 11A-11C, the lanes are: lane 1 (Marker); lane 2 (BPH1); lane 3 (BPH2); lane 4 (BPH4); lane 5 (BPH5); lane 6 (BPH6); lane 7 (BPH7); lane 8 (CaP6); lane 9 (CaP7); lane 10 (CaP8); lane 11 (CaP9); lane 12 (CaP10); lane 13 (LNCaP); lane 14 (Du-145); lane 15 (PC3); and lane 16 (control—no cDNA). In FIGS. 1D and 1E, the lanes are: lane 1 (BPH1); lane 2 (BPH2); lane 3 (BPH4); lane 4 (BPH5); lane 5 (CaP6); lane 6 (CaP7); lane 7 (Marker); lane 8 (LN-CaP); lane 9 (Du-145HHD); lane 10 (Du-145); lane 11 (PC3); lane 12 (T24); and lane 13 (control—no cDNA).

FIG. 12A is a positive control where a tyrosinase peptide that is known as a high binding peptide is used. The lighter line in FIG. 12A and the thin lines in FIGS. 12B-12L represent the background of the second antibody binding. The darker line in FIG. 12A and the thick gray line in FIGS. 12B-12L represent MHC staining in the presence of peptide (100 mM).

In FIG. 16A, PBMC derived from CaP individual (donor A) were primed and re-stimulated with STEAP-3 pulsed DC/monocytes. Target cells: relevant (STEAP-3) and non-relevant peptide (HIV-derived, PAP-3) pulsed T2 cells. In FIG. 16B, PBMC derived from healthy individual (donor B) were primed and restimulated with PAP-3 pulsed DC/monocytes. Target cells: relevant (PAP-3) and non-relevant peptide (HIV-derived, STEAP-3) pulsed T2 cells. PBMC derived from healthy individual (donor C) were primed and restimulated with either PAP-3 (C-1; FIG. 16C) or STEAP-3 (C-2; FIG. 16D) pulsed DC/monocytes. Relevant (PAP-3 or STEAP-3) peptide pulsed and non-pulsed T2 cells were used as targets.

DETAILED DESCRIPTION OF THE INVENTION

Figure 4:
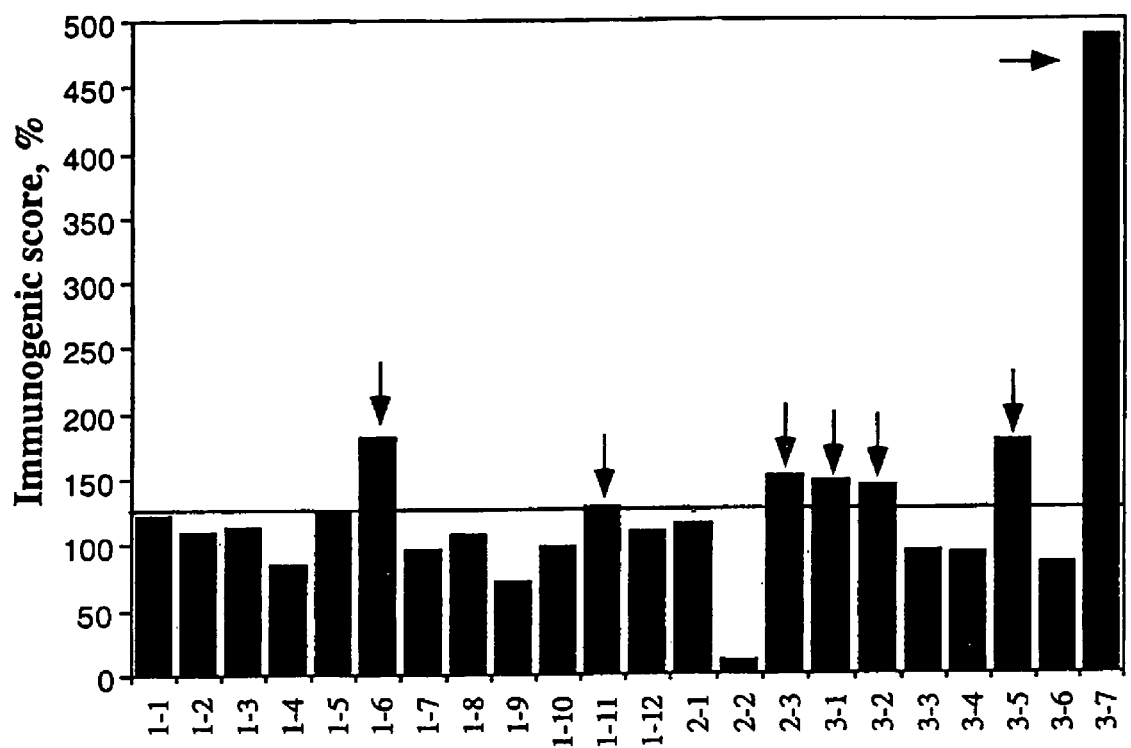
FIG. 4 is a graph of the results of in vitro cytolytic assays. Seven peptides are immunogenic. Peptides were loaded on RMA-S/HHD/B7.1, washed and irradiated. HHD mice were immunized three times as described in the materials and methods section in Example 1. In vitro cytolytic assays were performed on the relevant peptide as target and on an irrelevant peptide. The score was deduced from the ratio of the specific lysis that were obtained. The positive peptides (above 125%) are marked by arrows. Peptides 1-6, 3-5 and 3-7 are derived from "Human 1-8D gene".

The present invention concerns peptides and pharmaceutical and vaccine compositions including some which can be used to treat or to inhibit the development of cancer, both primary tumors and metastases. Specifically, the present invention provides potent tumor associated antigen (TAA) peptides derived or obtainable from prostate-specific G protein-coupled odorant receptor (PSGR), six transmembrane epithelial antigen of prostate (STEAP), and proteins encoded by polynucleotides overexpressed in colon cancer cells, which can be used in anti-tumor vaccines to treat or to inhibit the development of prostate or colon cancers, and carcinomas in particular, or any other tumor expressing the above listed proteins.

The principles and operation of the present invention may be better understood with reference to the drawings and accompanying descriptions.

Only a small number of CTL epitopes has been defined in colon cancer patients, derived mainly from her-2/neu, CEA and Ep-CAM (Melief et al., 2000 and Nagorsen et al., 2000). Since the repertoire of peptides eluted from surface MHC class I molecules is highly similar between normal colon and colon tumors (Savoie et al., 1998), the laboratory of the present inventors focused on identification of novel colon carcinoma TAAs derived from overexpressed genes. Utilizing the data of Zhang L. et al comparing transcripts of colon tumor and normal tissue samples from the same patients (Zhang et al., 1997), a set of 26 genes overexpressed at least 5 fold in tumor was obtained.

To discriminate between immunologically relevant and irrelevant MHC class I restricted peptides, $D^bX\beta2$ microglobulin (β2m) null mice transgenic for a recombinant HLA-A2.1/$D^b$-β2m single chain (HHD mice) was used by the laboratory of the present inventors. These mice combine classical HLA transgenesis with selective destruction of murine H-2. Therefore, unlike the classical HLA transgenics, these mice mount only HLA-A2.1-restricted CTL responses (lysis is HLA-A2 restricted) and were demonstrated as a useful biological tool for identifying potential TAA HLA-A2.1 restricted epitopes and to establish hierarchy in their antitumor efficacy among these peptides (Carmon et al., 2000 and Firat et al., 1999).

Over 500 putative TAA peptides were screened with anti-colon carcinoma CTL, and seven peptides were shown to be antigenic and immunogenic in HHD mice as detailed in Example 1 herein. Three of the seven peptides were derived from human 1-8D interferon induced transmembrane protein 2 (SEQ ID NO:59; accession no. BC009696) encoded by "human 1-8D interferon inducible gene (1-8D gene)" (nucleotides 31-426 of SEQ ID NO:58).and identified as peptides 1-6 (SEQ ID NO:11), 3-5 (SEQ ID NO:25), and 3-7 (SEQ ID NO:27), and were found to react both in vitro and in vivo against a colon carcinoma cell line. One of the peptides (peptide 3-7 with the amino acid sequence of SEQ ID NO:27), shared by all members of the 1-8 interferon inducible gene family, was highly immunogenic in human PBMCs. These results highlight 1-8D gene and its family as putative colon carcinoma associated antigens. The other four antigenic and immunogenic TAA peptides are identified in Table 3 in Example 1 as peptides 1-11 (SEQ ID NO:16), 2-3 (SEQ ID NO:20), 3-1 (SEQ ID NO:21), and 3-2 (SEQ ID NO:22). The laboratory of the present inventors also discovered the presence of a sequence polymorphism in 1-8D isolated from colon cancer samples (nucleotide sequence SEQ ID NO:60 and amino acid sequence SEQ ID NO:61) where when compared to SEQ ID NO:58 and 59 (accession no. BC009696 for human 1-8D interferon induced transmembrane protein 2), nucleotide 122 is a T instead of a C and changes amino acid residue 41 from Thr to Met, nucleotide 171 is a G instead of a C with no change in amino acid residue, nucleotide 234 is a G instead of a C with no change in amino acid residue, and nucleotide 362 is an A instead of a G and changes amino acid residue 121 from Val to Ile. It is intended that 1-8D nucleotide and amino acid sequences used according to the present invention for TAA peptides encompass the 1-8D nucleotide sequences of SEQ ID NOs: 58 and 60 and amino acid sequences of SEQ ID NOs: 59 and 60.

Using the HHD model, which was shown to be an effective biological tool for screening of putative novel peptides as well as for assessment of their ability to elicit powerful antitumor CTL response, prostatic acid phosphatase (PAP) derived peptide 3 (PAP-3; SEQ ID NO:46), six-transmembrane epithelial antigen of prostate (STEAP) derived peptide 3 (STEAP-3; SEQ ID NO:41) as well as PSGR derived peptides (PSGR 1-7; SEQ ID NOs: 49-55) were shown to be immunogenic in HHD mice. Importantly, testing the peripheral blood of healthy individuals has shown the existence of peripheral CTL precursors for peptide PAP-3 (2 out of 2 donors) and for peptide STEAP-3 (1 out of 2 donors) peptides. In addition, peptide STEAP-3 has activated peripheral CTL precursors in PBMC derived from CaP individual.

In accordance with another aspect of the present invention, there is provided a pharmaceutical composition, more preferably a vaccine composition, which includes at least one tumor associated antigen peptide derived or obtainable from PSGR, STEAP, or proteins encoded by polynucleotides overexpressed in colon cancer cells, which are tumor associated antigens such as the human 1-8D interferon induced transmembrane protein 2.

A further aspect of the present invention relates more particularly to a pharmaceutical composition, preferably a vaccine composition, that includes the human 1-8D interferon inducible gene, or at least one 8-10 residue TAA peptide thereof. The at least one 8-10 residue TAA peptide can specifically fit one type of HLA class I molecule, i.e., HLA-A2.1 or another HLA haplotype, or can be multiple peptides that are immunogenic in different HLA haplotypes. Thus, the human 1-8D interferon induced transmembrane protein 2 or TAA peptides thereof serve as inducer and target for cellular immunity, including CTL (CD8+ cells) and helper T cells (CD4+ cells). It is well recognized in the art that many tumor associated antigens (TAAs) from which peptides were defined for one type of HLA class I molecule, i.e., HLA-A2.1, can be shown to have immunogenic peptides that bind to other types of HLA class I molecules. Table 1 below presents a representative list of tumor associated antigens with TAA peptides that bind to different types of HLA class I molecules.

TABLE 1

| TAA-Tyrosinase (melanoma) | | |
|---|---|---|
| HLA-A0201 (HLA-A2.1) | peptides in positions 351-359 and 1-9 | Wolfel et al., 1994<br>Robbins et al., 1994<br>Brichard et al., 1993<br>Kast et al., 1991<br>Skipper et al., 1996 |
| HLA-A1 | Peptides 225-233 and 146-156 | Kittlesen et al., 1998<br>Kawakami et al., 1998 |
| HLA-A24 | Peptide 188-197 | Kang et al., 1995 |
| HLA-B4402, HLA-B4403 | Peptide 192-200 | Brichard et al., 1996 |
| TAA-MUC1 (carcinomas) | | |
| HLA-A0201 | peptides 130-138, 141-148, 12-20, 950-958, 32-40, 412-421, 226-234 | Postolopoulos et al., 1997<br>Brossart et a., 1999<br>Carmon et al., 2000 |
| HLA-A1101 | Peptide 107-115 | Domenech et al., 1995 |
| TAA-P53 (various tumors) | | |
| HLA-A0201 | peptides 322-330, 187-197, 261-269, 149-157 | Schirle et al., 2000<br>Theobald et al., 1997<br>Yu et al., 1997 |

TABLE 1-continued

| | | |
|---|---|---|
| HLA-A1101 | Peptide 343-351 | Yu et al., 1997 |
| HLA-B1502 | Peptide 274-281 | Barber et al., 1997 |
| HLA-B2709 | Peptide 266-274 | Fiorillo et al., 1997 |
| | TAA-CEA (carcinomas) | |
| HLA0201 | peptides 694-702, 691-699 | Schirle et al., 2000 |
| | | Tsang et al., 1995 |
| | | Kawashima et al., 1998 |
| HLA-A0301 | Peptide 61-69 | Kawashima et al., 1999 |
| HLA-A24 | Peptide 268-277 | Nukaya et al., 1999 |
| HLA-A2402 | Peptide 652-660 | Kim et al., 1998 |
| | TAA-pmel17/gp100 (melanomas) | |
| HHLA-A0201 | peptides 280-288, 457-466, 209-217, 154-162, 208-217, 476-485, 619-627, 639-647, 178-186, 177-186, 570-579 | Kawakami et al., 1998 |
| | | Cox et al., 1994 |
| | | Kawakami et al., 1995 |
| | | Tsai et al., 1997 |
| HLA-A1101 | Peptide 87-95 | Kawashima et al., 1998 |
| HLA-A3 | peptides 17-25, 614-622, 87-95, 86-95 | Skipper et al., 1996 |
| HLA-Cw8 | peptides 70-78, 71-78 | Castelli et al., 1999 |
| | TAA-Melan A/Mart-1 (melanomas) | |
| HLA-A0201 | peptides 27-35, 32-40, 25-34 | Coulie et al., 1994 |
| | | Kawakami et al., 1994 |
| | | Kawakami et al., 1994 |
| | | Rivoltini et al., 1995 |
| | | Castelli et al., 1995 |
| HLA-A0202 | Peptide 27-35 | Fleishchhauer et al., 1996 |
| HLA-A0204 | Peptide 27-35 | Fleishchhauer et al., 1996 |
| HLA-A0205 | Peptide 27-35 | Fleishchhauer et al., 1996 |
| HLA-A0206 | Peptide 27-35 | Fleishchhauer et al., 1996 |
| HLA-A0209 | Peptide 27-35 | Fleishchhauer et al., 1996 |
| HLA-A6901 | Peptide 27-35 | Fleishchhauer et al., 1996 |
| HLA-B4501 | peptides 24-33, 24-34 | Schneider et al., 1998 |
| | TAA-HER-2/neu (various tumors) | |
| HLA-A0201 | peptides 348-356, 950-958, 830-838, 633-641, 752-761, 789-797, 689-697, 665-673, 435-443, 952-961, 5-13 | Kawashima et al., 1998 |
| | | Fisk et al., 1995 |
| | | Fisk et al., 1997 |
| | | Peiper et al., 1997 |
| | | Lustgarten et al., 1997 |
| | | Kono et al., 1998 |
| | | Rongcun et al., 1999 |
| HLA-A0301 | Peptide 754-762 | Kawashima et al., 1999 |
| | TAA-MAGE-1 (various tumors) | |
| HLA-A0201 | Peptide 278-286 | Pascolo et al., 2001 |
| HLA-A1 | Peptide 161-169 | Traversari et al., 1992 |
| HLA-A24 | Peptide 135-143 | Fujie et a., 1999 |
| HLA-A28 | Peptide 222-231 | Chaux et a., 1999 |
| HLA-A3 | Peptide 96-104 | Chaux et al., 1999 |
| HLA-B07 | Peptide 289-297 | Luiten et al., 2000 |
| HLA-B3501 | Peptide 161-169 | Luiten et al., 2000 |
| HLA-B53 | Peptide 258-266 | Chaux et al., 1999 |
| HLA-Cw1601 | Peptide 230-238 | Engelhard et al., 1994 |
| HLA-Cw2 | Peptide 62-70 | Chaux et al., 1999 |
| HLA-Cw3 | Peptide 230-238 | Chaux et al., 1999 |
| | TAA-MAGE-3 (various tumors) | |
| HLA-A0201 | peptides 271-279, 112-120 | Kawashima et al., 1998 |
| | | van der Bruggen et al., 1994 |
| HLA-A0207 | Peptide 271-279 | Fleischhauer et al., 1997 |
| HLA-A0209 | Peptide 271-279 | Fleischhauer et al., 1997 |
| HLA-A1 | Peptide 168-176 | Celis et a., 1994 |
| | | Gaugler et al., 1994 |
| HLA-A24 | Peptide 195-203 | Tanaka et al., 1997 |
| HLA-A2402 | Peptide 97-105 | Oiso et al., 1999 |
| HLA-B3501 | Peptide 168-176 | Schultz et al., 2001 |
| HLA-B4402 | Peptide 167-176 | Herman et al., 1996 |
| HLA-B4403 | Peptide 167-176 | Herman et al., 1996 |

TABLE 1-continued

| TAA-NY-ESO-1 (various tumors) | | |
|---|---|---|
| HLA-A0201 | peptide 157-167, 157-165, 155-163 | Jager et al., 1998 |
| | TAA-TRP-2 (melanomas) | |
| HLA-A0201 | peptides 157-165, 360-368, 288-296 | Parkhurst et al., 1998 |
| | | Noppen et al., 2000 |
| | | Sun et al., 2000 |
| HLA-Cw8 | peptide 387-395 | Castelli et al., 1999 |

While it may be preferred that, in the pharmaceutical composition according to the present invention, the at least one TAA peptide of human 1-8D interferon induced transmembrane protein 2 binds to the same HLA class I molecule as is present in a patient to which the pharmaceutical composition is to be administered (as can be readily determined, i.e., by HLA tissue typing beforehand, in order to tailor the TAA peptide or peptides to the individual patient), a pharmaceutical composition containing a mixture of TAA peptides that can bind to different types of HLA class I molecules may be alternatively used. For instance, a combination of about 5-6 peptides, each of which binds to a different HLA haplotype (i.e., a total of about 5-6 different HLA haplotypes) would cover about 95% of the world population.

Furthermore, many tumor associated antigens that induce cellular immunity can also induce humoral immunity, i.e., antibodies. Representative examples of TAAs reported to induce CTL and antibodies are tyrosinase (Fishman et al., 1997), MUC1 (Moase et al., 2001; Reddish et al., 1998), p53 (Govorko et al., 2001), CEA (Neithammer et al., 2002; Behr et al., 2002 Ullenhag et al., 2002), pmel/gp100 (Huang et al., 1998), ErbB-2 (Yum et al., 2002), MAGE-A1 (Chames et al., 2000), NY-ESO-1 (Jager et al., 1999), and TRP-2 (Okamoto et al., 1998). Accordingly, the pharmaceutical composition of the present invention that includes human 1-8D interferon induced transmembrane protein 2 can be used as a vaccine composition not only to induce cellular immunity but also to induce humoral immunity. Antibodies induced by a TAA (i.e., 1-8D) bind to tumors where the TAA is a cell surface molecule and the killing of tumor cells occurs by a number of mechanisms.

According to another aspect of the present invention, there is provided a method of vaccination for treating or inhibiting the development of colon or prostate cancer. The method is effected by administering to a patient in need thereof a vaccine composition containing at least one tumor associated antigen peptide derived or obtainable from STEAP, PSGR, or a protein encoded by a polynucleotide overexpressed in human colon cancer cells. In the case of 1-8D, the entire protein as a tumor associated antigen or at least one antigenic fragment thereof, such as a TAA peptide, may be administered according to the method of the present invention.

Immunotherapy by in vivo DNA transfer of DNA coding for TAA is based on the rationale of quality or quantity increased peptide presentation leading to activation of an immune response against these peptides. Gene or DNA vaccination results in the intracellular processing and presentation of immunogenic peptides (Spooner et al., 1995). Initial reports on DNA vaccination showed that "naked" DNA injected into the muscle tissue of a mouse is expressed efficiently (Ulmer et al., 1993). Embryonically expressed TAA such as CEA was tested (Conry et al., 1994). Immunization of mice with CEA expressing plasmid DNA was indeed found to protect 100% of these mice against a challenge with CEA-expressing colon carcinoma cells (Conry et al., 1995). Both cellular and humoral responses have been reported after DNA vaccination in mice. In other studies, a MUC-1 tandem repeat array was used for DNA vaccination of mice and 30% of these mice were protected from a tumor challenge with MUC-1 transfected murine tumor cells (Acres et al., 1993). DNA vaccination may also be used to elicit immune responses against predefined peptide epitopes. Several groups now exploit the string-bead approach to link multiple different CTL or helper epitopes together on the DNA level (Whitton et al., 1993). In some cases the string-bead of peptide coding DNA is built into a vaccinia virus as a delivery vehicle. Recently, it was shown that such a vaccinia virus recombinant poly-epitope vaccine was able to protect mice against several virus infections and a tumor challenge (Thomson et al., 1996). The authors showed that all 10 minimal peptide epitopes encoded by the string-bead are expressed and recognized by the appropriate T cell clones (Thomson et al., 1998). RNA was also shown to confer anti-tumor immunity. Vaccination with RNA to ovalbumin induced CTL in mice (Boxzkowski et al., 1996). In conclusion, multiple studies have shown the efficacy of DNA vaccines in anti-viral and anti-tumor immunity.

Thus, according to yet another aspect of the present invention, there is provided a DNA vaccine composition which includes at least one polynucleotide encoding a tumor associated antigen, such as 1-8D, or a tumor associated antigen peptide of the present invention. The at least one polynucleotide can be a part of a longer polynucleotide designed to encode a fused protein product from which the tumor associated antigen peptide is cleavable by a protease.

The polynucleotide is preferably DNA in a form of, or contained in, for example, naked DNA, plasmid, retroviral vector, adenoviral vector, vaccinia viral vector, herpes viral vector, lenti virus vector, EBV vector, CMV vector, polio virus vector, sindbis viral vector, semliki forest virus vector, parvo virus vector, adeno-associated virus vector, virus like particle (VLP) vector. Alternatively, the polynucleotide can be in the form of RNA. Aside from delivery by a vector, the polynucleotide can also be delivered in a non-viral and non-plasmid delivery system, such as, for example, but not limited to, in liposomes, in complex with cationic reagents, or with a polycation, such as poly-lysine. The polynucleotide can also be delivered by mechanical means, such as, but not limited to, a gene-gun, by electrical means, or in bacterial vectors like BCG. Such methods are described in many standard laboratory manuals.

When a vector is used, the vector may be, for example, a phage, plasmid, viral or retroviral vector. Retroviral vectors may be replication competent or replication defective. In the latter case, viral propagation generally will occur only in complementing host cells.

The polynucleotide may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

Preferred vectors carry cis-acting control regions that direct expression of the polynucleotide encoded TAA or TAA peptides. Appropriate trans-acting factors may be supplied by the host, supplied by a complementing vector or supplied by the vector itself upon introduction into the host. Expression vectors useful in the present invention include chromosomal-, episomal- and virus-derived vectors as are well known in the art.

The DNA insert should be operatively linked to an appropriate promoter, such as the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will include a translation initiating AUG at the beginning and a termination codon appropriately positioned at the end of the polypeptide to be translated.

Transcription of the DNA encoding the TAA or TAA peptides may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers.

There is increasing evidence that peptide vaccination may be much more effective when the peptides are introduced together with an antigen presenting cell (APC) (Mayordomo et al., 1995). In previous studies of a murine lung carcinoma, the laboratory of the present inventors have shown that vaccination with a defined TAA peptide (MUT-1) loaded on APC result in long term survival of mice bearing lung metastases (Mandelboim et al., 1994 and 1995). The most common cells used to load antigens are bone marrow and peripheral blood derived dendritic cells (DC), as these cells express costimulatory molecules that help with activation of CTL. Preliminary clinical trials have been performed. In one trial, HLA-A1 melanoma patients have been treated with autologous DC loaded with a MAGE-1 peptide. CTL activity was increased in tumor infiltrated lymphocytes (Mukherji et al., 1995). In another study, five patients with advanced pancreatic carcinoma were treated with a K-ras derived peptide loaded on DC. As a mutation of K-ras at codon 12 is frequently found in pancreatic carcinoma, three differently mutated peptides, 12-Asp, 12-Arg and 12-Val (non-mutated sequence is 12-Gly) were used for vaccination, matched to the mutation in the patient's tumor. Two of the patients showed a specific CTL response and prolonged survival (Gjertsen et al., 1996). A phase I clinical trial in 51 prostate cancer patients compared a soluble peptide, derived from PSMA, to a DC based peptide in HLA-A2 patients. Only 7 patients that received DC based vaccines with this peptide responded by decreased levels of serum PSA (Murphy et al., 1996). In animal studies, a number of groups showed that macrophages loaded with peptides constitute efficient vaccines, yet the number of cells used for vaccination is 10 fold higher than equivalent DC vaccines. Recently, in a murine lung carcinoma model, the efficacy of syngeneic fibroblasts treated with a proteasome inhibitor to decrease levels of endogenous peptides and loaded with synthetic MUT peptides as vaccines was tested. Effective protection was found against metastatic spread of lung carcinoma.

Thus, the present invention is further directed to a cellular vaccine composition which contains an antigen presenting cell presenting at least one tumor associated antigen peptide. The antigen presenting cell can, for example, be a dendritic cell, a macrophage, a B cell and a fibroblast. Presenting the at least one tumor associated antigen peptide of the present invention can be effected by a method selected from the group consisting of (a) transducing the antigen presenting cell with at least one polynucleotide (e.g., DNA) encoding the at least one tumor associated antigen peptide; (b) loading the antigen presenting cell with at least one polynucleotide (e.g., RNA) encoding the at least one tumor associated antigen peptide; (c) loading the antigen presenting cell with the at least one tumor associated antigen peptide (e.g., synthetic); and (d) loading the antigen presenting cell with at least one polypeptide (e.g., purified) that includes the at least one tumor associated antigen peptide. Loading can be external or internal. The polynucleotide, peptide or polypeptide can be fused to internalizing sequences, antennapedia sequences or toxoid sequences or to helper sequences, such as, but not limited to, heat shock protein sequences.

While it is clear that CD8+ class-I restricted CTL recognize and destroy tumor cells in vitro and in vivo, animal models often show a requirement of CD4+ MHC-class-II restricted T cell help for optimal responses (Ciccodicola et al., 1987). Helper T cell epitopes can contribute to induction of cellular immune responses by class I peptide vaccines, as seen by the synergistic tumor protection upon simultaneous vaccination with T helper and CTL epitopes (Qi et al., 1994). The "help" to CTL is most often provided via the production of specific cytokines. Helper epitopes can be specific and derived from a tumor antigen (Kuniyasu et al., 1991). They can also broadly crossreact with a number of MHC class II molecules, and may be either pathogen-derived or comprised of sequences not found in nature (Saeki et al., 1992; Freiss et al., 1994; and Byrne et al., 1998). More specifically, a sequence containing a T helper epitope can be linked to a CTL epitope to create one immunogenic entity. Alternatively, a mixture of two or more separate entities, corresponding to CTL and T helper epitopes can be administered to elicit the desired CTL response. T helper epitopes can also be conjugated to other molecules or compounds which increase their biological activity.

As used herein, the term "tumor associated antigen" also refers to tumor specific antigen and the term "peptide" refers to native peptides (either degradation products or synthetically synthesized peptides) and further to peptidomimetics, such as peptoids and semipeptoids which are peptide analogs, which may have, for example, modifications rendering the peptides more stable while in a body, or more immunogenic. Such modifications include, but are not limited to, cyclization, N terminus modification, C terminus modification, peptide bond modification, including, but not limited to, $CH_2$—NH, $CH_2$—S, $CH_2$—S=O, O=C—NH, $CH_2$—O, $CH_2$—$CH_2$, S=C—NH, CH=CH or CF=CH, backbone modification and residue modification. Methods for preparing peptidomimetic compounds are well known in the art and are specified in Quantitative Drug Design, C. A. Ramsden Gd., Chapter 17.2, F. Choplin Pergamon Press (1992), which is incorporated by reference as if fully set forth herein.

Also as used herein, the term "amino acid" is understood to include the 20 naturally occurring amino acids; those amino acids often modified post-translationally in vivo, including for example hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

The tumor associated antigen peptides of the present invention can be of 8, 9 or 10 amino acid residues in length with peptides of 9 or 10 amino acid residues in length desirable, more preferably 9 residues in length. Thus, the following positions (P1-P9) are represented in a 9-mer peptide:

P1-P2-P3-P4-P5-P6-P7-P8-P9

The P2 and P9 positions include the anchor residues which are the main residues participating in binding to MHC class 1 molecules, more specifically HLA-A2. Amino acid residues engaging positions P2 and P9 in HLA-A2.1 and some other haplotypes, but not in all haplotypes, are hydrophobic or hydrophilic natural amino acids or non-natural amino acids. The discussion below is directed with particular reference to the HLA-A2.1 haplotype. Examples of hydrophobic or hydrophilic natural amino acids being Ala, Cys, Gln, Glu, Ile, Leu, Met, Ser, Thr and Val. These residues may preferably be neutral, hydrophobic, aliphatic and more preferably Val, Leu and Ile. Examples of non-natural amino acids being norleucine (Nle), norvaline (Nva), aminobutyric acid preferably α-aminobuytric acid. These residues may preferably be non-charged and more preferably aliphatic. P9 can also be an aliphatic amino acid of the general formula —HN(CH$_2$)$_n$COOH, wherein n=2-5, as well as by branched derivatives thereof, such as, but not limited to,

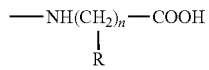

wherein R is, for example, methyl, ethyl or propyl, located at any one or more of the n carbons.

Positions P1 and P3 are also known to include amino acid residues which participate or assist in binding to MHC molecules, however, these positions can include any amino acids, natural or non-natural.

The N-terminal residue (position P1) can also be positively charged aliphatic carboxylic acids, such as, but not limited to, H$_2$N(CH$_2$)$_n$COOH, wherein n=2-5 and H$_2$N—C(=NH)—NH(CH$_2$)$_n$COOH, wherein n=2-4, hydroxy Lysine, N$^\epsilon$-methyl lysine, N$^\epsilon$-ethyl lysine, N$^\epsilon$-propyl lysine or ornithine (Orn). Additionally, the N-terminal residue can be aromatic residues, such as, but not limited to, phenyl glycine, p-aminophenyl alanine, p-guanidinophenyl alanine or pyridinoalanine (Pal). These latter residues may form hydrogen bonding with the OH-moieties of the tyrosine residues at the MHC-1 N-terminal binding pocket, as well as to create, at the same time aromatic-aromatic interactions.

The other positions P4-P8 are engaged by amino acid residues which typically do not participate in binding to MHC molecules, rather these amino acids are presented to the immune cells. Further details relating to the binding of peptides to MHC molecules can be found in Parker et al. (1994). See Table V thereof, in particular.

Amino acid residue engaging positions P4-P8 can include any natural or non-natural amino acid residues. These residues may optionally be phosphorylated and/or glycosylated. Indeed residues which have been phosphorylated or glycosylated have been shown in some cases to enhance the binding to the T cell receptor.

Cyclization can engage positions P4-P8, preferably positions P6 and P7. Cyclization can be obtained through amide bond formation, e.g., by incorporating Glu, Asp, Lys, Orn, di-amino butyric (Dab) acid, di-aminopropionic (Dap) acid at various positions in the chain (—CO—NH or —NH—CO bonds). Backbone to backbone cyclization can also be obtained through incorporation of modified amino acids of the formulas H—N((CH$_2$)$_n$—COOH)—C(R)H—COOH or H—N((CH$_2$)$_n$—NH$_2$)—C(R)H—COOH, wherein n=1-4, and further wherein R is any natural or non-natural side chain of an amino acid.

Cyclization via formation of S—S bonds through incorporation of two Cys residues is also possible. Additional side-chain to side chain cyclization can be obtained via formation of an interaction bond of the formula

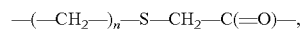

wherein n=1 or 2, which is possible, for example, through incorporation of Cys or homocys and reaction of its free SH group with, e.g., bromoacetylated Lys, Orn, Dab or Dap.

In longer peptides, such as in a 10 mer peptide in which the second anchor amino acid is at position P10, the amino acid engaging P9 may include most L-amino acids. In some cases, shorter peptides, such as 8 mer peptides, are also applicable, in which the C-terminal acid P8 may serve as the second anchor residue. All the options described for the anchor amino acid residues engaging positions P2 and P9 in a 9 mer peptide may apply likewise to the anchor amino acid residues engaging positions P2 and P10 in a 10 mer peptide and P2 and P8 in an 8 mer peptide.

The amino acids may be modified as is necessary to provide certain characteristics such as greater immunogenicity, more stability or improved pharmacological properties. The peptides can be for instance subject to changes such as the replacement of one or more amino acid residues whether dissimilar or similar.

Modification of the peptides may also be by decreasing, e.g., in a 10 mer peptide, or extending, e.g. in an 8 mer peptide, the amino acid sequence, for example, by deletion or addition of amino acids. It will be appreciated that preferably anchor amino acids should not be deleted.

Peptide bonds (—CO—NH—) within the peptide may be replaced by N-alkylated bonds such as N-methylated (—N(CH$_3$)—CO—), ester bonds (—C(R)H—C—O—O—CH(R)—N—), ketomethylene bonds (—CO—CH$_2$—), α-aza bonds (—NH—N(R)—CO—), wherein R is hydrogen or any alkyl, e.g., methyl carba bonds (—CH$_2$—NH—), hydroxyethylene bonds (—CH(OH)—CH$_2$—), thioamide bonds (—CS—NH—), olefinic double bonds (—CH=CH—), retro amide bonds (—NH—CO—), and peptide derivatives (—N(R)—CH$_2$—CO—), naturally presented on the carbon atom.

These modifications can occur at any of the bonds along the peptide chain and even at several (2-3) at the same time. Preferably, but not in all cases necessary, these modifications should exclude anchor amino acids.

For amino acid residue engaging positions other than the second residue from the N-terminus and the end residue at the C-terminus, natural aromatic amino acids, Trp, Tyr and Phe, may be replaced by synthetic non-natural amino acid such as TIC, naphthylalanine (Nal), ring-methylated derivatives of Phe, halogenated derivatives of Phe or o-methyl-Tyr.

As used herein, the term "transduced" refers to the result of a process of inserting nucleic acids into cells. The insertion may, for example, be effected by transformation, viral infection, injection, transfection, gene bombardment, electroporation or any other means effective in introducing nucleic acids into cells. Following transduction the nucleic acid is either integrated in all or part, to the cell's genome (DNA), or remains external to the cell's genome, thereby providing stably transduced or transiently transduced cells.

As used herein, phrase "derived from a protein" refers to peptides derived from the specified protein or proteins and further to homologous peptides derived from equivalent regions of proteins homologous to the specified proteins of the same or other species, provided that these peptides are effective as anti-tumor vaccines. The term further relates to permissible amino acid alterations and peptidomimetics designed based on the amino acid sequence of the specified proteins or their homologous proteins.

The term "anti-tumor vaccines" refers to vaccines effective in treating or inhibiting the development of cancer, including primary tumor and/or metastases, which include inhibiting, slowing or reversing the progression of a disease, substantially ameliorating clinical symptoms of a disease or substantially preventing the appearance of clinical symptoms of a disease.

The phrase as used herein "loading" refers to exposing, adding or introducing a substance into or onto a cell or vesicle or part thereof as is well known to those of skill in the art.

According to yet another preferred embodiment of the present invention the composition further comprises a carrier. Usually the tumor associated antigen peptide(s) are presented in context of the carrier. The carrier can be a proteinaceous carrier to which the peptides are linked. Methods of linking short peptides to carriers are well known in the art of vaccination. The carrier can alternatively be a particulate adjuvant, an oil or emulsifier based adjuvant, a gel based type adjuvant, or an adjuvant based on specific targeting of antigen, such as, but not limited to, antibody-liposome conjugates. The carrier can also be a protein or a recombinant protein produced, for example in bacteria, yeast or in mammalian cells, including cytokines, such as IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, interferon-α, interferon-β, interferon-γ and others. The carrier can also be an antigen presenting cell, such as, but not limited to, a dendritic cell, a macrophage, a B cell or a fibroblast. The cell selected is either an autologous or non-autologous HLA matching cell. Optionally, the cell can be a cultured cell, a cell treated by various reagents (e.g., by early and/or late acting cytokines), transduced by genes, and/or irradiated or radiated.

The pharmaceutical composition according to the present invention, which is preferably a vaccine composition, is effective in treating or inhibiting the development of cancer and/or cancer metastases. In other words, the composition is effective for primary tumors, secondary tumors and metastases thereof in the same organ or in another organ, provided that the tumor expresses the above listed tumor associated proteins. According to a preferred embodiment of the present invention, the cancer being treated or whose development is inhibited via the administration of the vaccine composition is a carcinoma, i.e., a malignant tumor composed of epithelial tissue, of the colon or prostate.

For therapeutic or prophylactic anti-tumor treatment, the vaccine composition according to the present invention may include thickeners, carriers, excipients, buffers, diluents, surface active agents, auxiliary agents, preservatives, and the like, all as well known in the art. The composition may also include one or more active ingredients, such as, but not limited to, anti-inflammatory agents, anti-microbial agents, anesthetics and the like.

The vaccine composition may be administered in either one or more ways. Administration may be effected topically (including ophthalmically, vaginally, rectally, intranasally), orally, by inhalation, or parenterally, for example by intravenous drip or intraperitoneal, intravesical, subcutaneous, or intramuscular injection.

Compositions for topical administration can include, but are not limited to, lotions, ointments, gels, creams, suppositories, drops, liquids, sprays and powders. Conventional pharmaceutical carriers, aqueous, powder or oily bases, thickeners and the like may be necessary or desirable.

Formulations for parenteral administration can include, but are not limited to, sterile aqueous solutions which may also contain buffers, diluents, adjuvant and other suitable additives. The adjuvant is preferably of a type allowed for use in treating human beings, such as BCG adjuvant.

Dosing is dependent on responsiveness, but will normally be one or more doses per week or month, with course of treatment lasting from several weeks to several months. Persons ordinarily skilled in the art can easily determine optimum dosages, dosing methodologies and repetition rates.

The present invention provides novel tumor associated antigen peptides effective in eliciting CTL response which can therefore be effective therapeutic agents to combat cancer.

The present invention further provides a method for treating or for inhibiting the development of colon cancer which involve administering to a patient in need thereof a molecule which includes the antigen-binding portion of an antibody specific for the tumor associated antigen, human 1-8D interferon induced transmembrane protein 2, to treat or inhibit the development of colon cancer in the patient, such as by direct cytotoxicity of the antibody, e.g., as mediated by complement (CDC) or by effector cells (ADCC).

A still further aspect of the present invention relates to a method for determining overexpression of human 1-8D interferon induced transmembrane protein 2 in human colon cells, involving immunohistochemistry, such as contacting a sample of colon cells from a patient with a molecule which includes the antigen-binding portion of an antibody specific for human 1-8D interferon induced transmembrane protein 2, then detecting binding of the molecule to the colon cells and determining the level of expression of human 1-8D interferon induced transmembrane protein 2 by the colon cells from the patient sample.

It should be understood that when the term "antibody" is used, this is intended to include intact antibodies, such as polyclonal antibodies or monoclonal antibodies (mAbs), as well as proteolytic fragments thereof such as the Fab or F(ab')2 fragments. Furthermore, the DNA encoding the variable region of the antibody can be inserted into other antibodies to produce chimeric antibodies (see, for example, U.S. Pat. No. 4,816,567) or into T-cell receptors to produce T-cells with the same broad specificity (see Eshhar, et al, 1990 and Gross et al, 1989). Single-chain antibodies can also be produced and used. Single-chain antibodies can be single-chain composite polypeptides having antigen binding capabilities and comprising a pair of amino acid sequences homologous or analogous to the variable regions of an immunoglobulin light and heavy chain (linked VH-VL or single-chain FV). Both VH and VL may copy natural monoclonal antibody sequences or one or both of the chains may comprise a CDR-FR construct of the type described in U.S. Pat. No. 5,091,513 (the entire content of which is hereby incorporated herein by reference). The separate polypeptides analogous to the variable regions of the light and heavy chains are held together by a polypeptide linker. Methods of production of such single-chain antibodies, particularly where the DNA encoding the polypeptide structures of the VH and VL chains are known, may be accomplished in accordance with the methods described, for example, in U.S. Pat. Nos. 4,946,778, 5,091, 513 and 5,096,815, the entire contents of each of which are hereby incorporated herein by reference.

An antibody is said to be "capable of binding" a molecule if it is capable of specifically reacting with the molecule to thereby bind the molecule to the antibody. The term "epitope" is meant to refer to that portion of any molecule capable of being bound by an antibody which can also be recognized by that antibody. Epitopes or "antigenic determinants" usually consist of chemically active surface groupings of molecules such as amino acids or sugar side chains and have specific three dimensional structural characteristics as well as specific charge characteristics.

Polyclonal antibodies are heterogeneous populations of antibody molecules derived from the sera of animals immunized with an antigen.

Monoclonal antibodies (mAbs) are a substantially homogeneous population of antibodies to specific antigens. MAbs may be obtained by methods known to those skilled in the art. See, for example Kohler et al, (1975); U.S. Pat. No. 4,376,110; Harlow et al, (1988); and Colligan et al, (2002), the entire contents of which references are incorporated entirely herein by reference. Such antibodies may be of any immunoglobulin class including IgG, IgM, IgE, IgA, and any subclass thereof. The hybridoma producing the mAbs of this invention may be cultivated in vitro or in vivo. High titers of mAbs can be obtained by in vivo production where cells from the individual hybridomas are injected intraperitoneally into pristane-primed Balb/c mice to produce ascites fluid containing high concentrations of the desired mAbs. MAbs of isotype IgM or IgG may be purified from such ascites fluids, or from culture supernatants, using column chromatography methods well known to those of skill in the art.

Chimeric antibodies are molecules, the different portions of which are derived from different animal species, such as those having a variable region derived from a murine mAb and a human immunoglobulin constant region. Chimeric antibodies are primarily used to reduce immunogenicity during application and to increase yields in production, for example, where murine mAbs have higher yields from hybridomas but higher immunogenicity in humans, such that human/murine chimeric or humanized mAbs are used. Chimeric and humanized antibodies and methods for their production are well-known in the art, such as Cabilly et al (1984), Morrison et al (1984), Boulianne et al (1984), European Patent 0 125 023, Neuberger et al, European Patent 0 171 496, European Patent 0 173 494, WO 8601533, European Patent 0 184 187, Sahagan et al (1986); WO 9702671 (1987), Liu et al (1987), Sun et al (1987), Better et al (1988), and Harlow et al (1988). These references are hereby incorporated herein by reference.

A "molecule which includes the antigen-binding portion of an antibody," is intended to include not only intact immunoglobulin molecules of any isotype and generated by any animal cell line or microorganism, or generated in vitro, such as by phage display technology for constructing recombinant antibodies, but also the antigen-binding reactive fraction thereof, including, but not limited to, the Fab fragment, the Fab' fragment, the F(ab')2 fragment, the variable portion of the heavy and/or light chains thereof, and chimeric or single-chain antibodies incorporating such reactive fraction, or molecules developed to deliver therapeutic moieties by means of a portion of the molecule containing such a reactive fraction. Such molecules may be provided by any known technique, including, but not limited to, enzymatic cleavage, peptide synthesis or recombinant techniques. A recent paper by Lev et al. (2002) is representative of the state of the art with respect to human recombinant antibodies directed towards expressed tumor T cell epitopes.

Having now generally described the invention, the same will be more readily understood through reference to the following examples which are provided by way of illustration and are not intended to be limiting of the present invention.

Example 1

1-8 Interferon Inducible Gene Family—Putative Colon Carcinoma Associated Antigens $D^{b-/-} \times \beta 2$ microglobulin ($\beta$2m) null mice transgenic for a chimeric HLA-A2.1/Db-$\beta$2m single chain (HHD mice) are an effective biological tool to evaluate the anti-tumor CTL response of known tumor associated antigen MHC restricted peptides and to screen for putative unknown novel peptides. In this study, over 500 HLA-A2.1 restricted peptides derived from colon carcinoma overexpressed genes were screened with HHD derived lymphocytes. This procedure culminated in the identification of seven immunogenic peptides, three of which were derived from the "1-8D gene family" that were both antigenic and immunogenic in the HHD mice. The peptides were shown to induce CTL that were able to kill a colon carcinoma cell line HCT-15 in vitro and retard its growth in vivo. One of the peptides shared by all the 1-8 gene family efficiently primed normal human CTL precursors. These results highlight the 1-8D gene and its homologues as putative immunodominant TAAs of colon carcinoma.

Materials and Methods

Mice. The derivation of HLA-A2.1/$D^{b}$-$\beta$2 monochain, transgenic, H-$2D^{b} \times \beta$2m double-knockout mice (named HHD mice) has been described before (Pascolo et al., 1997). CD1-nude mice were bred in the Weizmann Institute of Science (Rehovot, Israel). Animals were maintained and treated according to NIH guidelines.

Tumor cells. HCT-15 is a human colon carcinoma cell line negative for expression of HLA class I molecules. The HCT/HHD is a HHD transfectant of HCT-15. HCT/HHD/B7.1 cells are murine B7.1 transfectants of HCT/HHD. RMA-S is a TAP-2 deficient lymphoma clone of C57BL/6 origin. RMA-S/HHD/B7.1 are HHD and murine B7.1 transfectants. T2 is a TAP-2-deficient lymphoblastoid line of HLA-A2.1 genotype. EL4/HHD were kindly provided by Dr. F. A. Lemonnier, Pasteur Institute, Paris, France. EL4/HHD/1-8D-Myc were prepared by transfection of EL4/HHD with pcDNA3.1/Hygro(+) (Invitrogen, CA) using LipofectAMINE (Life Technologies, Gaithersburg, Md.) according to manufacturer's protocols. Transfectants were grown in RPMI containing 10% FCS, combined antibiotics, 2mM glutamine, $5 \times 10^{-5}$M $\beta$ME and 50 µg/ml hygromycin.

Peptide Synthesis. Peptides were synthesized on an ABIMED AMS 22 multiple peptide synthesizer (Abimed, Langenfeld, Germany), employing Fmoc strategy following manufacturer's protocols. Crude peptides were purified by RP-HPLC. For the screening experiments peptides were synthesized by a Multi-Parallel Synthesis (MPS) method adapted to 96-well plates developed by Peptor Ltd. (Rehovot, Israel). The peptides were purified by solid phase extraction over C-18 Sep-Pak resin and analyzed by VG platform, API-ESI MS (Fisons, UK). The average purity of the MPS peptides was about 80% as analyzed by RP-HPLC.

Vaccination. HHD mice were immunized i.p. 3 times at 7-day intervals with $2 \times 10^{6}$ irradiated (5000 rad) tumor cells, or irradiated peptide-loaded RMA-S/HHD/B7.1 transfectants. Spleens were removed on day 10 after the last immunization, and splenocytes were restimulated in vitro, either with irradiated tumor cells or with one third of the lymphocytes pre-pulsed with 100 µM synthetic peptides in opti- MEM (Life Technologies) for 2 hr at 37° C., 5% $CO_2$. Restimulated lymphocytes were cultured in RPMI-HEPES medium containing 10% FCS, 2 mM glutamine, combined antibiotics, 1 mM sodium pyruvate, 25 mM HEPES, $5×10^{-5}$M PME and 1% NEAA for 5 days. Viable cells (effectors) were separated by Lympholyte-M (Cedarlane, Hornby, Canada) gradient, resuspended and admixed at different ratios with 5,000 $^{35}$S-methionine-labeled target cells. Cytolytic assays were carried out as described previously in Carmon et al., 2000. Extracts of tumor peptides or normal colon peptides were prepared from a pool of 6 post-surgical colon carcinoma specimens as described before Carmon et al., 2000.

RNA preparation and RT-RCR. Total RNA from human tumor and normal colon tissues and from HCT-15 colon carcinoma cell line were isolated by TRI REAGENT (Molecular Research Center, Cincinnati, Ohio, USA) according to the manufacturer's instructions. Reverse transcription was done on 5 μg of total RNA with an oligo (dT) primer using reverse transcriptase (Superscript™ II Rnase H-reverse transcriptase kit, Invitrogen, Carlsbad, Calif.). cDNA was PCR amplified (Tgradient, Whatman Biometra, Goettingen, Germany) for 35 cycles as described by Daido et al. (2001):1 min 94° C., 1 min 60° C., 1 min 72° C. Amplification was followed by 7 min incubation at 72° C. The following primers were used for amplification: sense primer for the 1-8D and 1-8U genes: 5'-ATGTCGTCTGGTCCCTGTTC-3' (SEQ ID NO:56), antisense primer for the 1-8D and 1-8U genes: 5'-GCCATTGTAGAAAAGCGTGT-3' (SEQ ID NO:57). The sizes of PCR products were expected to be 436 bp for the 1-8D gene and 368 bp for the 1-8U. To verify the validity of cDNA samples, expression of GAPDH (580 bp) in the same cDNA samples was tested. Products were separated on 2% agarose gel.

Cloning of 1-8D gene. Total RNA was isolated from colon tumor specimens using TriReagent (Molecular Research Center, OH). Two μg of total RNA were converted to cDNA using SuperScript II kit (Life Technologies). 1-8D gene was amplified by PCR using the 5' primer-GGAAACTGTTGAGAAAACGGAACTAC (SEQ ID NO:1) and 3' primer-AATGCCATTGTAGAAAAGCGTGTG (SEQ ID NO:2). The 688 bp band was purified and cloned into pcDNA3.1/Hygro(+) vector between HindIII and XhoI restriction sites using the following primers:

```
5' primer- 5'-GGTAAGCTTACCGCCGCTGGTCACCATGAACC-3'
(SEQ ID NO: 3);

3' primer- 5'-AGAGCTCGAGGCCTCAATGATGCCTCCTGATCTA
TCG-3' (SEQ ID NO: 4).
```

Myc tag was added by eliminating the stop codon and introducing the amino acid sequence: YLEEQKLISEEDLGSIDV (SEQ ID NO:5) at the C-terminus (the Myc epitope is underlined). Positive clones were selected by intracellular staining using Cytofix/Cytoperm Plus kit (Pharmingen, CA) using aMyc (9E10) mAb (Santa-Cruz Biotechnologies, CA).

Adoptive transfer. CD1-nude mice were challenged in the footpad with $3×10^6$ HCT/HHD cells. Three days later, $10^7$ viable re-stimulated effector cells were injected i.v. to the tail vein. One thousand units of IL-2, was injected i.p. twice a day for 7 consecutive days post transfer. Tumor growth was monitored by measuring the diameter of the footpad with calipers. Mice were sacrificed when one of the tumor diameters reached 10 mm.

In vitro priming of human CTL. Leukopheresis products of four healthy donors were obtained from Barzilai Medical Center (Ashkelon, Israel) according to Declaration of Helsinki Principles. PMBC were isolated by centrifugation on Ficoll-Plaque Plus gradients (Amersham, Sweden). The procedure was carried out according to Thurner et al., with minor modifications. Briefly, in vitro priming was done over autologous DC that were prepared from monocytes by IL-4 and GM-CSF treatment and matured with a IL-1β, IL-6, TNF-α and $PGE_2$ cocktail. DC were pulsed with the synthetic peptides and PBMC were supplemented with IL-7. Two days later IL-2 was added and renewed every three days. The rest of the stimulations were done every 7 days over peptide pulsed monocytes. Seven days after the third stimulation lymphocytes were harvested for cytolytic assays.

Results

HCT/HHD and Colon Carcinoma Tumor Extracts Elicit Cross-Reactive CTLs in HHD Mice Successful screening of antigenic peptides relies upon reproducible screening procedures. Therefore, the HHD mice were vaccinated with a cellular preparation rather than extracts of tumor peptides that vary among preparations and where stability is needed to be carefully assessed every cycle of freezing and thawing. HCT-15 cells are colon carcinoma cells which do not express HLA class I molecules (FIGS. 1C and 1D) and serve as a convenient platform for transfection with the single-chain HHD construct. Stable HCT-15 transfectants that highly express the HHD and murine B7.1 (FIGS. 1A and 1B) were established. These cells were tested for cross-CTL activity to low molecular weight extract made from colon tumor specimens. HHD mice were inoculated with HCT/HD/B7.1 cells, their spleens were removed, and cytolytic activity was assayed (FIGS. 2A-2B). In the side by side complementary experiment, HHD mice were vaccinated with RMA-S/HHD/B7.1 loaded with tumor extract (TE) and cytolytic activity was measured on the indicated targets (FIG. 3). As can be seen, HCT/HHD/B7.1 elicits a powerful CTL response against itself in a HHD restricted manner (HCT/HHD vs. HCT). Interestingly, the CTL identify exclusively TE loaded on target cells, "ignoring" completely the same target cells loaded either with normal extract (NE) or tyrosinase derived peptide as a negative control. When RMA-S/HHD/B7.1 loaded with TE were used to induce a CTL response, HCT was again lysed in a HHD restricted manner and the response mounted against NE and tyrosinase unrelated peptide was roughly 20% less than the response against the TE itself. This high background is explained by reactivity to the RMA-S antigens, which are shared by all RMA-S/HHD loaded targets. This set of experiments demonstrates similarity and partial overlap between HCT antigens and antigens extracted from colon carcinoma tumor specimens.

Twenty Two Peptides are Antigenic to Anti-HCT/HHD/B7.1 Effector Cells.

The screening procedure used focused on 26 genes that were previously reported to be at least 5-fold overexpressed, in colon tumor compared to normal colon of the same patients. The proteins derived from these genes are putatively protein that are not secreted, which therefore serve as good substrates to the MHC class I processing machinery. The protein products of the genes, listed in Table 2, were screened for putative HLA-A2.1 restricted peptides using the "independent binding of individual peptide side-chains" software (Parker et al., 1994).

TABLE 2

Selection of HLA-A2.1-restricted peptides from colorectal (CR)-associated genes

| Gene No. | Gene name | No. of HLA-A2.1 peptides |
|---|---|---|
| 1 | Human defensin 6 | 11 |
| 2 | Human ADP/ATP translocase | 24 |
| 3 | Human parathymosin | 1 |
| 4 | Human 1-8U gene from interferon inducible gene | 25 |
| 5 | Human chaperonin-like protein | 29 |
| 6 | Human SPARC/osteonectin | 23 |
| 7 | Human 1-8D gene from interferon inducible gene | 24 |
| 8 | Human TB2 gene | 29 |
| 9 | Human alpha-1 collagen | 12 |
| 10 | Human mRNA for dipeptidase | 19 |
| 11 | Fibronectin | 38 |
| 12 | Actin binding protein | 39 |
| 13 | HCG IV mRNA | 19 |
| 14 | HLA-DR antigens associated invariant gamma chain | 19 |
| 15 | MHC class I HLA-C.1 gene | 29 |
| 16 | polyA binding protein | 29 |
| 17 | Transforming growth factor-beta induced gene | 19 |
| 18 | *H. sapiens* mRNA for laminin-binding protein | 18 |
| 19 | Human mRNA sequence | 14 |
| 20 | Insulin like growth factor II | 19 |
| 21 | Human ribosomal protein L23a mRNA | 5 |
| 22 | Human acidic ribosomal phosphoprotein P1 | 8 |
| 23 | Human liver mRNA fragment DNA binding protein UPI | 5 |
| 24 | Ribosomal protein L37 | 1 |
| 25 | Human MHC protein homologous to chicken B complex | 29 |
| 26 | HB23 gene for B23 nucleophosmin | 15 |

CR-associated genes were selected according to the following rules:
1. Candidate genes with secretion sequences were excluded.
2. Candidate gene must be overexpressed in tumors at least 5 fold over expression in normal tissue.
HLA-A2.1-restricted peptides from the selected genes were selected according to its consensus binding motifs.

The number of low and medium affinity HLA-A2.1 restricted peptides (score over 1) that were selected is listed. These peptides were synthesized by the MPS synthesis technology, diluted with optiMEM to a concentration of approximately 1 mg/ml, loaded on 35S-methionine labeled RMA-S/HHD targets and mixed with anti-HCT/HHD/B7.1 in a 50:1 effector to target ratio. The HLA-A2.1 restricted tyrosinase peptide was used as a negative control. Targets that were lysed more than 10% over the negative control in two consecutive experiments were selected as antigenic peptides (Table 3). Table 3 lists antigenic HLA-A2.1 restricted peptides, their respective genes, position and antigenic scores that was deduced from the ratio of the specific lysis, obtained with HHD derived lymphocytes. Seven peptides are immunogenic (underlined). In bold are peptides 1-6, 3-5 and 3-7 that derive from 1-8D.

TABLE 3

CTL epitopes among colorectal (CR)-associated HLA-A2.1 restricted antigenic peptides

| Peptide no. | SEQ ID NO: | Name of gene | Position | Score |
|---|---|---|---|---|
| 1-1 VLYDELKKV | SEQ ID NO: 6 | Human ADP/ATP translocase | 253-261 | 121.7 |
| 1-2 LLVIIPVLV | SEQ ID NO: 7 | Human 1-8D gene from interferon inducible gene | 119-127 | 108.3 |
| 1-3 VQPQSPVAV | SEQ ID NO: 8 | Actin binding protein | 10-18 | 112.0 |
| 1-4 FELAAESDV | SEQ ID NO: 9 | Transforming growth factor beta induced gene | 380-338 | 83.3 |
| 1-5 GQQSTVSDV | SEQ ID NO: 10 | Actin binding protein | 1415-1423 | 125.0 |
| 1-6 EMKEEQEV | SEQ ID NO: 11 | Human 1-8D gene from interferon inducible gene | 20-28 | 181.3 |
| 1-7 IQQYGHQEV | SEQ ID NO: 12 | Actin binding protein | 657-665 | 94.6 |
| 1-8 ALRGHSHFV | SEQ ID NO: 13 | Human MHC protein homologous to chicken B complex | 58-66 | 106.7 |
| 1-9 VIATNILLV | SEQ ID NO: 14 | Human chaperonin-like protein | 368-346 | 69.7 |
| 1-10 TILTAVLLV | SEQ ID NO: 15 | Human defensin 6 | 5-13 | 97.5 |
| 1-11 IVDDITYNV | SEQ ID NO: 16 | Actin binding protein | 492-500 | 126.8 |
| 1-12 TLQLSRAPV | SEQ ID NO: 17 | Human mRNA for dipeptidase | 223-231 | 107.9 |
| 2-1 ALPDETEVV | SEQ ID NO: 18 | Human osteonectin | 23-31 | 115.0 |
| 2-2 IPMGKSMLV | SEQ ID NO: 19 | Insulin like growth factor II | 3-11 | 9.5 |
| 2-3 KIEDNNTLV | SEQ ID NO: 20 | Human ribosomal protein L23a mRNA | 89-97 | 150.0 |
| 3-1 MLTINGKAI | SEQ ID NO: 21 | Transforming growth factor beta induced gene | 343-351 | 147.1 |
| 3-2 SIAEFFSDI | SEQ ID NO: 22 | Human TB2 gene | 105-113 | 143.2 |
| 3-3 ALGFYPAEI | SEQ ID NO: 23 | Human thyroid hormone binding protein (p55) | 229-237 | 93.6 |
| 3-4 WVVYGVFSI | SEQ ID NO: 24 | Human TB2 gene | 98-106 | 90.9 |
| 3-5 LILGIFMTI | SEQ ID NO: 25 | Human 1-8D gene from interferon inducible gene | 110-118 | 176.7 |
| 3-6 DLQETLVKI | SEQ ID NO: 26 | Human chaperonin like protein | 316-324 | 84.6 |

TABLE 3-continued

CTL epitopes among colorectal (CR)-associated HLA-A2.1 restricted antigenic peptides

| Peptide no. | SEQ ID NO: | Name of gene | Position | Score |
|---|---|---|---|---|
| 3-7 KCLNIWALI | SEQ ID NO: 27 | Human 1-8D and 1-8U genes from interferon inducible genes | 103-111 | 487.5 |

Seven Peptides Derived From Overexpressed Genes are Immunogenic in HHD Mice

The antigenic peptides were tested for their specific immunogenicity in HHD mice. HHD mice were vaccinated with RMA-S/HHD/B7.1 cells loaded with each of the peptides (listed in Table 3), their spleens were removed, and resensitized in vitro with synthetic peptides for four days. On the fifth day, a cytolytic assay was performed on two targets, either the peptide itself loaded on labeled RMA-S/HHD or the tyrosinase peptide as a negative control. The ratio of specific lysis between specific and tyrosinase peptides was defined as "immunogenic score". This experiment was repeated twice and the average score of each of the antigenic peptides is specified (Table 3 and FIG. 4). The horizontal line in FIG. 4 represents the limit of 95% significance as defined by assuming normal distribution of scores. Seven peptides (Table 3, underlined) out of the 22 antigenic peptides were found to be significantly (score>1.25) immunogenic in the HHD mice. Unexpectedly, three of the seven, peptides 1-6, 3-5 and 3-7, which showed the highest scores, were derived from the same protein, which gene of origin is the "human 1-8D interferon inducible gene".

The Peptides of "1-8D Gene" Induce Anti-HCT/HHD CTL Response

Figure 5A:
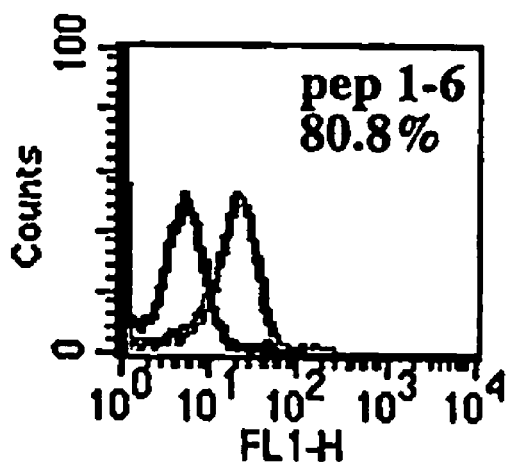
FIGS. 5A-5D are FACS analyses showing that the 1-8D peptides, peptide 1-6 (FIG. 5A), peptide 3-5 (FIG. 5B) and peptide 3-7 (FIG. 5C), stabilize HLA-A2 on T2 cells. T2 cells were acid stripped and incubated with the indicated peptide and recombinant β2m or with β2m alone as a negative control.
Figure 5B:
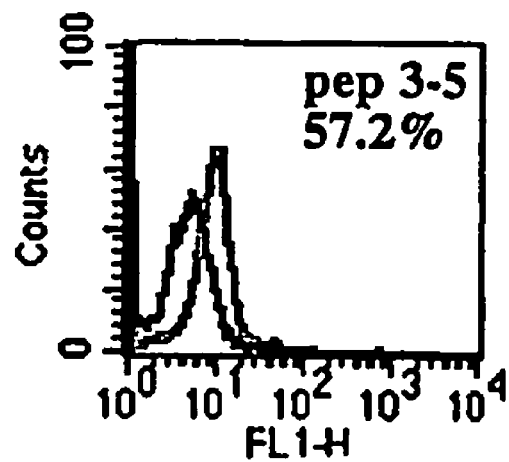
Figure 5C:
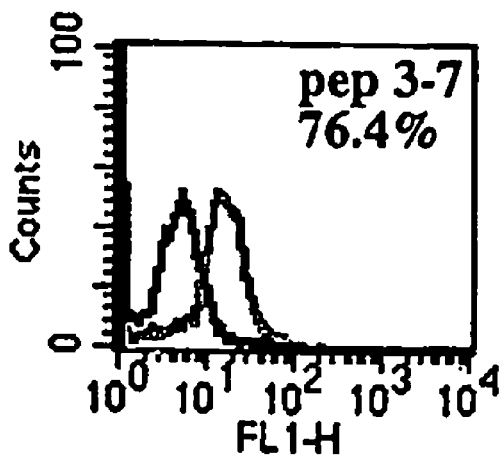
Figure 5D:
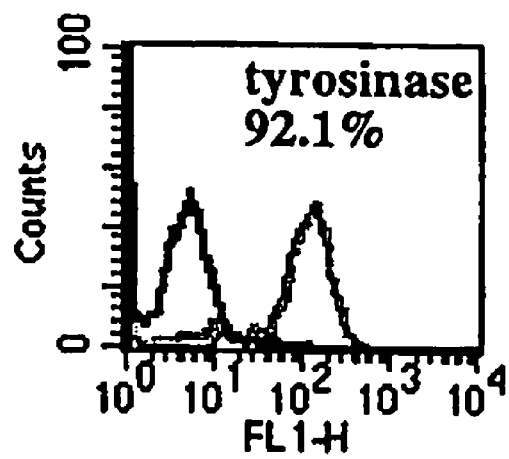
Figure 6:
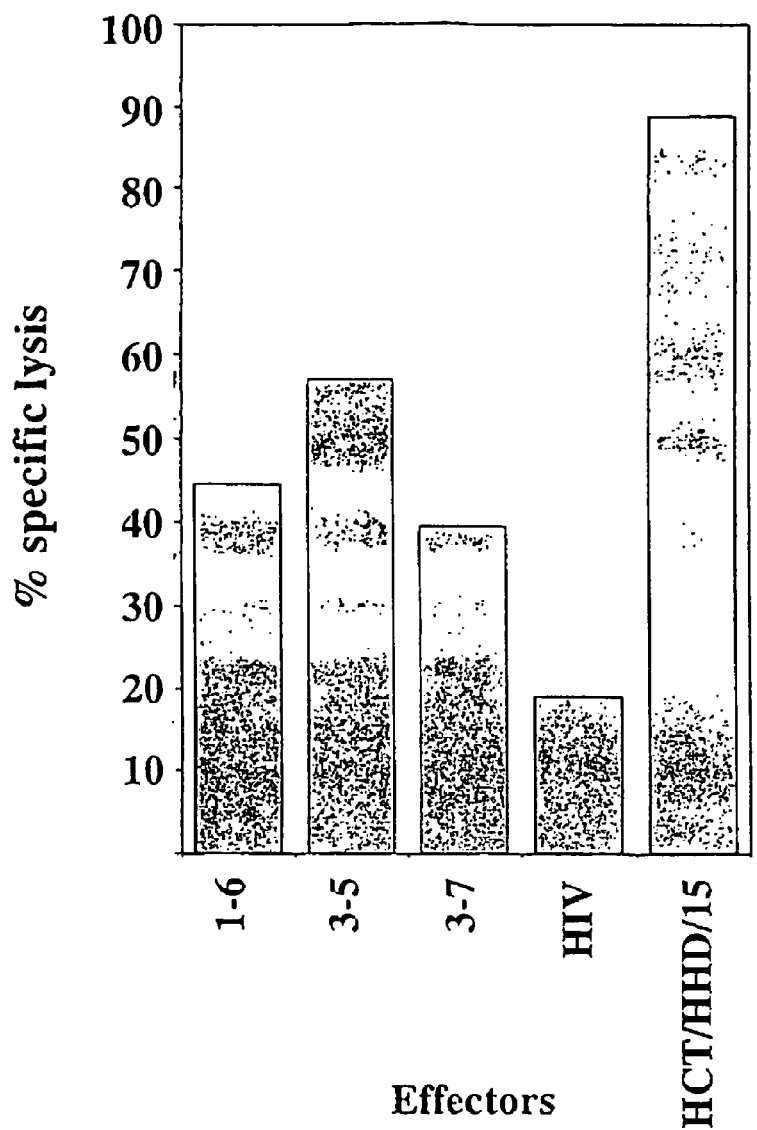
FIG. 6 is a graph showing that the 1-8D peptides can mount anti-HCT/HHD CTL responses. HHD mice were immunized with HCT/HHD/B7.1 and with peptide loaded on RMA-S/HHD/B7.1. In vitro cytolytic assays were performed using HCT/HHD cells as targets. The specific lysis at E:T in 50:1 ratio of a representative experiment out of three is shown.

Intrigued by this finding, the laboratory of the present inventors focused on the 1-8D peptides. Peptide binding to HLA-A2.1 was verified by a T2 stabilization assay (Firat et al., 1999). FIGS. 5A-5C show that the three 1-8D peptides bind to HLA-A2.1, although with lower capacity than the tyrosinase peptide (FIG. 5D), which is considered to be a high HLA-A2.1 binder. 1-8D peptides were next tested for induction of anti-HCT/HHD CTL responses by vaccinating HHD mice with the 1-8D peptides (Carmon et al., 2000). As a negative control, an HIV derived peptide TLNAWVKVV (SEQ ID NO:28), that is a weak immunogen in the HHD model (F. A. Lemonnier, unpublished), was used. FIG. 6 shows that the three 1-8D peptides induce CTL that specifically lyse HCT/HHD cells.

Figure 7:
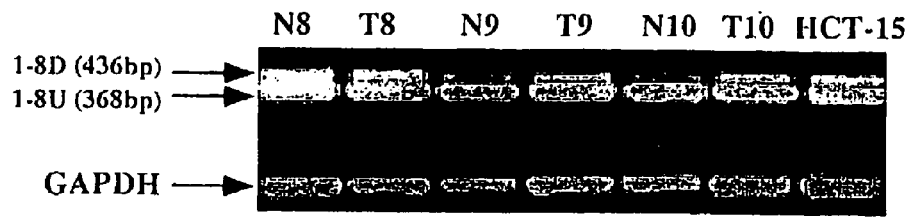
FIG. 7 is a gel showing that 1-8D and 1-8U expression in the colon carcinoma cell line HCT/HHD, in normal (N8-N10) and tumor samples (T8-T10) were detected by RT-PCR. RNA was extracted and cDNA was produced. The cDNA served as a template in PCR amplification with specific primers as described in the materials and methods section of Example 1.

Expression of 1-8D and 1-8U were detected in the HCT-15/HHD colon carcinoma cell line by RT-PCR using common primers. A PCR product of 368 bp, representing 1-8U, and a PCR product of 436 bp, representing 1-8D, are shown in FIG. 7. Tumor (T8-T10) and normal (N8-N10) specimens from colon cancer patients were analyzed in parallel. 1-8U was detected at similar levels in all samples while expression of 1-8D (436 bp) varied between samples. This band was more intense in T9 and T10, as compared to the normal tissues N9 and N10.

1-8D Peptides are Presented on EL4/HHD/1-8D-Myc

Figure 8A:
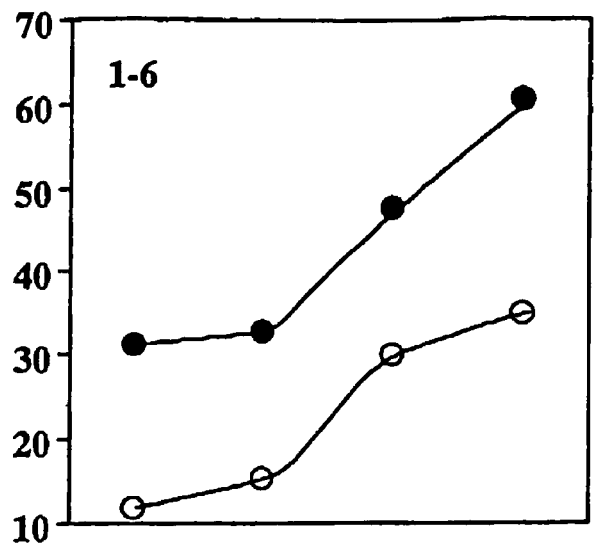
FIGS. 8A-8C are graphs that show 1-8D peptides 1-6 (FIG. 8A), 3-5 (FIG. 8B), and 3-7 (FIG. 8C) mount CTL responses that lyse 1-8D transfectants. Each peptide was loaded on RMA-S/HHD/B7.1 and used to immunize HHD mice. In vitro cytolytic assays were performed using EL4/HHD cells (open circles) and EL4/HHD/1-8D transfected cells (dark circles) as a target. The specific lysis of a representative experiment out of three is shown.
Figure 8B:
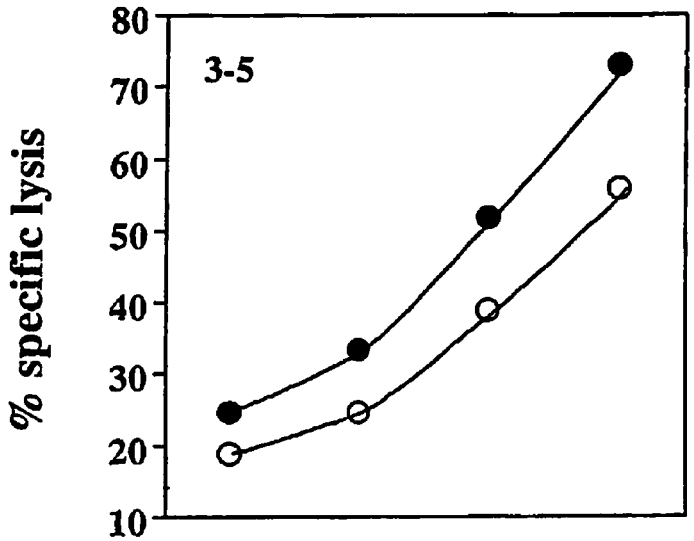
Figure 8C:
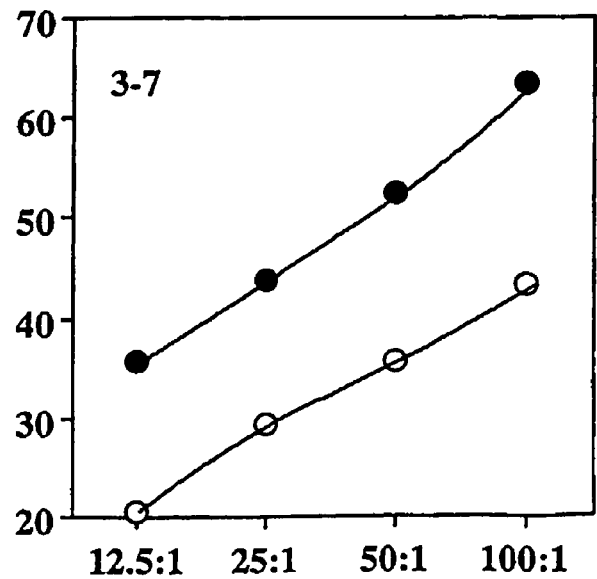

The 1-8D peptides are presented by HHD molecules on HCT/HHD cells. To demonstrate that murine cells can process the 1-8D protein and present the various peptides, the 1-8D mRNA was cloned by RT-PCR of RNA extracted from excised colon carcinoma tissues and inserted (and fused to a Myc tag at its 3') into a pcDNA3.1 vector. The plasmid was stably transfected into EL4 cells together with an HHD plasmid. HHD mice were immunized with the 1-8D peptides and a cytolytic assay was performed. The susceptibility of EL4/HHD/1-8D transfectant and the parental EL4/HHD cells to be lysed by anti-1-8D lymphocytes were compared. FIG. 8A-8C summarizes the results of these cytolytic experiments.

Adoptively Transferred Anti-1-8D Peptide Lymphocytes Inhibit the Growth of HCT/HHD in Nude Mice The anti-tumor efficacy of anti-1-8D peptide CTL was evaluated next. A transfer model, in which HCT/HHD cells were inoculated to the footpads of nude mice, was established. Three days post footpad challenge, in vitro restimulated HHD lymphocytes were transferred i.v. and the tumor growth was monitored. The kinetics of tumor growth, presented in FIG. 9, revealed significant retardation in tumor growth for peptide 3-5 starting from day 11 ($P<0.05$) and for peptides 1-6 and 3-7 starting from day 13 ($P<0.05$) applying the one tailed student t-test.

1-8D Derived Peptides Activate Peripheral CTL Precursors in Normal Human PBMC

Figure 10:
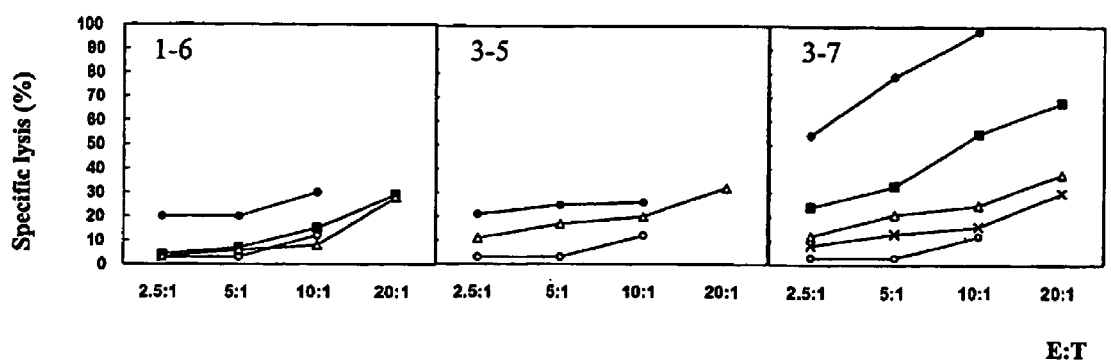
FIG. 10 are graphs showing PMBC from 4 donors checked for existence of CTL precursors. Left hand panel-peptide 1-6 stimulated CTLp. Middle Panel-peptide 3-5 stimulated CTLp. Right hand panel-peptide 3-7 stimulated CTLp. Peptide 1-6 stimulated low yet specific CTL activity in lymphocytes of donor B but not donors A and C. Peptide 3-5 stimulated low yet specific CTL activity in lymphocytes from donors B and C. Peptide 3-7 can stimulate high CTL activity in lymphocytes from donors A and B and low activity in donors C and D. PMBC of leukopheresis samples were isolated and in vitro priming was done with peptide pulsed autologous DC. PBMC were supplemented with IL-7, and two days later IL-2 was added and renewed every three days. The rest of the stimulations were done every 7 days over peptide pulsed monocytes. Seven days after the third stimulation, lymphocytes were harvested and a cytolytic assay was performed using peptide pulsed (closed squares, closed circles, open triangles, X signs) or non-pulsed T2 cells (open circles) as targets. Closed squares represent CTLp from donor A, closed circles represent CTLp from donor B, open triangles represent CTLp from donor C, Xs represent CTLp from donor D, and open circles represent non-pulsed T2 cells.
Figure 11A:
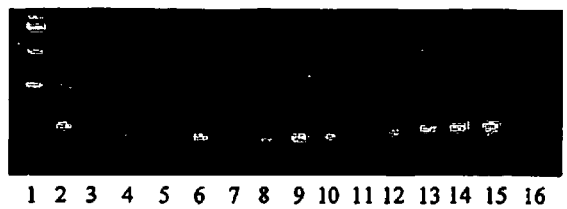
FIGS. 11A-11E are gels showing RT-PCR analysis of antigen expression using total cytoplasmic RNA isolated from logarithmically growing cell culture. Tissue samples from patients with prostatic carcinomas and BPH were frozen in liquid nitrogen, and RNA was isolated using the TRIREAGENT kit (Molecular Research Center, Cincinnati, Ohio) according to the manufacturer's instructions. Tissue samples were obtained from a patient who had undergone radical prostatectomy. All tissues were histologically confirmed as BPH or carcinoma of prostate. 5 μg of total RNA was reverse transcribed into cDNA with Superscript II kit. cDNA corresponding to 500 ng of total RNA was used for PCR where
Figure 11B:
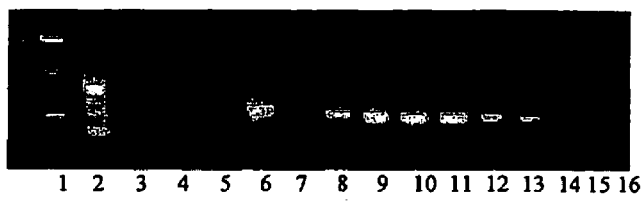
Figure 11C:
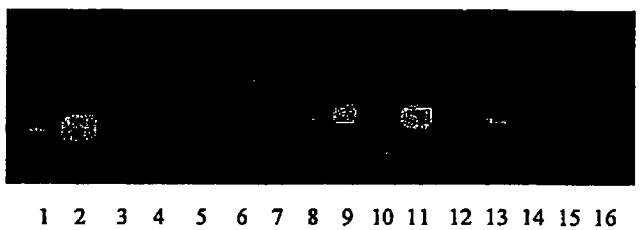
Figure 11D:
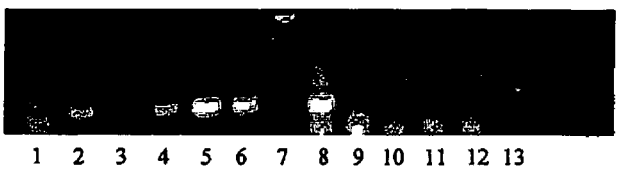
Figure 11E:
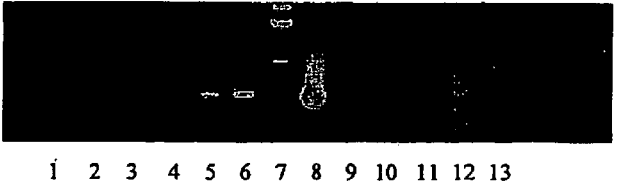
Figure 12A:
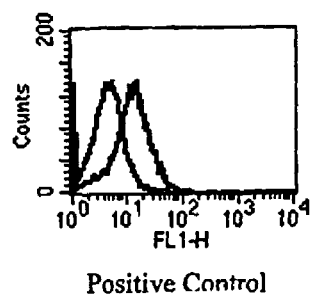
FIGS. 12A-12L show FACS analysis to determine predicted peptide binding of PAP-1 (FIG. 12B), PSMA-1 (FIG. 12C), PSA-1 (FIG. 12D), PAP-2 (FIG. 12E), PSMA-2 (FIG. 12F), PSA-2 (FIG. 12G), PAP-3 (FIG. 12H), PSMA-3 (FIG. 12I), STEAP-3 (FIG. 12J), PSGR-3 (FIG. 12K), PSGR-4 (FIG. 12L) to HLA-A2.1 molecules.
Figure 12B:
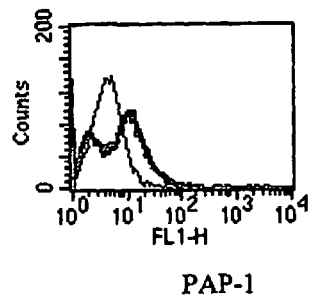
Figure 12C:
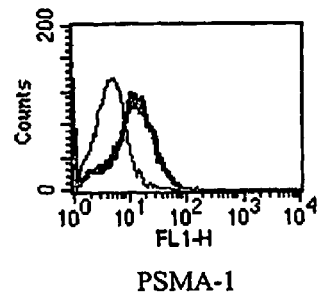
Figure 12D:
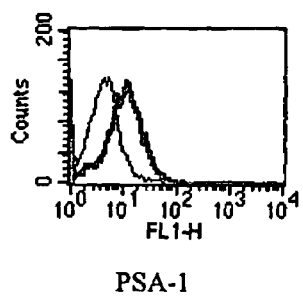
Figure 12E:
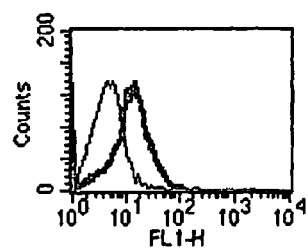
Figure 12F:
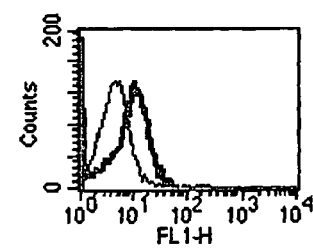
Figure 12G:
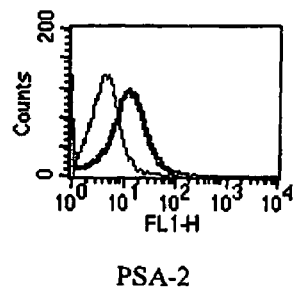
Figure 12H:
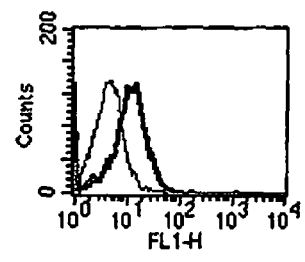
Figure 12I:
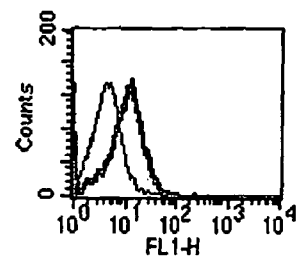
Figure 12J:
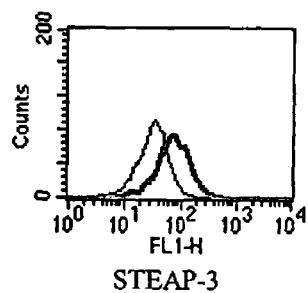
Figure 12K:
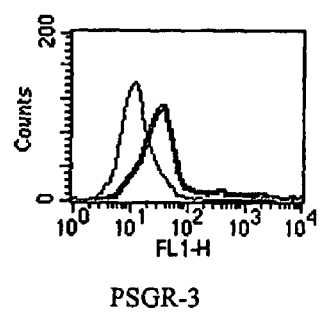
Figure 12L:
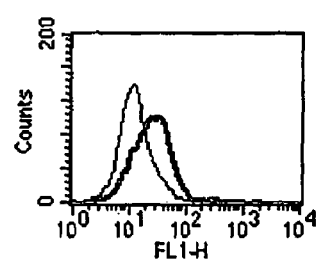

Finally, the peripheral blood of healthy individuals was checked for the existence of CTL precursors. Due to the paucity of PBMC from donor A and D the analysis of CTL from donor A was restricted to peptides 1-6 and 3-7 and from D to peptide 3-7. Peptide 3-7 was highly immunogenic in both donors A and B and lower in donors C and D (FIG. 10). Peptides 1-6 and peptide 3-5 showed immunogenicity in donor B but not in donor C.

Expression of 1-8 Genes in Normal Colon Tissues Versus Tumor Colon Tissues

Overexpression of 1-8D transcripts in 2/3 colon carcinoma fresh samples as compared to matching normal tissue was shown in FIG. 6. To extend these observations, 13 pairs of colon carcinoma/normal tissue were screened for expression of 1-8D, 1-8U and 9-27 transcripts by RT-PCR assays. To validate the origin of tissues, normal or tumor, transcripts of Carcinoembryonic Antigen (CEA), a protein overexpressed in more than 95% of colon carcinomas was also amplified. RNA from normal (N) and tumor (T) colon tissues was extracted and reverse-transcribed in order to make cDNA. cDNA from HCT-15, a human colon carcinoma line was used as positive control for expression of 1-8D and 1-8U and cDNA from the K562 erythroleukemia cell line was used as a positive control for expression of 9-27. PCR products of 436 bp 368 bp, 204 bp, and 641 bp, representing 1-8D, 1-8U, 9-27, and CEA, respectively, were monitored. The cDNA samples were semi-quantified using specific primers for GAPDH (583 bp), a metabolic gene ubiquitously expressed in tissues.

1-8U and 9-27 were detected at similar levels in all samples while the expression of 1-8D (436 bp) and CEA (641 bp), varied between the samples, as presented in Table 4. Table 4 presents the intensity of the 1-8D and CEA bands in normal tissues versus tumor tissues. Expression of the 1-8D gene was found in 5 of 13 normal tissues (N8, N9, N10, N14 and N18), and in 9 of 13 tumor tissues (T8, T9, T10, T13, T14, T15, T17, T18, and T20). Moreover, the 1-8D bands were more intense in T9, T10, T13, T15 and T17 as compared to the normal tissues N9, N10, N13, N15 and N17. The intensity of these bands was correlated to the intensity of CEA bands in these samples, which imply on their origin as normal or tumor tissues. Although these results are semiquantitive, they suggest that the 1-8D is an overexpressed gene in colon carcinoma.

TABLE 4

The expression of 1-8D and CEA in normal versus tumor tissues.

| Tissue | 1-8D | CEA |
|---|---|---|
| N8 | + | + |
| T8 | + | + |
| N9 | +/− | + |
| T9 | + | ++ |
| N10 | +/− | + |
| T10 | + | ++ |
| N11 | − | − |
| T11 | − | − |
| N12 | − | − |
| T12 | − | − |
| N13 | − | − |
| T13 | + | ++ |
| N14 | +/− | − |
| T14 | +/− | − |
| N15 | − | − |
| T15 | + | ++ |
| N16 | − | + |
| T16 | − | − |
| N17 | − | − |
| T17 | + | ++ |
| N18 | +/− | + |
| T18 | +/− | + |
| N19 | − | + |
| T19 | − | + |
| N20 | − | + |
| T20 | + | + |

The intensity of the 1-8D and CEA bands in normal versus tumor samples.
− represents no expression.
+/− low expression,
+ medium expression and
++ high expression.

Discussion

Several approaches have been taken to identify human tumor associated HLA class I restricted peptides. One approach utilizes CTL lines, derived from patients, either from blood circulation (peripheral T cells) or from the tumor tissue itself (tumor infiltrating lymphocytes), as a tool for the identification and characterization of TAA epitopes. The lines, when established, are then used to screen target cells transfected with cDNA libraries from the tumor, to screen peptide libraries or to test fractionated peptides extracted from tumors, and positive clones are further analyzed with synthetic peptides to zoom in on the nominal TAA epitopes (De Plaen et al., 1997). These approaches suffer from several difficulties. First, it is complex to establish carcinoma-associated CTL clones from peripheral lymphocytes. Second, CTL clones derived from cancer patients may represent, at least partially, the repertoire of an anergized immune system. Finally, the in vitro propagation of CTL might enhance sporadic clones surviving culture conditions rather than specific anti-tumor clones. An alternative strategy that bypasses these inherent pitfalls is based on the use of HLA transgenic mice.

Several studies have compared the CTL repertoire against defined HLA-A2.1 restricted epitopes in human PBMC to CTLs induced in HLA-A2.1 transgenic mice. Good concordance and an overlapping repertoire between the endogenous HLA-A2.1 and the murine transgenic HLA-A2.1 CTL repertoire were found, confirming the potential utility of such transgenic mice in the identification of human CTL epitopes (Shirai et al., 1995 and Wentworth et al., 1996). However, vaccination of HLA-transgenic mice with multi-epitope antigens, showed dominant murine H-2-restricted responses that masked the transgene restricted response (Barra et al., 1993).

To obtain pure HLA-restricted CTL responses, $D^b$X$\beta$2 microglobulin ($\beta_2$m) null mice transgenic for a recombinant HLA-A2.1/$D^b$-$\beta$2m single chain (HHD mice) were used. These mice combine classical HLA transgenesis with selective destruction of murine H-2. Therefore, unlike classical HLA transgenics, these mice show only HLA-A2.1-restricted responses with multi-epitope proteins such as intact viruses (Firat et al., 1999 and Pascolo et al., 1997) and can be used as a suitable tool for identifying potential CTL epitopes.

HCT/HHD/B7.1 cells were chosen as the immunogen in HHD mice since the HCT-15 is HLA negative and does not induce xenogeneic responses. High expression of HHD and B7.1 modified it to be a suitable APC, and CTL analysis showed shared TAAs with peptides extracted from fresh tumors. Moreover, high reproducibility and apparent tumor specificity were recorded for these CTL (FIGS. 2A-2B and 3). Based on these considerations, a reverse immunology approach was combined with a screening procedure that utilizes HHD lymphocytes to identify immunodominant epitopes of colon carcinoma overexpressed genes. As was already shown, overexpressed ubiquitously expressed genes, like telomerase and p53, are used as TAA targets for immunotherapy (Minev et al., 2000 and Brossart et al., 1998). In the context of colorectal carcinoma, CEA and Her-2/neu derived peptides are used as immunogens for anti-tumor therapy with minimal residual damage to normal colon as a result of autoimmune reactions. This reinforces the notion that many other potential overexpressed genes might serve as useful targets without autoimmune damage (Kass et al., 1999 and Zhu et al., 2000). For this purpose, methods that simultaneously analyze a plethora of RNA transcripts such as DNA arrays and SAGE are highly useful (DeRisi et al., 1996 and Gress et al., 1996). Here, overexpression data that compared normal colon and colorectal carcinoma expression profile by SAGE as a basis for screening was utilized (Zhang et al., 1997).

The colon carcinoma cell line HCT-15 is characterized by both negative endogenous HLA expression and high tumorigenic properties. Since the present inventors aimed at inducing colon-associated HLA-A2.1-restricted response in the HHD transgenic mice, the HCT-15 cell-line was modified to be a suitable APC candidate after transfection with the HHD single chain and the costimulatory B7.1 molecule (Lewin et al., 1991). FIGS. 1A-1D show a FACS analysis of the HHD transfectants using the B9.12, an anti-human class I mAb. The HCT/HHD/B7.1 clone was highly positive and exhibited over 90% positive cells, while the parental cells were completely negative. When stained with CTLA-4 fused to an IgG molecule HCT/HHD/B7.1 cells showed 100% B7.1 staining (FIG. 1B). These cells were used to immunize HHD mice to obtain the lymphocytes for epitope selection. It was important to demonstrate that HCT/HHD/B7.1 elicits a CTL response that overlaps the response elicited with real TE to assure physiological significance of the screening used.

It was found that HCT/HHD/B7.1 elicits strong anti-self, HHD restricted CTL response that recognizes at 25:1 E:T exclusively the TE (FIGS. 2A and 2B). Furthermore, mice were immunized with RMA-S/HHD/B7.1 cells, loaded TE and HCT/HHD lysis was measured (FIG. 3). High specific lysis (over 60%) of the HCT/HHD cell line was obtained by anti-tumor extract activated lymphocytes. The lysis was five fold higher than of the parental cells. These results strongly suggest, that processing and presentation of HLA-A2.1-restricted and colon associated peptides take place by the HCT/HHD colon carcinoma cells. Likewise, the high specific lysis of HCT/HHD transfectants may indicate that there is an overlapping peptide repertoire between the tumor extracts and the colon tumor cell line.

A crucial parameter for selection of TAA peptide-based vaccines by CTLs is their presentation levels on the tumor cells surface as compared to normal tissues. Two fold preferential lysis of colon derived tumor peptide-versus normal tissue peptide-loaded targets could be observed upon vaccination with colon tumor extract peptides. This observation supports the existence of a window of specificity in the direction of the tumor tissue, towards which immunotherapy must be directed.

Excluding putative secreted proteins and selecting only the RNAs that are expressed at least 5 fold higher in tumors than in normal colon, the laboratory of the present inventors ended up with 26 genes, as listed in Table 2, that were analyzed for HLA-A2.1 restricted peptides. Using solid phase automatic peptide synthesis technology that was adapted to 96 well plates (MPS, Peptor Ltd., Israel), it was feasible to synthesize them all. Over 500 HLA-A2.1 restricted peptides derived from these genes were screened using lymphocytes derived from HCT/HHD/B7.1 immunized HHD mice. These lymphocytes recognized 22 peptides in cytolytic assays, rendering them antigenic to the lymphocytes (Table 3). To narrow down to only peptides that are immunogenic as well as antigenic, HHD mice were vaccinated with individual peptides, and lymphocytes were assayed for lysis of target cells loaded with the peptide itself or an irrelevant control peptide (tyrosinase or HIV NP derived peptides). A score was calculated reflecting the ratio of specific lysis of the peptide normalized to the control peptide. Interestingly, only seven peptides (underlined in Table 3 and marked with arrows in FIG. 4) could mount a significant CTL responses in HHD mice, while the rest were solely antigenic. Three of the seven were derived from the 1-8 family of interferon inducible proteins (1-8D in particular), highlighting these gene products as novel TAAs. Binding of the peptides to HLA-A2 was confirmed by stabilization assays on T2 cells (FIGS. 5A-5D).

Figure 9:
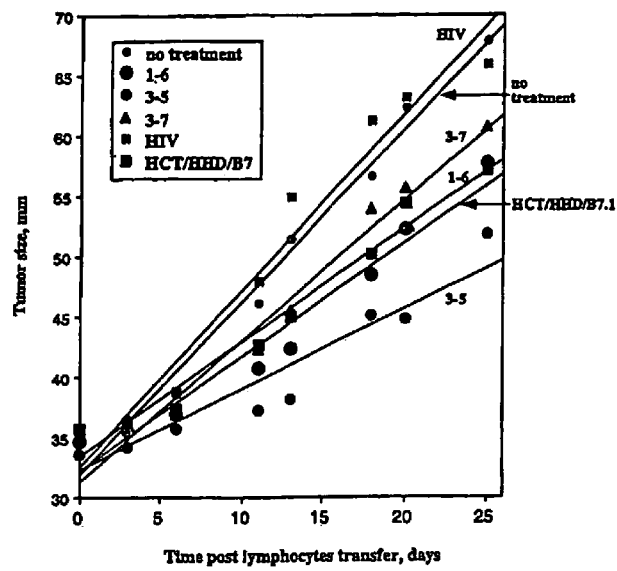
FIG. 9 is a graph showing that nude mice were challenged in the foot pad with HCT/HHD cells. Lymphocyte from vaccinated HHD mice were transferred together with IL-2 to the tumor bearing mice and the growth of the tumor was monitored twice a week. Statistical significance was achieved for peptides 1-6 and 3-7 from day 13 and for 3-5 treatment from day 11 (Student T-test, P<0.05).

It is further shown that CTL induced by peptides 1-6, 3-5 and 3-7 lyse the human colon carcinoma line HCT-15-HHD and the murine transfectant EL4/HHD/1-8D, indicating that these peptides are naturally processed and presented in human and mouse cells (FIG. 6 and data not shown). The high lysis of EL4/HHD parental cells is most probably due to the fact that RMA-S-HHD-B7, a murine C57BL lymphoma line serves as the APC in peptide vaccination and crossreacts with the EL4 C57BL lymphoma line. Adoptive transfer of CTL to 1-8D peptides significantly inhibited the growth of HCT/HHD tumors in nude mice further indicating that 1-8D is a tumor rejection antigen (FIG. 9).

The 1-8 gene family is inducible by both type I ($\alpha,\beta$) and type II ($\gamma$) interferons. Three members of the family, 1-8D, 1-8U and 9-27 are linked on an 18 Kb fragment of chromosome 11 and are highly homologous (Lewin et al., 1999). The 9-27 was shown to be an integral membrane protein identical to the Leu-13 antigen; it forms a complex with other proteins and is implicated in cell adhesion and growth inhibitory signals (Deblandre et al., 1995). The 1-8U was recently shown to be expressed in colitis associated colon cancer and in severely inflamed mucosa in ulcerative colitis (Hisamatsu et al., 1999), as well as in an androgen-independent variant of the prostate carcinoma line LNCaP but not in an androgen-dependent variant (Vaarala et al., 2000). Interestingly, 1-8D and 9-27 are induced by radiation in a p53 negative line, in an interferon independent mechanism (Clave et al., 1997). Recently, the expression of 1-8 gene family was found to be induced in a human adrenocortical carcinoma cell line in response to angiotensin II treatment, suggesting other signaling pathways for their induction (Daido et al., 2001). No other information is available on the 1-8D gene.

From these stages, effort was focused on characterization of 1-8D peptides: 1-6, 3-5 and 3-7 as potential antigens for vaccination against colon cancer. Interestingly, peptide 3-7, the most immunogenic peptide in HHD mice harbors a cysteine residue in its sequence. Moreover, the cysteine is situated exactly in the anchor position of HLA-A2.1 restriction pattern which prefers aliphatic amino acids like leucine. Conversely to the study of Chen et al (1999), in which they show that cysteine modification in vivo and in vitro is responsible for the subdominance phenotype of an influenza NP derived peptide, in this study, this peptide was found to be highly immunogenic. On the other hand, in agreement with Chen's findings, changing the cysteine to leucine enhanced the immunogenicity of the peptide, albeit without enhancing the binding to HLA-A2.1 (data not shown).

The peptides were further tested for their capacity to mount a CTL response against HCT/HHD. It was first confirmed that HCT/HHD cells indeed express 1-8D mRNA (FIG. 7). Overexpression of 1-8D was observed in ⅔ fresh tumor samples as compared to adjacent normal tissue while 1-8U was expressed at similar levels in all tested samples. HHD mice were vaccinated with 1-8D peptides and by a cytotoxic assay, higher specific lysis of HCT/HHD was demonstrated by each of the 1-8D derived peptide effector cells with respect to the HIV derived peptide (FIG. 6). The fact that HCT/HHD was recognized and lysed by anti-1-8D lymphocytes further strengthen the presumption of 1-8D immunodominance in this model.

EL4 cells, stably expressing the HHD construct, were transfected with 1-8D fused in its C-terminus to a Myc epitope. HHD mice were vaccinated with each of the 1-8D derived peptides and the susceptibility of EL4/HHD cells to be lysed by the active lymphocytes was compared to the 1-8D transfectant. Despite the high background lysis of EL4/HHD cells, the 1-8D transfectant was better lysed for peptides 1-6 and 37, while peptide 3-5 was roughly equal for the two targets. This fact might indicate natural processing and presentation of peptides 1-6 and 3-7, while less efficient presentation of peptide 3-5 by EL4 processing machinery (FIGS. 8A-8C). This assumption was further supported by the fact that mixing the anti-1-8D peptides lymphocytes before incubating with the targets did not improved the lysis of either HCT/HHD or EL4/HHD/1-8D but rather resulted in an average lysis (data not shown). This strongly suggests that the three peptides might be derived from the same protein and their HLA presentation is codependent one on the other.

The laboratory of the present inventors further checked whether activation of lymphocytes induced by the 1-8D peptides harbor an immunotherapeutic potential. An adoptive transfer model, in which nude mice were challenged in the footpad with a clone of HCT/HHD that was found to grow in these mice, was established. Three days post challenge, $10^7$ activated lymphocytes were transferred together with a maintenance dose of IL-2 (1000u×2/day). The tumor growth was monitored stringently. As can be seen in FIG. 9, 1-8D peptides retarded the in vivo growth of HCT/HHD. Despite its strong immunogenicity in this experiment, peptide 3-7 was found to be the least effective although statistical significance between the various 1-8D peptides was not achieved. Nonetheless, this result is in concordance with the in vitro cytolytic capacity of HCT/HHD that was measured ranking 3-5 as the most effective vaccine against HCT/HHD, 3-7 as the least effective, and 1-6 as being intermediate.

Owing to the strong genetic and familial etiology of colon cancer this type of carcinoma is in particular appealing to prophylactic treatment (Lindblom, 2001; Severin, 1999). Hence, the present inventors were interested in assessing the potential of 1-8D peptides to prime peripheral CTL of normal HLA-A2.1 positive donors. PBMC of two normal donors were isolated and assayed for the existence of CTL precursors (CTLp) by in vitro stimulations with autologous DC. After 4 consecutive stimulations, the CTL activity was measured using peptide pulsed T2 cells as targets. Peptide 3-7 was found to be highly efficient in activating peripheral CTLp to lyse target cells in a peptide specific manner for both donors. Peptides 1-6 and 3-5, however, were incompetent in doing so in this particular assay (FIGS. 10A, 10C and 10D). This might reflect either a specific gap in the T-cells repertoire in the donor's peripheral blood that might result from his additional HLA alleles or a more general phenomenon that result from specific HLA-A2.1 mediated tolerance to peptide 1-6. Additional experiments with PBMC of different donors will be needed to verify this finding. Intriguingly, peptide 3-7 is shared between the three members of the 1-8 gene family, while the other peptides (1-6 and 3-5) are unique for the 1-8D gene. The high immunogenicity of peptide 3-7 in the peripheral blood might be a influenced from the contribution from three distinct genes as opposed to the two other peptides that are restricted to the 1-8D.

In conclusion, a method is described here that combines reverse immunology coupled to screening with HHD derived activated lymphocytes to home in on HLA restricted peptides that are both antigenic and immunogenic in colon cancer. This method might be useful to select a relatively large number of cross-reactive peptides to human tumors with the aim to develop polyvalent anti-tumor vaccines. Screening over 500 peptides with anti-colon cancer cell line lymphocytes unveiled "human 1-8D of interferon inducible gene" as an immunodominant antigen of colon cancer. The laboratory of the present inventors further found that on top of contributing three HLA-A2.1 restricted peptides that show in vitro and in vivo cross-reactivity to HCT-15 cell line, the gene when cloned from colon carcinoma samples harbors three mutations as compared to the sequence published in the Genebank.

Example 2

Identification of Novel Prostate-Restricted Tumor-Associated Antigen Peptides

It is the aim of the experiments described in this example to identify novel TAAs as possible targets for immunotherapy and immunoprotection of prostate cancer. Ideal targets would include antigens that are exclusively expressed in prostate, that are overexpressed in malignant disease of the prostate and that are undergoing processing with consequent presentation at the cell surface. The oldest discovered prostate-restricted antigens have included prostate-specific antigen (PSA), prostate-specific membrane antigen (PSMA) and prostatic acid phosphatase (PAP). PAP, however, appears to be a more selective target for immunotherapy because PAP exhibits no more than 50% homology to any known protein, whereas PSA has 78% and 56% homology to human glandular and pancreatic/renal kallikrein, respectively. Moreover, PSMA appears to be expressed in non-prostatic tissues, including brain, salivary gland, and small intestine, when examined by immunohistochemistry (Fong et al., 1997). PSA and PSMA proteins were the only sources for peptides in clinical trials so far (Meidenbauer et al., 2000 et al., and Tjoa et al., 1999). Yet novel differentially expressed, prostate-specific genes were recently described which may be a potential source of immunogenic peptides. These include:

A) STEAP, a six-transmembrane epithelial antigen of prostate, is expressed predominantly in human prostate tissue and is up-regulated in multiple cancer lines, including prostate, bladder, colon, ovarian, and Ewing sarcoma (Hubert et al., 1999; protein accession number Q9UHE8; nucleic acid accession number NM 012449).

B) PTI-1, prostate tumor inducing gene-1, is differentially expressed in prostate cancer versus normal prostate and benign prostatic hypertrophy (BPH) as was identified by differential RNA display (Sun et al., 1997).

C) An androgen-regulated serine protease named Prostase was also identified as a gene with a prostate-restricted expression (Nelson et al., 1999).

D) PSCA, prostate stem cell antigen, is expressed predominantly on the cell surface. PSCA mRNA expression is prostate specific and highly up-regulated in both androgen-dependent and independent prostate cancer xenografts (Reiter et al., 1998).

E) PCTA-1, prostate carcinoma tumor antigen gene, is a member of the galectin gene family (40% sequence homology) that was also shown to be overexpressed by prostate carcinoma (Su et al., 1996).

F) PSGR, prostate specific gene with homology to G protein-coupled odorant receptor gene family. PSGR expression was shown to be restricted to human prostate tissues and its differential expression between tumor and normal specimens was highly significant (Xu et al., 2000; protein accession number Q9H255; nucleic acid accession number AF311306).

The materials and methods used in this example are described in the Brief Description of the Drawings section for FIGS. 9-14; otherwise, the materials and methods are those disclosed in WO 00/06723 and in the corresponding U.S. national stage application Ser. No. 09/744,804, the entire contents of which are incorporated herein by reference.

Results

The expression patterns of the above prostate-restricted antigens were first evaluated in three cell lines (LNCaP, Du-145, PC-3) derived from metastatic prostate carcinomas as well as in tissue samples from patients with CaP versus normal prostate tissue/benign prostatic hypertrophy (BPH) by RT-PCR analysis. Expression profiles of PSA, PSMA, PSCA, PCTA, PTI-1, and PROSTASE were evaluated in four BPH specimens, two patient-derived prostate carcinomas, three cell lines derived from metastatic CaP (LNCaP, Du-145, PC3), and one cell line derived from carcinoma of bladder (T 24). Expression of PAP, PSGR and STEAP was examined in two additional BPH and three additional CaP specimens (a total of six BPHs and five CaPs). To verify the validity of cDNA samples, expression of the house-keeping gene glyceraldehyde phosphate dehydrogenase (GAPDH) in the same cDNA samples was tested. The results showed that GAPDH represented similar input RNA (data not shown).

Five antigens, namely PSA, PSMA, PAP, STEAP and PSGR have been defined as the most suitable candidates for immunotherapy of CaP based on over-expression in most CaP samples compared to BPH (FIGS. 11A-11E).

Selected five antigens were screened for candidate TAA peptides predicted to bind HLA-A2.1 molecules. These analyses were performed by computer software, through a world wide web interface (www-bimas.dcrt.nih.gov/molbio/hla_bind/index.html). This software scores every possible peptide along the sequence for MHC binding, when every amino acid in the evaluated peptide is scored according to its contribution to the binding. This calculation is based on data of natural MHC peptides, and of experiments with peptide libraries-binding to HLA-A2.1 molecules. The analysis of the sequences gave the peptide sequences as the highest expected binders (Table 5).

TABLE 5

Amino acid sequence of peptides from PAP, PSA, PSMA, PSGR and STEAP proteins, predicted to bind HLA-A2.1 molecule:

| Peptide Designation | Start Position | Peptide Sequence | SEQ ID NO: |
|---|---|---|---|
| PSMA-1 | 663 | MMNDQLMFL | SEQ ID NO: 29 |
| PSMA-2 | 711 | ALFDIESKV | SEQ ID NO: 30 |
| PSMA-3 | 4 | LLHETDSAV | SEQ ID NO: 31 |
| PSMA-4 | 27 | VLAGGFFLL | SEQ ID NO: 32 |
| PSMA-5 | 26 | LVLAGGFFL | SEQ ID NO: 33 |
| PSA-1 | 7 | FLTLSVTWI | SEQ ID NO: 34 |
| PSA-2 | 170 | KLQCVDLHV | SEQ ID NO: 35 |
| PSA-3 | 52 | GVLVHPQWV | SEQ ID NO: 36 |
| PSA-4 | 53 | VLVHPQWVL | SEQ ID NO: 37 |
| PSA-5 | 195 | FMLCAGRWT | SEQ ID NO: 38 |
| STEAP-1 | 165 | GLLSFFFAV | SEQ ID NO: 39 |
| STEAP-2 | 86 | FLYTLLREV | SEQ ID NO: 40 |
| STEAP-3 | 262 | LLLGTIHAL | SEQ ID NO: 41 |
| STEAP-4 | 303 | LIFKSILFL | SEQ ID NO: 42 |
| STEAP-5 | 158 | MLTRKQFGL | SEQ ID NO: 43 |
| PAP-1 | 18 | FLFLLFFWL | SEQ ID NO: 44 |
| PAP-2 | 30 | VLAKELKFV | SEQ ID NO: 45 |
| PAP-3 | 135 | ILLWQPIPV | SEQ ID NO: 46 |
| PAP-4 | 13 | SLSLGFLFL | SEQ ID NO: 47 |
| PAP-5 | 112 | TLMSAMTNL | SEQ ID NO: 48 |
| PSGR-1 | 202 | ILLVMGVDV | SEQ ID NO: 49 |
| PSGR-2 | 152 | SLFFFPLPL | SEQ ID NO: 50 |
| PSGR-3 | 59 | YLFLCMLAA | SEQ ID NO: 51 |
| PSGR-4 | 205 | VMGVDVMFI | SEQ ID NO: 52 |
| PSGR-5 | 274 | VMGDIYLLL | SEQ ID NO: 53 |
| PSGR-6 | 18 | GLEKAHFWV | SEQ ID NO: 54 |
| PSGR-7 | 302 | VLAMFKISC | SEQ ID NO: 55 |

Peptide binding to MHC was evaluated by loading on HLA-A2.1-transfected RMA-S cells (RMA-S-HHD) and monitoring MHC stabilization. RMA-S cells are murine TAP deficient cells with a defect in peptide transport and presentation. RMA-S cells present low levels of class I MHC molecules, which are peptide free and therefore unstable. Loaded peptide can stabilize the MHC molecules, and can be monitored by staining for MHC. A high degree of correlation between predicted and actual binding has been confirmed by FACS analysis (FIGS. 12A-12L).

Figure 13A:
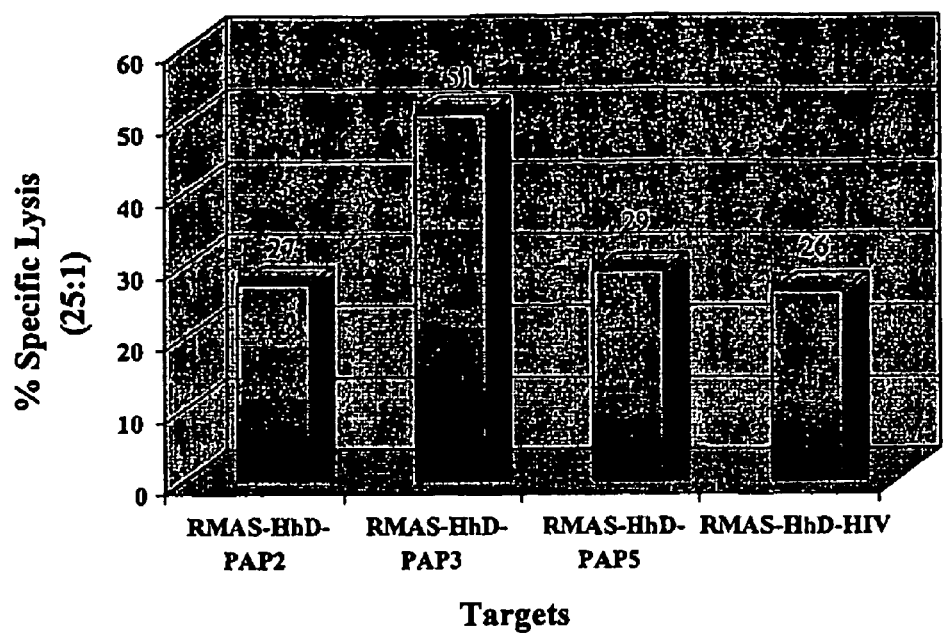
FIGS. 13A and 13B are graphs showing immunogenicity of PAP- or STEAP-derived peptides in HHD mice. The mice were immunized i.v. one time with $1 \times 10^6$ peptide-loaded syngeneic dendritic cells (DCs). The DCs were loaded separately with individual peptides, washed and pooled before immunization. Spleens were removed on day 10, and splenocytes were re-stimulated in vitro by 100 μM PAP-derived (FIG. 13A) or STEAP-derived (FIG. 13B) peptides in OPTI-MEM for 2 h at 37° C., 5% $CO_2$, followed by restimulation of lymphocytes for 4 more days in RPMI-HEPES, as described. CTL assays were performed on day 5 with individual PAP-, STEAP-derived peptides loaded on RMAS-HHD-B7.1 as targets. Non-relevant HIV derived peptide-loaded RMAS-HHD-B7.1 cells were used as negative controls. The effector-to-target ratio of 25:1 is shown.
Figure 13B:
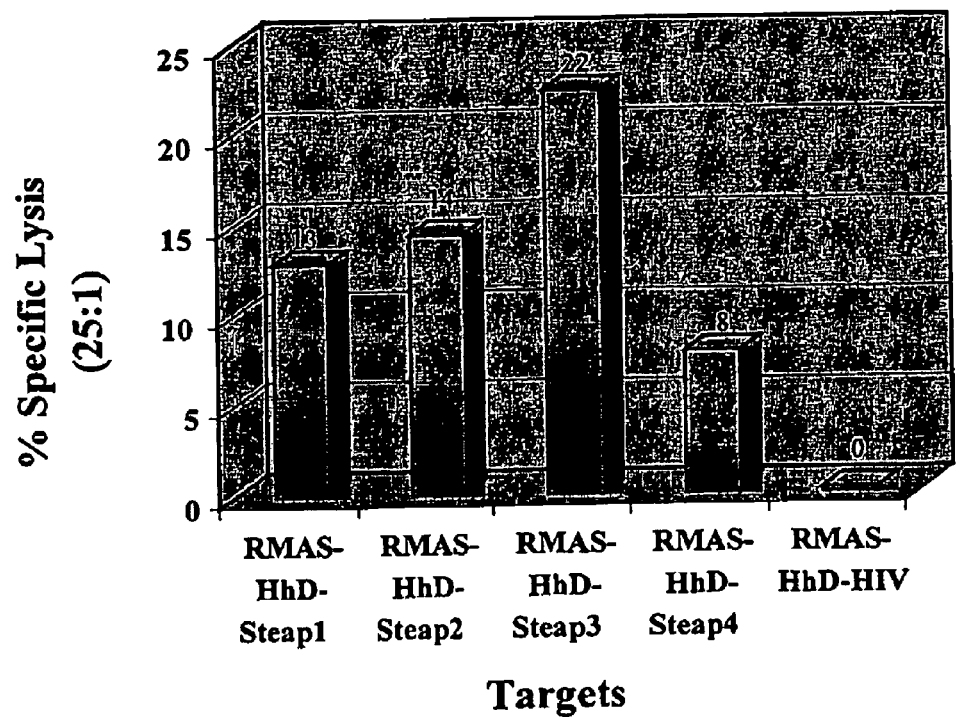
Figure 14A:
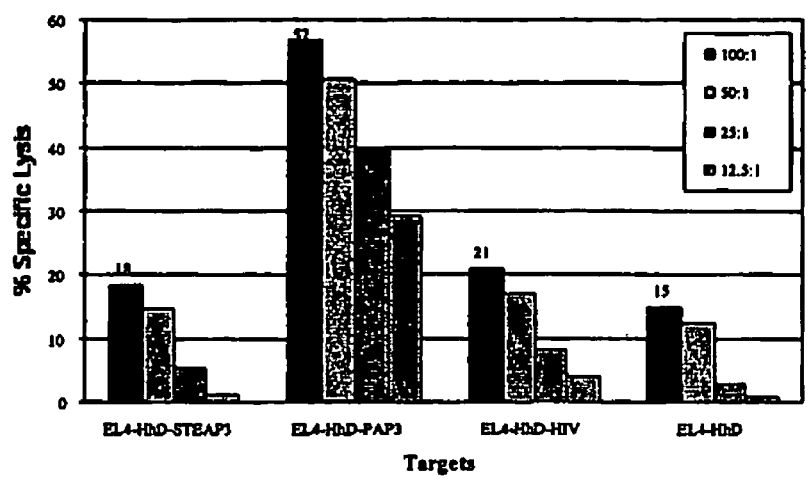
FIGS. 14A and 14B are graphs showing immunogenicity of PAP-3 (FIG. 14A) and STEAP-3 (FIG. 14B) peptides in HHD mice. Mice immunized i.p. three times at 7-day intervals, with $2 \times 10^6$ irradiated (5000 rad) were single peptide-loaded (PAP-3 for FIG. 14A, STEAP-3 for FIG. 14B) TAP-2 deficient RMAS-HHD-B7.1 cells. Spleens were removed on day 10, and splenocytes were restimulated in vitro by 100 μM PAP-3 or STEAP-3 peptides in OPTIMEM for 2 h at 37° C., 5% $CO_2$, followed by restimulation of lymphocytes for 4 more days in RPMI-HEPES, as described. CTL assays were performed on day 5 with PAP-3 or STEAP-3 loaded on EL4-HHD as targets. Unloaded EL4-HHD or non-relevant HIV derived peptide-loaded EL4-HHD cells were used as negative controls. The effector-to-target ratios of 100:1; 50:1; 25:1; 12.5:1 are shown.
Figure 14B:
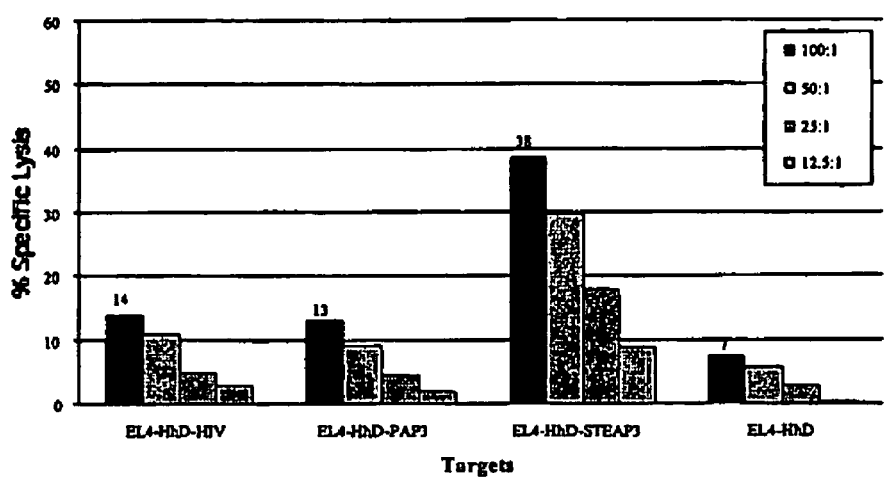
Figure 15A:
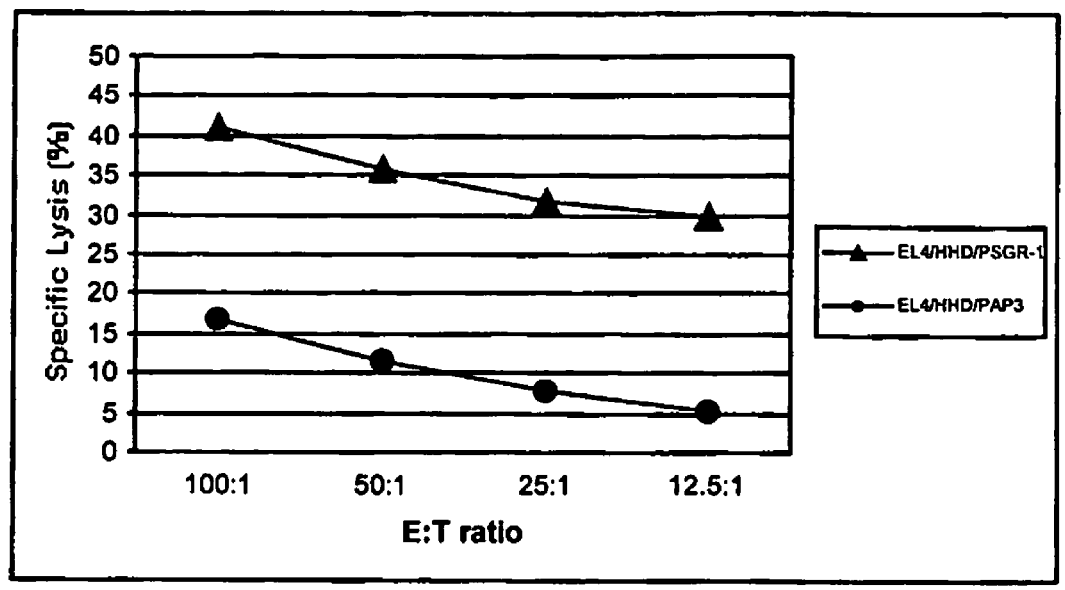
FIGS. 15A and 15B are graphs showing immunogenicty of PSGR-derived peptides in HHD mice. The mice were immunized i.v. three time with $1 \times 10^6$ syngeneic dendritic cells (DCs) loaded with either PSGR-1 or PSGR-6 peptides. Spleens were removed on day 10 after the last immunization, and splenocytes were re-stimulated in vitro by 100 μM PSGR-1 (FIG. 15A) or PSGR-6 (FIG. 15B) derived peptides in OPTIMEM for 2 h at 37° C., 5% $CO_2$, followed by restimulation of lymphocytes for 4 more days in RPMI-HEPES. CTL assays were performed on day 5 with individual PSGR-1 or PSGR-6 derived peptides loaded on EL4/HHD cells as targets. Non-relevant PAP derived peptide-loaded EL4/HHD cells were used as negative controls. 100:1, 50:1, 25:1, 12.5:1 effector-to-target ratios are shown.
Figure 15B:
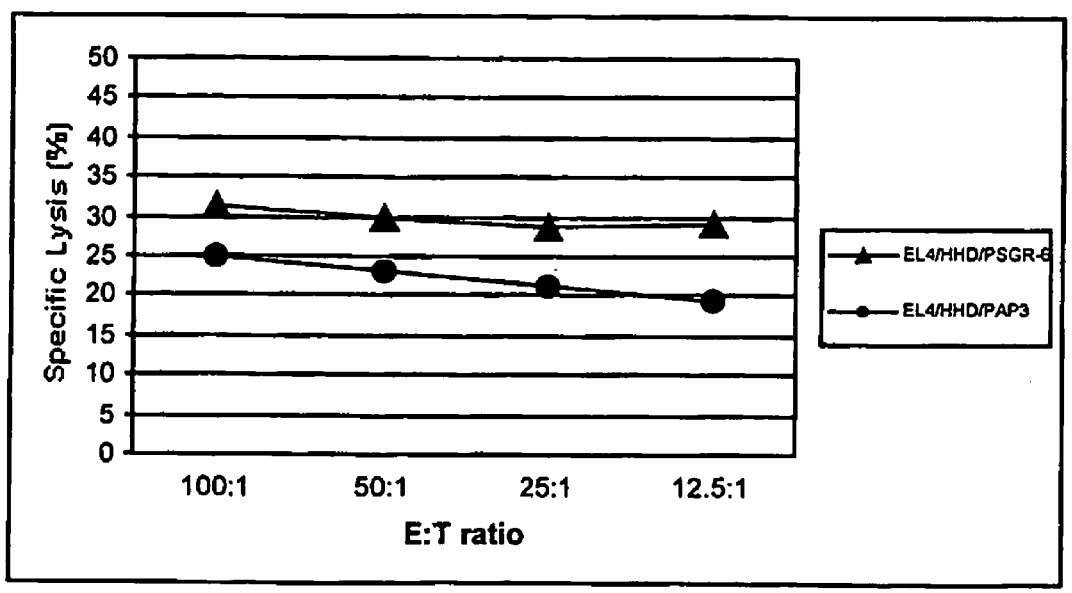

The immunogenicity of the peptides, namely their potential to induce T cell responses, was subsequently examined in an in vivo model. A strain of β2 microglobulin (β2m) HLA-A2.1 Monochain Transgenic, H-2D$^{b-/-}$Xβ2m$^{-/-}$ double knockout mice (HHD mice) was used. Upon vaccination of these mice, a repertoire of human HLA-A2.1 restricted CTLs is produced. The lysis patterns of each of the individual peptides loaded on target cells were first evaluated following immunization with syngeneic dendritic cells pulsed with pools of 2-4 synthetic peptides derived from each examined protein. CTL results showed significant lysis of RMAS-HHD-B7.1 target cells loaded either with the PAP-derived peptide 3 (PAP-3; SEQ ID NO:46) or with STEAP-derived peptide 3 (STEAP-3; SEQ ID NO:41) while other peptides showed either only background levels (PAP-, PSA-, PSMA-derived peptides) or much less effective lysis (STEAP-derived peptides) (FIGS. 13A and 13B). Immunization of HHD mice with single PAP-3- or STEAP-3-loaded RMAS-HHD-B7.1 cells showed remarkable and dose-dependent lysis of EL-4-HHD target cells loaded with the PAP-3 or STEAP-3, respectively (FIGS. 14A and 14B). Unlike PAP and STEAP antigens, where only the PAP-3 and STEAP-3 peptides have been shown to be immunogenic in HHD mice, all the peptides derived from PSGR antigen showed different levels of immunogenicity: from low of PSGR-6 to higher of PSGR-1-5 and 7 (FIGS. 15A and 15B).

Finally, peripheral blood of two healthy (donors B, C) and one CaP (donor A) individuals were tested for the existence of CTL precursors (FIGS. 16A-16D). Leukopheresis products of the donors were obtained from Barzilai Medical Center (Ashkelon, Israel) according to Declaration of Helsinki Principles. PBMC were isolated by centrifugation on Ficoll-Plaque Plus gradients (Amersham, Sweden). In vitro priming of CTL was done over autologous DC that were prepared from monocytes by IL-4 and GM-CSF treatment and maturated with a IL-1β, IL-6, TNF-α and PGE$_2$ cocktail. DC were pulsed with synthetic peptides and PBMC were supplemented with IL-7. Two days later, IL-2 was added and renewed every three days. Two additional re-stimulations were done every 7 days over peptide pulsed monocytes. Seven days after the third stimulation, lymphocytes were harvested and a cytolytic assay was performed using relevant/non-relevant peptide pulsed or non-pulsed at all T2 cells.

Figures 16A, 16B:
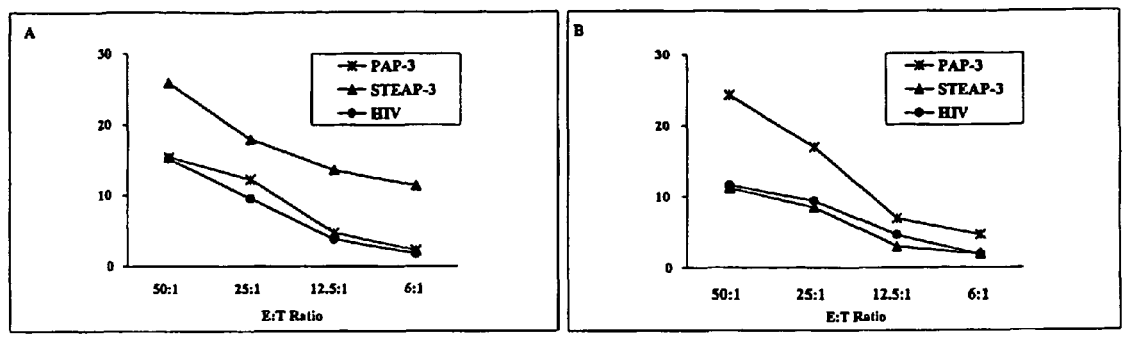
FIGS. 16A-16D are graphs showing in vitro priming of human CTLs. PBMC of leukopheresis samples were isolated and in vitro CTL primed with peptide pulsed autologous DC. PBMC were supplemented with IL-7 and two days later IL-2 was added and renewed every three days. Additional two cycles of re-stimulation were done every 7 days over peptide pulsed monocytes. Seven days after the last stimulation cytolytic assay was performed using peptide pulsed or non-pulsed T2 cells as target.
Figures 16C, 16D:
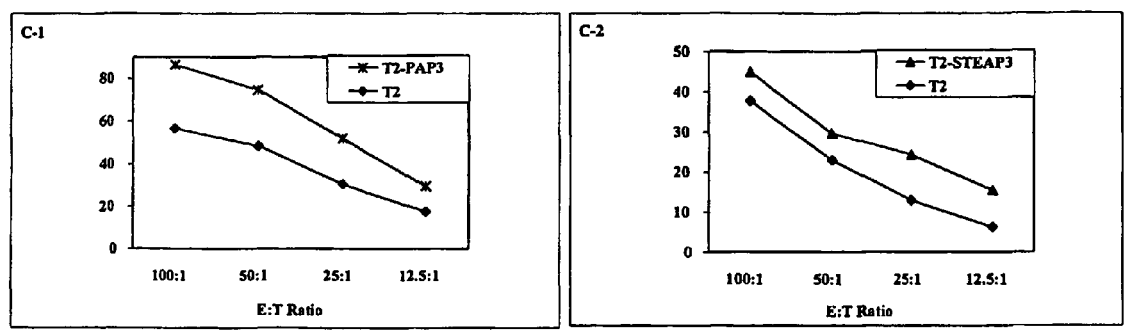

As can be seen in FIGS. 16B and 16C, PAP-3 peptide was immunogenic in both healthy donors giving specific lysis over the background level, whereas STEAP-3 peptide has activated CTL precursors in PBMC derived from CaP individual (FIG. 16A) as well as from one of the healthy donors (FIG. 16D, C-2).

In this study, the HHD model was shown to be an effective biological tool for screening of putative novel peptides as well as for assessment of their ability to elicit powerful antitumor CTL response. Prostatic Acid Phosphatase (PAP) derived peptide 3 (PAP-3; SEQ ID NO:46), Six-Transmembrane Epithelial Antigen of Prostate (STEAP) derived peptide 3 (STEAP-3; SEQ ID NO:41) as well as PSGR derived peptides (PSGR 1-7; SEQ ID NOs: 49-55) were shown to be immunogenic in HHD mice. Importantly, testing the peripheral blood of healthy individuals has shown the existence of peripheral CTL precursors for peptide PAP-3 (2 out of 2 donors) and for peptide STEAP-3 (1 out of 2 donors) peptides. In addition, peptide STEAP-3 has activated peripheral CTL precursors in PBMC derived from CaP individual.

The Immunogenicity of Peptides from Overexpressed Genes in Human PBMC

Figure 17A:
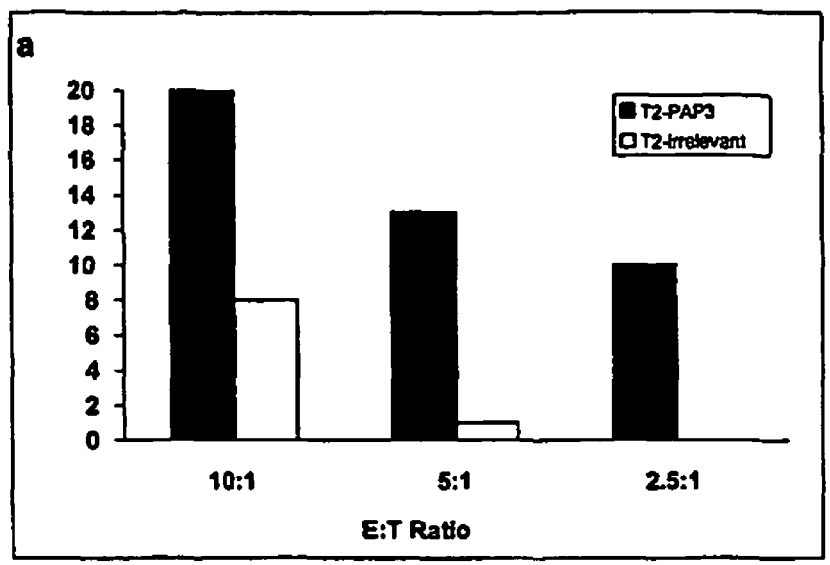
FIGS. 17A-17C are graphs showing peptide specific CTL induced in human PBMC by PAP-3 (FIG. 17A), STEAP-3 (FIG. 17B), and PSGR-1 (FIG. 17C). PBMC from a healthy donor were stimulated by peptide pulsed DC as described and CTL activity was tested on homologous peptide pulsed T2 target cells (HLA-A2 lymphoma, TAP deficient).
Figure 17B:
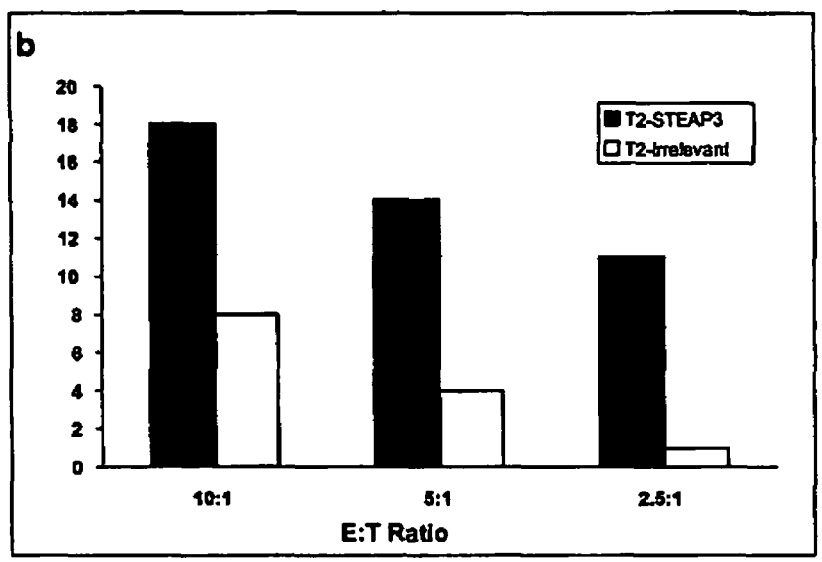
Figure 17C:
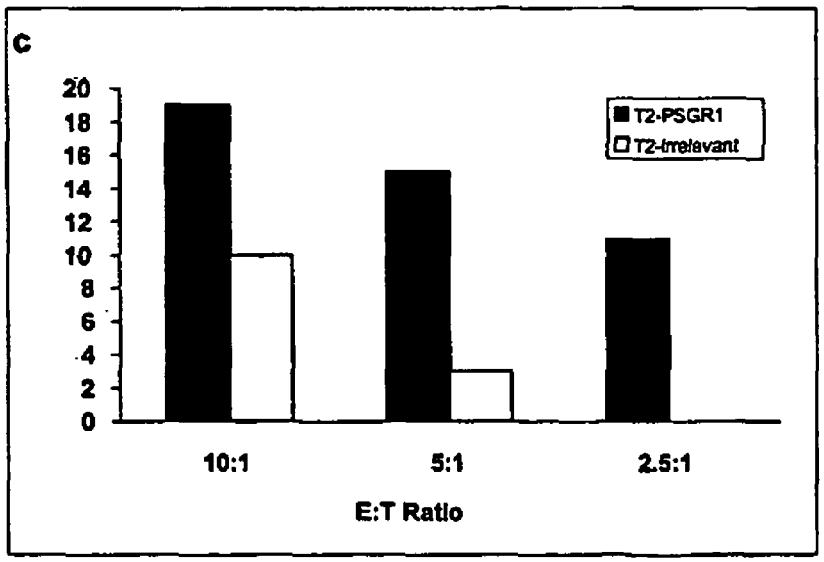
Figure 18A:
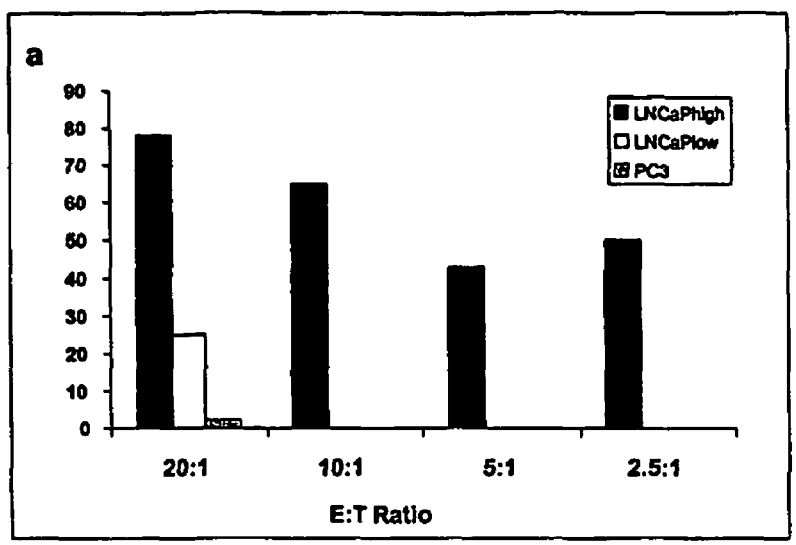
FIGS. 18A-18E are graphs showing that human anti-peptide CTL from a healthy donor kills LNCaP tumor cells. PBMC from a healthy donor (FIGS. 18A-18C) or a CaP patient (FIGS. 18D-18E) were stimulated with PAP-3 (FIGS. 18A, 18D), STEAP-3 (FIGS. 18B, 18E) or PSGR-1 (FIG. 18C) as described. LNCaP/CRL1740 (LNCaP high in HLA-A2.1 expression), LNCaP/CRL10995 (LNCaP low in HLA-A2.1 expression) and PC3 (negative for HLA-A2.1) served as targets in CTL assays.
Figure 18B:
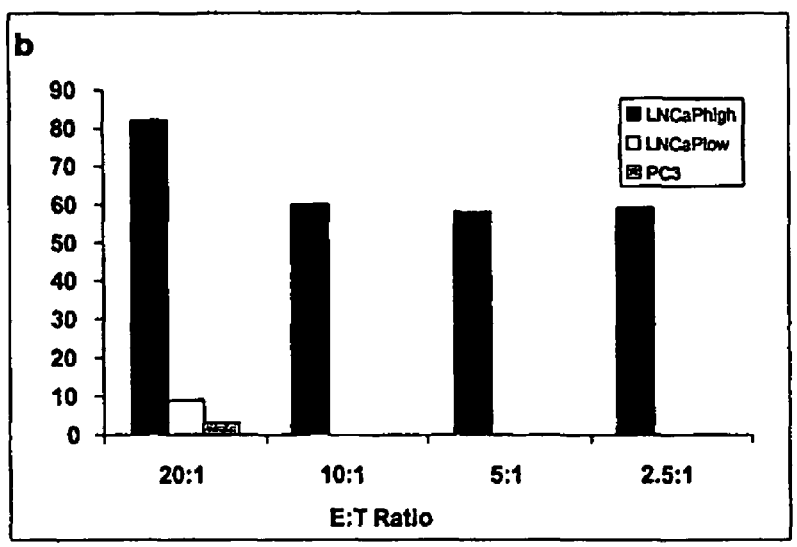
Figure 18C:
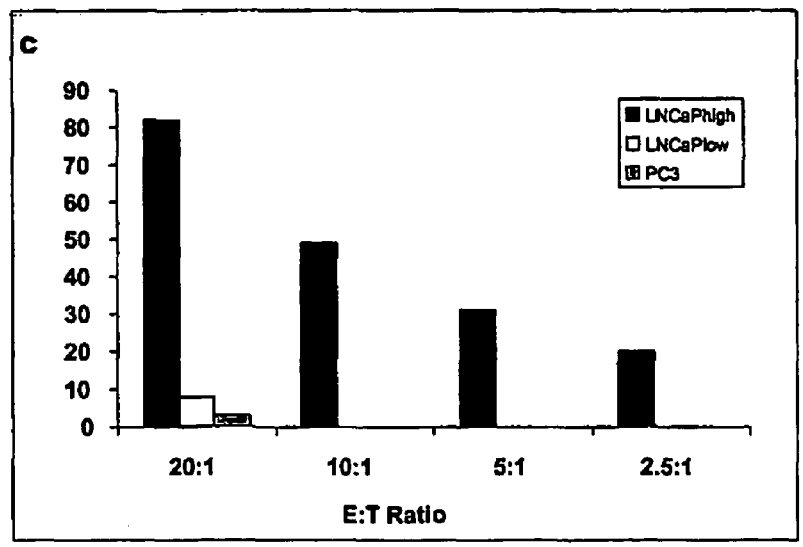
Figure 18D:
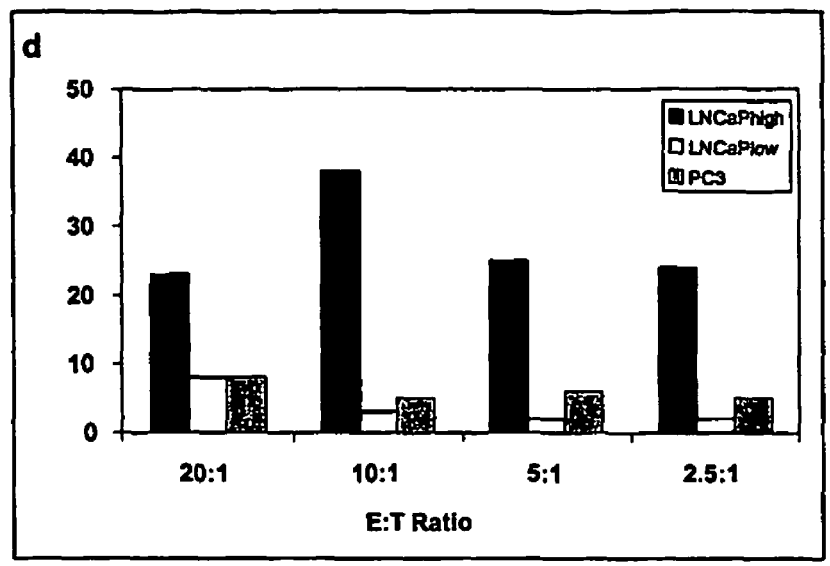
Figure 18E:
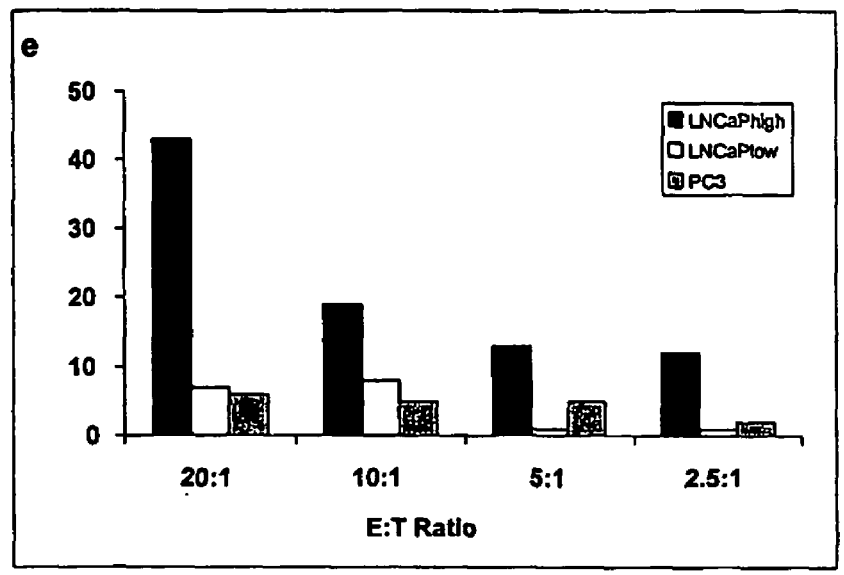

When human PBMC are stimulated in vitro by PAP-3 and STEAP-3 peptides, the resulting CTL can lyse target cells (T2, EL4/HHD) pulsed with PAP-3, STEAP-3 or PSGR-1 and PSGR-6 peptides. (FIGS. 15 and 16). Here, these findings were expanded and peripheral blood of three healthy and two CaP individuals was tested for the existence of CTL precursors against PAP-3, STEAP-3 and PSGR-1 peptides. Leukopheresis products of the donors were obtained from Barzilai Medical Center (Ashkelon, Israel) according to Declaration of Helsinki Principles. PBMC were isolated by centrifugation on Ficoll-Plaque Plus gradients (Amersham, Sweden). In vitro priming of CTL was done over autologous DC that were prepared from monocytes by IL-4 and GM-CSF treatment and matured with a IL-1β, IL-6, TNF-α and PGE2 cocktail. DC were pulsed with synthetic peptides and PBMC were supplemented with IL-7. Two days later, IL-2 was added and renewed every three days. Two additional re-stimulations were done every 7 days over peptide pulsed monocytes. Seven days after the third stimulation, lymphocytes were harvested and a cytolytic assay was performed using relevant/non-relevant peptide pulsed or non-pulsed T2 cells (FIGS. 17A-17C) and LNCaP (high and low HLA expressors) cells as targets (FIGS. 18A-18E). PAP-3, STEAP-3 and PSGR-1 activated CTL precursors in PBMC derived from CaP patients and healthy donors. These CTL are of high affinity since they lyse tumor cells that express endogenously processed proteins at physiological concentrations. Monitoring of HLA-A2-peptide specific CD8+ cells for PAP-3 and STEAP-3 was also performed by MHC-peptide tetramers (tetramers of recombinant HLA-A2.1-beta2 microglobulin single chain with peptides were prepared in collaboration with Dr Yoram Reiter, Technion, Haifa). Levels of 1.7% for PAP-3 and 0.76% for STEAP-3 were found in stimulated PBMC indicating specific priming and expansion of specific CTL populations (not shown).

Rejection of PC3-HHD by Adoptive Transfer of Anti Peptide CTL

Figure 19A:
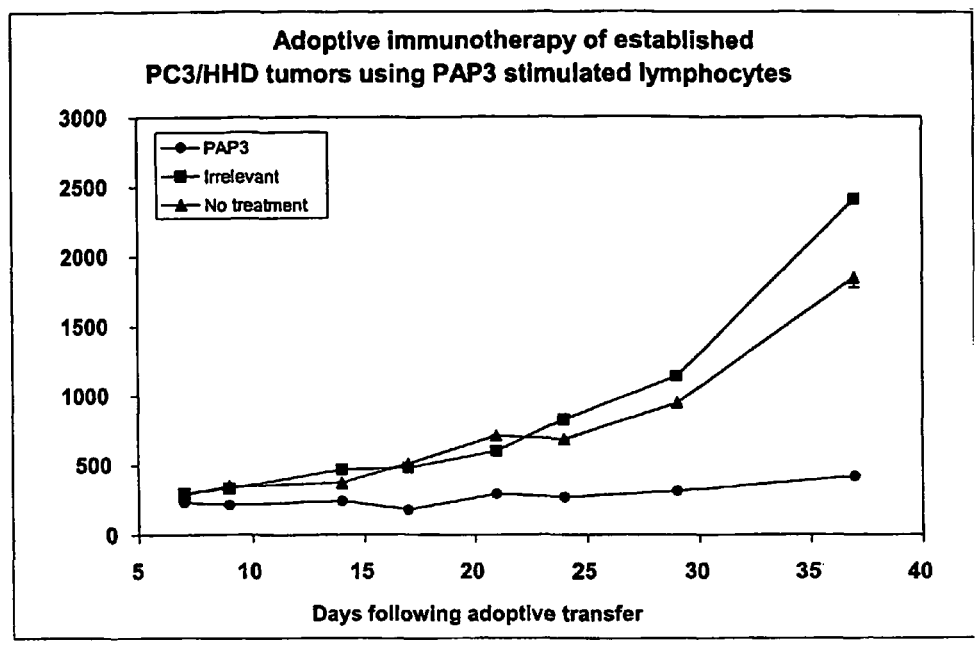
FIGS. 19A and 19B are graphs showing that adoptively transferred anti-peptide CTL retard tumor growth. HHD derived anti-PAP3 (FIG. 19A) or STEAP-3 (FIG. 19B) were stimulated in vitro and transferred to CD1 nude mice bearing 7 day PC3-HHD tumors (expressing PAP and STEAP) as described. Tumor growth was followed for 38 days.
Figure 19B:
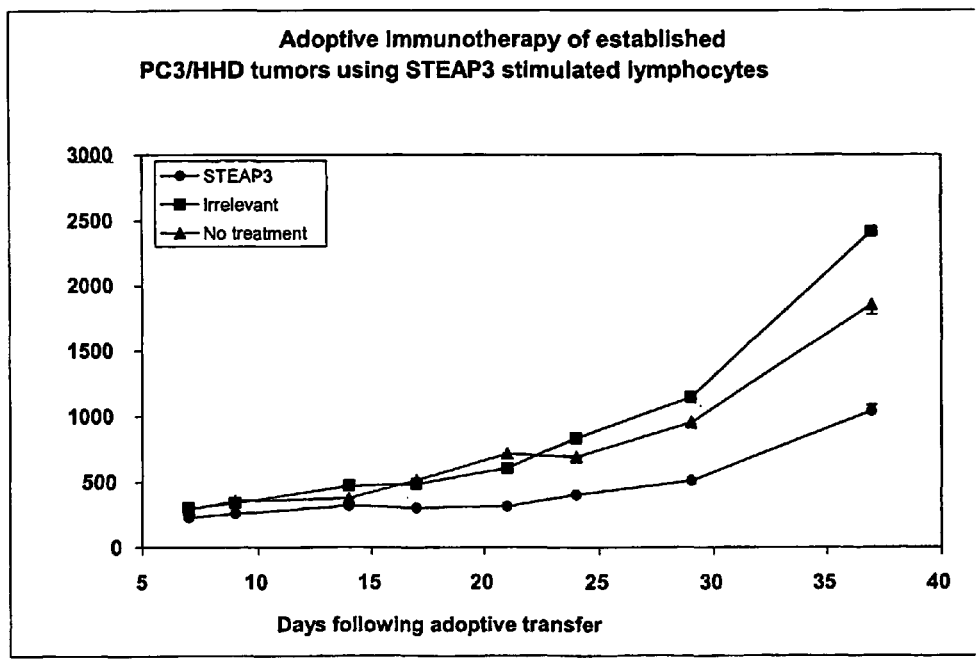

HHD mice were immunized i.p. 6 times (twice at week) with $10^6$ syngeneic dendritic cells pulsed with either PAP-3, STEAP-3 or irrelevant (tyrosinase-derived, HLA-A2.1 binding) peptides. Spleens were removed on day 10, and splenocytes were restimulated in vitro by 100 µM of either PAP-3 or STEAP-3 peptides in OPTIMEM for 2 h at 37° C., 5% $CO_2$, followed by restimulation of lymphocytes for 4 more days in lymphocyte medium (RPMI-1640 supplemented with 25 mM HEPES, 10% heat-inactivated FCS, 0.1 mM non-essential amino acids, 1 mM sodium pyruvate, 2 mM. L-glutamine, 40 microg/ml garamycin and $5\times10^{-5}$ M 2-mercaptoethanol). Total lymphocytes were suspended at $10^6$/ml and activated with plate-bound anti-CD3 mAb (145-2C11) for 72 h at 37° C. in 5% $CO_2$ in 24-well plates. Activated cells were resuspended at a concentration of $3\times10^5$/ml lymphocyte medium with IL-2 (100 U/ml) for 3 days, then diluted 1:3 in fresh medium with IL-2 for an additional 4 days. Lymphocytes were harvested, samples were incubated with anti-CD4, anti-CD8 or isotype control mAb (all obtained from Catalog, USA), and analyzed using CellQuest software. Seven to nine CD1 nude mice per group received 4 Gy total body irradiation from a 137CS source, followed by s.c. inoculation with $5\times10^6$ PC3-HHD13 cells in Matrigel (BD PharMingen, San Diego, Calif.) to initiate tumors. Seven days later, mice were injected locally with $35\times10^6$ PAP-3 or tyrosinase specific lymphocytes ($11\times10^6$ were CD8+), $50\times10^6$ STEAP-3 specific lymphocytes ($3\times10^6$ were CD8+) or PBS. IL-2 (1000 U) was injected twice a day for five consecutive days. Tumor size was measured 3 times per week. Anti-PAP-3 CTL caused complete rejection of tumors in 4/8 mice and retarded growth in the others, while the lower CD8+ dose of anti-STEAP-3 CTL caused complete rejection of tumors in 2/3 mice and retarded growth in the others (FIGS. 19A-19B).

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, sequence database accession numbers, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by references.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Abeloff, M. D. Breast Cancer. *Current Opinion in Oncology* 8, 447-448 (1996)

Acres, R. B., Hareuveni, M., Balloul, J.-M. and Kieny, M.-P. Vaccinia virus MUC1 immunization of mice: immune response and protection against the growth of murine tumors bearing the MUC1 antigen. *J Immunother* 14, 136-143 (1993)

Andriole, G. L. Adjuvant therapy for prostate cancer patients at high risk of recurrence following radical prostatectomy. *Eur Urol* Supp 3; 65-69 (1997)

Bakker, A., Schreurs, M., deBoer, A., Kawakami, Y., Rosenberg, S., Adema, G. Boring, C. C., Squires, T. S., Tong, T., Montgomery, S., *Cancer Res* 59, 676-683 (1999)

Barber L D, Percival L, Arnett K L, Gumperz J E, Chen L, Parham Polymorphism in the alpha 1 helix of the HLA-B heavy chain can have an overriding influence on peptide-binding specificity. *J Immunol* 158(4):1660-9 (1997)

Barra, C., Gournier, H., Garcia, Z., Marche, P. N., Jouvin-Marche, E., Briand, P., Fillipi, P. and Lemonnier, F. A. Abrogation of H-2-restricted CTL responses and efficient recognition of HLA-A3 molecules in DBA/2 HLA/A24 responder mice. *J Immunol* 150, 3681-3689 (1993)

Behr et al., Radioimmunotherapy of small-volume disease of metastatic colorectal cancer. *American Cancer Society*, 1373-1381 (2002)

Better et al, "*Escherichia coli* secretion of an active chimeric antibody fragment", *Science* 240:1041-1043 (1988)

Blake, J., Johnston, J., Hellstrom, K. E., Marquardt, H. and Chen, L. Use of combinatorial peptide libraries to construct functional mimics of tumor epitopes recognized by MHC class I restricted T lymphocytes. *J exp Med* 184, 121-130 (1996)

Boczkowski, D., Nair, S. K., Snyder, D. and Gilboa, E., Dendritic cells pulsed with RNA are potent antigen-presenting cells in vitro and in vivo. *J Exp Med* 184, 465-472 (1996)

Boon, T. and van der Bruggen, P. Human tumor antigens recognized by T lymphocytes. *J Exp Med* 183, 725-729 (1996)

Boon, T., Cerottini, J.-C., Van den Eynde, B., Van der Bruggen, P. and Van Pel, A. Tumor antigens recognized by T lymphocytes. *Annu Rev Immunol* 12, 337-365 (1994)

Boulianne et al, "Production of functional chimaeric mouse/human antibody", *Nature* 312:643-646 (1984)

Brichard V, Van Pel A, Wolfel T, Wolfel C, De Plaen E, Lethe B, Coulie P, Boon T. The tyrosinase gene codes for an antigen recognized by autologous cytolytic T lymphocytes on HLA-A2 melanomas. *J Exp Med* 178(2):489-95 (1993)

Brichard V G, Herman J, Van Pel A, Wildmann C, Gaugler B, Wolfel T, Boon T, Lethe B. A tyrosinase nonapeptide presented by HLA-B44 is recognized on a human melanoma by autologous cytolytic T lymphocytes. *Eur J Immunol* 26(1):224-30 (1996)

Brossart P, Heinrich K S, Stuhler G, Behnke L, Reichardt V L, Stevanovic S, Muhm A, Rammensee H G, Kanz L, Brugger W. Identification of HLA-A2-restricted T-cell epitopes derived from the MUC1 tumor antigen for broadly applicable vaccine therapies. *Blood* 93(12):4309-17 (1999)

Brossart, P. et al. Her-2/neu-derived peptides are tumor-associated antigens expressed by human renal cell and colon carcinoma lines and are recognized by in vitro induced specific cytotoxic T lymphocytes. *Cancer Res* 58, 732-736 (1998)

Byrne, R. L., Autzen, P., Birch, P., Robinson, M. C., Gullick, W. J., et al. The Immunohistochemical Detection of Cripto-1 in Benign and Malignant Human Bladder. *J Pathol* 185:108 (1998)

Cabilly et al, "Generation of antibody activity from immunoglobulin polypeptide chains produced in *Escherichia coli*", *Proc Natl Acad Sci USA* 81:3273-3277 (1984)

Carmon L, El-Shami K M, Paz A, Pascolo S, Tzehoval E, Tirosh B, Koren R, Feldman M, Fridkin M, Lemonnier F A, Eisenbach L. Novel breast-tumor-associated MUC1-derived peptides: characterization in Db−/−xbeta2 microglobulin (beta2m) null mice transgenic for a chimeric HLA-A2.1/Db-beta2 microglobulin single chain. *Int J Cancer* 85(3):391-7 (2000)

Carmon, L. et al. Novel breast-tumor-associated MUC1-derived peptides: characterization in Db−/−xbeta2 microglobulin (beta2m) null mice transgenic for a chimeric HLA-A2.1/Db-beta2 microglobulin single chain. *Int J Cancer* 85, 391-397 (2000)

Castelli C, Storkus W J, Maeurer M J, Martin D M, Huang E C, Pramanik B N, Nagabhushan T L, Parmiani G, Lotze M T. Mass spectrometric identification of a naturally processed melanoma peptide recognized by CD8+ cytotoxic T lymphocytes. *J Exp Med* 181(1):363-8 (1995)

Castelli C, Tarsini P, Mazzocchi A, Rini F, Rivoltini L, Ravagnani F, Gallino F, Belli F, Parmiani G. Novel HLA-Cw8-restricted T cell epitopes derived from tyrosinase-related protein-2 and gp100 melanoma antigens. *J Immunol* 162 (3):1739-48 (1999)

Cayeux, S., Ricter, G., Noffz, G., Dorken, B. and Blankenstein, T. Influence of gene-modified (IL-7, IL-4, and B7) tumor cell vaccines on tumor antigen presentation. *J Immunol*, 158:2834-41 (1997)

Celis E, Tsai V, Crimi C, DeMars R, Wentworth P A, Chesnut R W, Grey H M, Sette A, Serra H M. Induction of anti-tumor cytotoxic T lymphocytes in normal humans using primary cultures and synthetic peptide epitopes. *Proc Natl Acad Sci USA* 91(6):2105-9 (1994)

Chaux P, Luiten R, Demotte N, Vantomme V, Stroobant V, Traversari C, Russo V, Schultz E, Cornelis G R, Boon T, van der Bruggen P. dentification of five MAGE-A1 epitopes recognized by cytolytic T lymphocytes obtained by in vitro stimulation with dendritic cells transduced with MAGE-A1. *J Immunol* 163(5):2928-36 (1999)

Chames et al., Direct selection of a human antibody fragment directed against the tumor T-cell epitope HLA-A1-MAGE-A1 from a nonimmunized phage-Fab library. *PNAS*, 97(14) 7969-7974 (2000)

Chen, W., Yewdell, J. W., Levine, R. L. & Bennink, J. R. Modification of cysteine residues in vitro and in vivo affects the immunogenicity and antigenicity of major histocompatibility complex class I-restricted viral determinants. *J Exp Med* 189, 1757-1764 (1999).

Ciccodicola, A., Dono, R., Obici, S., Simeone, A., Zollo, M., and Persico, M. G. (1989) Molecular characterization of a gene of the 'EGF family' expressed in undifferentiated human NTERA2 teratocarcinoma cells. *EMBO J* 8, (1987)

Clave, E., Carosella, E. D., Gluckman, E. & Socie, G. Radiation-enhanced expression of interferon-inducible genes in the KG1a primitive hematopoietic cell line. *Leukemia* 11, 114-119 (1997)

Colligan et al, *Current Protocols in Immunology*, Green Publishing Assoc., and Wiley Interscience, New York (2002)

Conry, R. M., LoBuglio, A. F., Kantor, J., Schlom, J., Loechel, F., Moore, S. E., Sumerel, L. A., Barlow, D. L., Abrams, S. and Curiel, D. T., Immune response to a carcinoembryonic antigen polynucleotide vaccine. *Cancer Res*, 54, 1164-1168 (1994)

Conry, R. M., LoBuglio, A. F., Loechel, F., Moore, S. E., Sumerel, L. A., Barlow, D. L., Pike, J. and Curiel, D. T. A carcinoembryonic antigen polynucleotide vaccine for human clinical use. *Cancer Gene Therapy* 2:33-38 (1995)

Coulie P G, Brichard V, Van Pel A, Wolfel T, Schneider J, Traversari C, Mattei S, De Plaen E, Lurquin C, Szikora J P, et al. A new gene coding for a differentiation antigen recognized by autologous cytolytic T lymphocytes on HLA-A2 melanomas. *J Exp Med* 180(1):35-42 (1994)

Cox A L, Skipper J, Chen Y, Henderson R A, Darrow T L, Shabanowitz J, Engelhard V H, Hunt D F, Slingluff C L Jr. Identification of a peptide recognized by five melanoma-specific human cytotoxic T cell lines. *Science* 264(5159):716-9 (1994)

Cox, A., Skipper, J., Chen, Y., Henderson, R., Darrow, T., Shabanowitz, J., Engelhard, V., Hunt, D. and Slingluff, C. Identification of a peptide recognized by five melanoma-specific human cytotoxic T cell lines. *Science* 264:716-719 (1994)

Daido, H., Zhou, M. & Gomez-Sanchez, C. E. Angiotensin stimulates the expression of interferon-inducible genes in H295R cells. *Mol Cell Endocrinol* 176, 21-27 (2001).

De Plaen, E. et al. Identification of genes-coding for tumor antigens recognized by cytolytic T lymphocytes. *Methods* 12:125-142. (1997)

Deblandre, G. A. et al. Expression cloning of an interferon-inducible 17-kDa membrane protein implicated in the control of cell growth. *J Biol Chem* 270:23860-23866 (1995)

DeRisi, J. et al. Use of a cDNA microarray to analyse gene expression patterns in human cancer. *Nat Genet* 14:457-460 (1996)

Domenech N, Henderson R A, Finn O J. Identification of an HLA-A11-restricted epitope from the tandem repeat domain of the epithelial tumor antigen mucin. *J Immunol* 155(10):4766-74 (1995)

Eisenbach, L., Bar-Haim, E. & El-Shami, K. Antitumor vaccination using peptide based vaccines. *Immunol Lett* 74:27-34 (2000)

Engelhard V H. Structure of peptides associated with MHC class I molecules. *Curr Opin Immunol* 6(1):13-23 (1994)

Eshhar et al, "Chimeric T cell receptor which incorporates the anti-tumour specificity of a monoclonal antibody with the cytolytic activity of T cells: a model system for immunotherapeutical approach", *Br J Cancer Suppl*, 10:27-29 (1990)

Fearon, E. R., Pardoll, D. M., Itaya, T., Golumbek, P., Levitsky, H. I., Simons, J. W., Karasuyama, H., Vogelstein, B., and Frost, P. Interleukin-2 production by tumor cells by passes T helper function in generation of an anti-tumor response. *Cell* 60:397-403 (1990)

Feltkamp, M., Smits, H. L., Vierboom, M., Minnaar, R. P., dejough, B. M., Drijfhout, J. W., Schegget, J., Melief, C. J. M. and Kast, W. M. Vaccination with cytotoxic T lymphocyte epitope-containing peptide protects against a tumor induced by human papillomavirus type 16-transformed cells. *Eur J Immunol* 23: 2242-2249 (1993)

Fidler, I. J. and Balch, C. M. The biology of cancer metastasis and implications for therapy. *Curr. Progr. Surg.* 24, 137-209 (1987)

Figdor, C. Melanocyte lineage-specific antigen gp100 is recognized by melanoma-derived tumor-infiltrating lymphocytes. *J Exp Med* 179:1005-1009 (1994)

Fiorillo M T, Meadows L, D'Amato M, Shabanowitz J, Hunt D F, Appella E, Sorrentino R. Susceptibility to ankylosing spondylitis correlates with the C-terminal residue of peptides presented by various HLA-B27 subtypes. *Eur J Immunol* 27(2):368-73 (1997)

Firat, H. et al. H-2 class I knockout, HLA-A2.1-transgenic mice: a versatile animal model for preclinical evaluation of antitumor immunotherapeutic strategies. *Eur J Immunol* 29:3112-3121 (1999).

Fishman et al., Autoantibodies to tyrosinase: The bridge between melanoma and vitiligo. *American Cancer Socitey*, 1461-1464 (1997)

Fisk B, Hudson J M, Kavanagh J, Wharton J T, Murray J L, Ioannides C G, Kudelka A P. Existent proliferative responses of peripheral blood mononuclear cells from healthy donors and ovarian cancer patients to HER-2 peptides. *Anticancer Res* 17(1A):45-53 (1997)

Fisk B, Savary C, Hudson J M, O'Brian C A, Murray J L, Wharton J T, Ioannides C G. Changes in an HER-2 peptide upregulating HLA-A2 expression affect both conformational epitopes and CTL recognition: implications for optimization of antigen presentation and tumor-specific CTL induction. *J Immunother Emphasis Tumor Immunol* 18(4):197-209 (1995)

Fleischhauer K, Tanzarella S, Russo V, Sensi M L, van der Bruggen P, Bordignon C, Traversari C. Functional heterogeneity of HLA-A*02 subtypes revealed by presentation of a MAGE-3-encoded peptide to cytotoxic T cell clones. *J Immunol* 159(5):2513-21 (1997)

Fleischhauer K, Tanzarella S, Wallny H J, Bordignon C, Traversari C. Multiple HLA-A alleles can present an immunodominant peptide of the human melanoma antigen Melan-A/MART-1 to a peptide-specific HLA-A*0201+ cytotoxic T cell line. *J Immunol* 157(2):787-97 (1996)

Fong, L., C. L. Ruegg, D. Brockstedt, E. G. Engleman and R. Laus. Induction of tissue-specific autoimmune prostatitis with prostatic acid phosphatase immunization: implications for immunotherapy of prostate cancer. *J Immunol* 159:3113-7 (1997)

Freiss, H., Yamanaka, Y., Buchler, M., Korbin, M. S., et al. Cripto, A Member of The Epidermal Growth Factor Family, is Over Expressed in Human Pancreatic Cancer and Chronic Pancreatitis. *Int J Cancer* 56:688 (1994)

Fujie T, Tahara K, Tanaka F, Mori M, Takesako K, Akiyoshi T. A MAGE-1-encoded HLA-A24-binding synthetic peptide induces specific anti-tumor cytotoxic T lymphocytes. *Int J Cancer* 80(2):169-72 (1999)

Gaugler B, Van den Eynde B, van der Bruggen P, Romero P, Gaforio J J, De Plaen E, Lethe B, Brasseur F, Boon T. Human gene MAGE-3 codes for an antigen recognized on a melanoma by autologous cytolytic T lymphocytes. *J Exp Med* 179(3):921-30 (1994)

Gjertsen, M. K., Bakka, A., Breivik, J., Saeterdal, I., Gedde-Dahl, Stokke, K. T., Solheim, B. G., Egge, T. S., Soreide, O., Thorsby, E., and Gaudernack, G., Ex vivo ras peptide vaccination in patients with advanced pancreatic cancer: results of a phase I/II study. *Int J Cancer* 65: 450-453 (1996)

Govorko et al., Single-chain antibody against the common epitope of mutant p53:isolation and intracytosolic expression in mammalian cells. *Journal of Immunological Methods*, 258:169-181 (2001)

Gress, T. M. et al. A pancreatic cancer-specific expression profile. *Oncogene* 13:1819-1830 (1996)

Gross et al, "Expression of immunoglobulin-T-cell receptor chimeric molecules as functional receptors with antibody-type specificity", *Proc Natl Acad Sci USA*, 86:10024-10028 (1989)

Harlow et al, *Antibodies: A Laboratory Manual*, Cold Spring Harbor Laboratory, Cold Spring Harbor, N.Y. (1988)

Herman J, van der Bruggen P, Luescher I F, Mandruzzato S, Romero P, Thonnard J, Fleischhauer K, Boon T, Coulie P G. A peptide encoded by the human MAGE3 gene and presented by HLA-B44 induces cytolytic T lymphocytes that recognize tumor cells expressing MAGE3. *Immunogenetics* 43(6):377-83 (1996)

Hisamatsu, T. et al. Interferon-inducible gene family 1-8U expression in colitis-associated colon cancer and severely inflamed mucosa in ulcerative colitis. *Cancer Res* 59:5927-5931 (1999)

Huang et al., Antibody responses to melanoma/melanocyte autoantigens in melanoma patients. *The Society for Investigative Dermatology, Inc.*, 662-667 (1998)

Hubert, R. S., I. Vivanco, E. Chen, S. Rastegar, K. Leong, S. C. Mitchell, R. Madraswala, Y. Zhou, J. Kuo, A. B. Raitano, A. Jakobovits, D. C. Saffran and D. E. Afar. STEAP: a prostate-specific cell-surface antigen highly expressed in human prostate tumors. *Proc Natl Acad Sci USA*. 96: 14523-8 (1999).

Jager et al., Humoral immune responses of cancer patients against "cancer-testis" antigen NY-ESO-1: correlation with clinical events. *Int J Cancer (Pred Oncol)*, 84:506-510 (1999)

Jager E, Chen Y T, Drijfhout J W, Karbach J, Ringhoffer M, Jager D, Arand M, Wada H, Noguchi Y, Stockert E, Old L J, Knuth A. Simultaneous humoral and cellular immune response against cancer-testis antigen NY-ESO-1: definition of human histocompatibility leukocyte antigen (HLA)-A2-binding peptide epitopes. *J Exp Med* 187(2): 265-70 (1998)

Kang X, Kawakami Y, el-Gamil M, Wang R, Sakaguchi K, Yannelli J R, Appella E, Rosenberg S A, Robbins P F. Identification of a tyrosinase epitope recognized by HLA-A24-restricted, tumor-infiltrating lymphocytes. *J Immunol* 155(3):1343-8 (1995)

Kass, E. et al. Induction of protective host immunity to carcinoembryonic antigen (CEA), a self-antigen in CEA transgenic mice, by immunizing with a recombinant vaccinia-CEA virus. *Cancer Res* 59:676-683 (1999)

Kast W M, Roux L, Curren J, Blom H J, Voordouw A C, Meloen R H, Kolakofsky D, Melief C J. Protection against lethal Sendai virus infection by in vivo priming of virus-specific cytotoxic T lymphocytes with a free synthetic peptide. *Proc Natl Acad Sci USA* 88(6):2283-7 (1991)

Kast, W. M., Brandt, R. M. P., Sidney, J., Drijfhout, J. W., Kubo, R. T., Melief, C. J. M. and Sette, A. Role of HLA-A motifs in identification of potential CTL epitopes in human papillomavirus type 16 E6 and E7 proteins. *J Immunol* 152: 3904-3912 (1994)

Kawakami Y, Eliyahu S, Delgado C H, Robbins P F, Rivoltini L, Topalian S L, Miki T, Rosenberg S A. Cloning of the gene coding for a shared human melanoma antigen recognized by autologous T cells infiltrating into tumor. *Proc Natl Acad Sci USA* 91(9):3515-9 (1994)

Kawakami Y, Eliyahu S, Jennings C, Sakaguchi K, Kang X, Southwood S, Robbins P F, Sette A, Appella E, Rosenberg S A. Recognition of multiple epitopes in the human melanoma antigen gp100 by tumor-infiltrating T lymphocytes associated with in vivo tumor regression. *J Immunol* 154 (8):3961-8 (1995)

Kawakami Y, Eliyahu S, Sakaguchi K, Robbins P F, Rivoltini L, Yannelli J R, Appella E, Rosenberg S A. dentification of the immunodominant peptides of the MART-1 human melanoma antigen recognized by the majority of HLA-A2-restricted tumor infiltrating lymphocytes. *J Exp Med* 1:180 (1):347-52 (1994)

Kawakami Y, Robbins P F, Wang X, Tupesis J P, Parkhurst M R, Kang X, Sakaguchi K, Appella E, Rosenberg S A. Identification of new melanoma epitopes on melanosomal proteins recognized by tumor infiltrating T lymphocytes restricted by HLA-A1, -A2, and -A3 alleles. *J Immunol* 161(12):6985-92 (1998)

Kawashima I, Hudson S J, Tsai V, Southwood S, Takesako K, Appella E, Sette A, Celis E. The multi-epitope approach for immunotherapy for cancer: identification of several CTL epitopes from various tumor-associated antigens expressed on solid epithelial tumors. *Hum Immunol* 59(1): 1-14 (1998)

Kawashima I, Tsai V, Southwood S, Takesako K, Celis E, Sette A. Identification of gp100-derived, melanoma-specific cytotoxic T-lymphocyte epitopes restricted by HLA-A3 supertype molecules by primary in vitro immunization with peptide-pulsed dendritic cells. *Int J Cancer* 78(4): 518-24 (1998)

Kawashima I, Tsai V, Southwood S, Takesako K, Sette A, Celis E. Identification of HLA-A3-restricted cytotoxic T lymphocyte epitopes from carcinoembryonic antigen and HER-2/neu by primary in vitro immunization with peptide-pulsed dendritic cells. *Cancer Res* 59(2):431-5 (1999)

Kedar, E. and Klein, E. Cancer Immunotherapy: Are the results discouraging? Can they be improved? *Adv Immunol* 58:245-322 (1995)

Kim C, Matsumura M, Saijo K, Ohno T. In vitro induction of HLA-A2402-restricted and carcinoembryonic-antigen-specific cytotoxic T lymphocytes on fixed autologous peripheral blood cells. *Cancer Immunol Immunother* 47(2):90-6 (1998)

Kittlesen D J, Thompson L W, Gulden P H, Skipper J C, Colella T A, Shabanowitz J, Hunt D F, Engelhard V H, Slingluff C L Jr, Shabanowitz J A. Human melanoma patients recognize an HLA-A1-restricted CTL epitope from tyrosinase containing two cysteine residues: implications for tumor vaccine development. *J Immunol* 160(5): 2099-106 (1998)

Kohler et al, "Continuous cultures of fused cells secreting antibody of predefined specificity", *Nature* 256:495-497 (1975)

Kono K, Rongcun Y, Charo J, Ichihara F, Celis E, Sette A, Appella E, Sekikawa T, Matsumoto Y, Kiessling R. Identification of HER2/neu-derived peptide epitopes recognized by gastric cancer-specific cytotoxic T lymphocytes. *Int J Cancer* 78(2):202-8 (1998)

Kuniyasu, H., Yoshida, K., Yokoazaki, H., et al. Expression of Cripto, a Novel Gene of the Epidermal Growth Factor Family, in Human Gastrointestinal Carcinomas. *Jpn J Cancer Res* 82:969 (1991)

Lev, A. Denkberg, G., Cohen, Cyril J., Tzukerman, Maty, Skorecki, Karl L., Chames, Patrick, Hoogenboom, Hennie R., Reiter, Yoram, Isolation and characterization of human recombinant antibodies endowed with the antigen-specific, major histocompatibility complex-restricted specificity of T cells directed toward the widely expressed tumor T-cell epitopes of the telomerase catalytic subunit, *Cancer Research*, 62:3184-3194 (2002)

Lewin, A. R., Reid, L. E., McMahon, M., Stark, G. R. & Kerr, I. M. Molecular analysis of a human interferon-inducible gene family. *Eur J Biochem* 199:417-423 (1991)

Lindblom, A. Different mechanisms in the tumorigenesis of proximal and distal colon cancers. *Curr Opin Oncol* 13: 63-69 (2001)

Liu et al, "Chimeric mouse-human IgG1 antibody that can mediate lysis of cancer cells" *Proc Natl Acad Sci USA* 84:3439-3443 (1987)

Luiten R, van der Bruggen P. A MAGE-A1 peptide is recognized on HLA-B7 human tumors by cytolytic T lymphocytes. *Tissue Antigens* 55(2):149-52 (2000)

Lustgarten J, Theobald M, Labadie C, LaFace D, Peterson P, Disis M L, Cheever M A, Sherman L A. Identification of Her-2/Neu CTL epitopes using double transgenic mice expressing HLA-A2.1 and human CD.8. *Hum Immunol* 52(2):109-18 (1997)

Mandelboim, O., Berke, G., Fridkin, M., Feldman, M., Eisenstein, M., and Eisenbach, L., CTL induction by a tumor-associated antigen octapeptide derived from a murine lung carcinoma. *Nature* 369:67-71 (1994)

Mandelboim, O., Vadai, E., Fridkin, M., Katz-Hillel, A., Feldman, M., Berke, G. and Eisenbach, L. Regression of established murine carcinoma metastases following vaccination with tumor-associated antigen. *Nature Med* 1:1179-1183 (1995)

Marchand, M., Weynants, P., Rankin, E., Arienti, F., Belli, F., Parmiani, G., Cascinelli, N., Bourland, A., Wanwijck, R., Humblet, Y., Canon, J. L., Naeyaert, J. M., Plagne, R., Deraemaeker, R., Knuth, A., Jager, E., Brasseur, F., Herman, J., Coulie, P. G. and Boon, T. *Int. J. Cancer* 63:883-885 (1995)

Mayordomo, J. I., Zorina, T., Storkus, W. J., Zitvogel, L., Celluzzi, C., Falo, L. D., Melief, C. J., Ildstad, S. T., Kast, W. M., Deleo, A. B., et al., Bone marrow-derived dendritic cells pulsed with synthetic tumor peptides elicit protective and therapeutic antitumor immunity. *Nature Med* 1:1297-1302 (1995)

Meidenbauer, N., D. T. Harris, L. E. Spitler and T. L. Whiteside. Generation of PSA-reactive effector cells after vaccination with a PSA-based vaccine in patients with prostate cancer. *Prostate* 43:88-100 (2000).

Melief, C. J. et al. Strategies for immunotherapy of cancer. *Adv Immunol* 75:235-282 (2000)

Minev, B. et al. Cytotoxic T cell immunity against telomerase reverse transcriptase in humans. *Proc Natl Acad Sci USA* 97:4796-4801 (2000)

Moase et al., Anti-MUC-1 immunoliposomal doxorubicin in the treatment of murine models of metastatic breast cancer. *Bioochimica et Biophysica Acta* 1510:43-55 (2001)

Morrison et al, "Chimeric human antibody molecules: mouse antigen-binding domains with human constant region domains". *Proc Natl Acad Sci USA* 81:6851-6855 (1984)

Mukherji, B., Chakraborty, N. G., Yamasaki, S., Okino, T., Yamase, H., Sporn, J. R., Kurtzman, S. K., Ergin, M. T., Ozols, J., Meehan, J., et al., Induction of antigen-specific cytolytic T cells in situ in human melanoma by immunization with synthetic peptide-pulsed autologous antigen presenting cells. *Proc Natl Acad Sci USA* 92:8078-8082 (1995)

Murphy, G., Tjoa, B., Ragde, H., Kenny, G. and Boynton, A., Phase I clinical trial: T-cell therapy for prostate cancer using autologous dendritic cells pulsed with HLA-A0201-specific peptide from prostate-specific membrane antigen. *Prostate* 29:371-380 (1996.)

Nagorsen, D. et al. Natural T-cell response against MHC class I epitopes of epithelial cell adhesion molecule, her-2/neu, and carcinoembryonic antigen in patients with colorectal cancer. *Cancer Res* 60:4850-4854 (2000)

Nelson, P. S., L. Gan, C. Ferguson, P. Moss, R. Gelinas, L. Hood and K. Wang. Molecular cloning and characterization of prostase, an androgen-regulated serine protease with prostate-restricted expression. *Proc Natl Acad Sci USA* 96:3114-9 (1999)

Nestlel, F. L., Alijagic, S., Gillietl, M., Sun, Y., Grabbe, S., Dummerl, R., Burge, G. and Schadendorf, D. Vaccination of melanoma patients with peptide or tumor lysate-pulsed dendritic cells. *Nature Med* 4:328-332 (1998)

Neuberger et al, "A hapten-specific chimaeric IgE antibody with human physiological effector function", *Nature* 314: 268-270 (1985)

Niethammer et al., An oral DNA vaccine against human carcinoembryonic antigen (CEA) prevents growth and dissemination of Lewis lung carcinoma in CEA transgenic mice. *Vaccine* 20:421-429 (2002)

Noppen C, Levy F, Burri L, Zajac P, Remmel E, Schaefer C, Luscher U. Heberer M, Spagnoli G C. Naturally processed and concealed HLA-A2.1-restricted epitopes from tumor-associated antigen tyrosinase-related protein-2. *Int J Cancer* 87(2):241-6 (2000)

Nseyo, U. O. and Lamm, D. L. Immunotherapy of bladder cancer. *Semin Surg Oncol* 13:342-349 (1997)

Nukaya I, Yasumoto M, Iwasaki T, Ideno M, Sette A, Celis E, Takesako K, Kato I. Identification of HLA-A24 epitope peptides of carcinoembryonic antigen which induce tumor-reactive cytotoxic T lymphocyte. *Int J Cancer* 80(1):92-7 (1999)

Offringa, R., van der Burg, S. H., Ossendorp, F., Toes, R. E. & Melief, C. J. Design and evaluation of antigen-specific vaccination strategies against cancer. *Curr Opin Immunol* 12:576-582 (2000)

Oiso M, Eura M, Katsura F, Takiguchi M, Sobao Y, Masuyama K, Nakashima M, Itoh K, Ishikawa T. A newly identified M AGE-3-derived epitope recognized by HLA-A24-restricted cytotoxic T lymphocytes. *Int J Cancer* 81(3):387-94 (1999)

Okamoto et al., Anti-tyrosinase-related protein-2 immune response in vitiligo patients and melanoma patients receiving active-specific immunotherapy. *The Society for Investigative Dermatology, Inc.,* 1034-1039 (1998)

Pardoll, D. M. New strategies for enhancing the immunogenicity of tumors. *Curr. Opinion Immunol.* 5:719-725 (1993)

Pardoll, D. M. Cancer vaccines: a road map for the next decade. *Curr Opinion Immunol* 8:619-621 (1996)

Parker, K. C., Bednarek, M. A. & Coligan, J. E. Scheme for ranking potential HLA-A2 binding peptides based on independent binding of individual peptide side-chains. *J Immunol* 152:163-175 (1994)

Parkhurst M R, Fitzgerald E B, Southwood S, Sette A, Rosenberg S A, Kawakami Y. Identification of a shared HLA-A*0201-restricted T-cell epitope from the melanoma antigen tyrosinase-related protein 2 (TRP2). *Cancer Res* 58(21):4895-901 (1998)

Pascolo S, Schirle M, Guckel B, Dumrese T, Stumm S, Kayser S, Moris A, Wallwiener D, Rammensee H G, Stevanovic S. A M AGE-A1 HLA-A A*0201 epitope identified by mass spectrometry. *Cancer Res* 61(10):4072-7 (2001)

Pascolo, S. et al. HLA-A2.1-restricted education and cytolytic activity of CD8(+) T lymphocytes from beta2 microglobulin (beta2m) HLA-A2.1 monochain transgenic H-2Db beta2m double knockout mice. *J Exp Med* 185: 2043-2051 (1997)

Peiper M, Goedegebuure P S, Linehan D C, Ganguly E, Douville C C, Eberlein T J. The HER2/neu-derived peptide p654-662 is a tumor-associated antigen in human pancreatic cancer recognized by cytotoxic T lymphocytes. *Eur J Immunol* 27(5):1115-23 (1997)

postolopoulos V, Karanikas V, Haurum J S, McKenzie I F. nduction of HLA-A2-restricted CTLs to the mucin 1 human breast cancer antigen. *J Immunol* 159(11):5211-8 (1997)

Qi, C. F., Liscia, D. S., Normano, N., Merlo, G., Johnson, G. R., Gullick, W. J., Ciardiello, F., Saeki, T., Brandt, R., Kim, N., Kenney, N., and Salomon, D. S. Expression of Transforming Growth Factor A, Amphiregulin and Cripto-I in Human Breast Carcinomas. *Br J Cancer,* 69:903 (1994)

Qin, Z. and Blankenstein, T. Influence of local cytokines on tumor metastasis: using cytokine gene transfected tumor cells as experimental models. In "Attempts to Understand Metastasis Formation III", Therapeutic Approaches for Metastasis Treatment, Current Topics in *Microbiology and Immunology* (U. Gunlhert, P. M. Schlag and W. Birchmeier, eds.) 213III, 55-64 (1996)

Raddishe et al., Anti-MUC1 class I restricted CTLs in metastatic breast cancer patients immunized with a synthetic MUC1 peptide. *Int J Cancer,* 76:817-823 (1998)

Rammensee, H.-G., Falk, K. and Rotzschke, O. Peptides naturally presented by MHC class I molecules. *Annu Rev Immunol* 11:213-244 (1993)

Reiter, R. E., Z. Gu, T. Watabe, G. Thomas, K. Szigeti, E. Davis, M. Wahl, S. Nisitani, J. Yamashiro, M. M. Le Beau, M. Loda and O. N. Witte. Prostate stem cell antigen: a cell surface marker overexpressed in prostate cancer. *Proc Natl Acad Sci USA* 95:1735-40 (1998)

Rivoltini L, Kawakami Y, Sakaguchi K, Southwood S, Sette A, Robbins P F, Marincola F M, Salgaller M L, Yannelli J R, Appella E, et al. Induction of tumor-reactive CTL from peripheral blood and tumor-infiltrating lymphocytes of melanoma patients by in vitro stimulation with an immunodominant peptide of the human melanoma antigen MART-1. *J Immunol* 154(5):2257-65 (1995)

Robbins P F, el-Gamil M, Kawakami Y, Stevens E, Yannelli J R, Rosenberg S A. Recognition of tyrosinase by tumor-infiltrating lymphocytes from a patient responding to immunotherapy. *Cancer Res* 54(12):3124-6 (1994)

Rongcun Y, Salazar-Onfray F, Charo J, Malmberg K J, Evrin K, Maes H, Kono K, Hising C, Petersson M, Larsson O, Lan L, Appella E, Sette A, Celis E, Kiessling R. Identification of new HER2/neu-derived peptide epitopes that can elicit specific CTL against autologous and allogeneic carcinomas and melanomas. *J Immunol* 163(2):1037-44 (1999)

Rosenberg, S. A. et al. Immunologic and therapeutic evaluation of a synthetic peptide vaccine for the treatment of patients with metastatic melanoma. *Nature Med* 4:321-327 (1998)

Saeki, T., Stromberg, K., Qi, C. F., et al. Differential Immunohistochemical Detection of Amphiregulin and Cripto in Human Normal Colon and Colorectal Cancers Tumours. *Cancer Res* 52:3467 (1992)

Sahagan et al, "A genetically engineered murine/human chimeric antibody retains specificity for human tumor-associated antigen" *J Immunol* 137:1066-1074 (1986)

Savoie, C. J. et al. MHC class I bound peptides of a colon carcinoma cell line, a Ki-ras gene-targeted progeny cell line and a B cell line. *Cancer Lett* 123:193-197 (1998)

Schirle M, Keilholz W, Weber B, Gouttefangeas C, Dumrese T, Becker H D, Stevanovic S, Rammensee H G. Identification of tumor-associated MHC class I ligands by a novel T cell-independent approach. *Eur J Immunol* 30(8):2216-25 (2000)

Schneider J, Brichard V, Boon T, Meyer zum Buschenfelde K H, Wolfel T. Overlapping peptides of melanocyte differentiation antigen Melan-A/M ART-1 recognized by autologous cytolytic T lymphocytes in association with HLA-B45.1 and HLA-A2.1. *Int J Cancer* 75(3):451-8 (1998)

Schultz E S, Zhang Y, Knowles R, Tine J, Traversari C, Boon T, van der Bruggen P. A MAGE-3 peptide recognized on HLA-B35 and HLA-A1 by cytolytic T lymphocytes. *Tissue Antigens* 57(2):103-9 (2001)

Severin, M. J. Genetic susceptibility for specific cancers. Medical liability of the clinician. *Cancer* 86, 2564-2569. (1999)

Shirai, M. et al. CTL responses of HLA-A2.1-transgenic mice specific for hepatitis C viral peptides predict epitopes for CTL of humans carrying HLA-A2.1. *J Immunol* 154:2733-2742 (1995)

Skipper J C, Hendrickson R C, Gulden P H, Brichard V, Van Pel A, Chen Y, Shabanowitz J, Wolfel T, Slingluff C L Jr, Boon T, Hunt D F, Engelhard V H. An HLA-A2-restricted tyrosinase antigen on melanoma cells results from post-translational modification and suggests a novel pathway for processing of membrane proteins. *J Exp Med* 183(2):527-34 (1996)

Skipper J C, Kittlesen D J, Hendrickson R C, Deacon D D, Harthun N L, Wagner S N, Hunt D F, Engelhard V H, Slingluff C L Jr. Shared epitopes for HLA-A3-restricted melanoma-reactive human CTL include a naturally processed epitope from Pmel-17/gp100. *J Immunol* 157(11):5027-33 (1996)

Spooner, R. A., Deonarain, M. P. and Epenetos, A. A., DNA vaccination for cancer treatment. *Gene Therapy* 2:173-180, (1995)

Su, Z. Z., J. Lin, R. Shen, P. E. Fisher, N. I. Goldstein and P. B. Fisher. Surface-epitope masking and expression cloning identifies the human prostate carcinoma tumor antigen gene PCTA-1 a member of the galectin gene family. *Proc Natl Acad Sci USA* 93:7252-7 (1996)

Sun Y, Song M, Stevanovic S, Jankowiak C, Paschen A, Rammensee H G, Schadendorf D. Identification of a new HLA-A(*)0201-restricted T-cell epitope from the tyrosinase-related protein 2 (TRβ2) melanoma antigen. *Int J Cancer* 87(3):399-404 (2000)

Sun et al, "Chimeric antibody with human constant regions and mouse variable regions directed against carcinoma-associated antigen 17-1A", *Proc Natl Acad Sci USA* 84:214-218 (1987)

Sun, Y., J. Lin, A. E. Katz and P. B. Fisher. Human prostatic carcinoma oncogene PTI-1 is expressed in human tumor cell lines and prostate carcinoma patient blood samples. *Cancer Res.* 57:18-23 (1997)

Tanaka F, Fujie T, Tahara K, Mori M, Takesako K, Sette A, Celis E, Akiyoshi T. Induction of antitumor cytotoxic T lymphocytes with a MAGE-3-encoded synthetic peptide presented by human leukocytes antigen-A24. *Cancer Res* 57(20):4465-8 (1997)

Theobald M, Biggs J, Hernandez J, Lustgarten J, Labadie C, Sherman L A. Tolerance to p53 by A2.1-restricted cytotoxic T lymphocytes. *J Exp Med* 185(5):833-41 (1997)

Thomson, S. A., Elliott, S. L., Sherritt, M. A., Sproat, K. W., Coupar, B. E., Scalzo, A. A., Forbes, C. A., Ladhams, A. M., Mo, X. Y., Tripp, R. A., Doherty, P. C., Moss, D. J. and Suhrbier, A., Recombinant polyepitope vaccines for the delivery of multiple CD8 cytotoxic T cell epitopes. *J Immunol* 157:822-826 (1996)

Thomson, S. A., Sherritt, M. A., Medveczky, J., Elliott, S. L., Moss, D. J., Fernando, G. J., Brown, L. E., and Suhrbier, A., Delivery of multiple CD8 cytotoxic T cell epitopes by DNA vaccination. *J Immunol* 160:1717-1723 (1998)

Tjoa, B. A., S. J. Simmons, A. Elgamal, M. Rogers, H. Ragde, G. M. Kenny, M. J. Troychak, A. L. Boynton and G. P. Murphy. Follow-up evaluation of a phase II prostate cancer vaccine trial. *Prostate* 40:125-9 (1999)

Townsend, A. and Bodmer, H. Antigen recognition by class I-restricted T lymphocytes. *Annu Rev Immunol* 7: 601-624 (1989)

Traversari C, van der Bruggen P, Luescher I F, Lurquin C, Chomez P, Van Pel A, De Plaen E, Amar-Costesec A, Boon T. A nonapeptide encoded by human gene MAGE-1 is recognized on HLA-A1 by cytolytic T lymphocytes directed against tumor antigen MZ2 E *J Exp Med* 176(5):1453-7 (1992)

Tsai V, Southwood S, Sidney J, Sakaguchi K, Kawakami Y, Appella E, Sette A, Celis E. Identification of subdominant CTL epitopes of the GP100 melanoma-associated tumor antigen by primary in vitro immunization with peptide-pulsed dendritic cells. *J Immunol* 158(4):1796-802 (1997)

Tsang K Y, Zaremba S, Nieroda C A, Zhu M Z, Hamilton J M, Schlom J. Generation of human cytotoxic T cells specific for human carcinoembryonic antigen epitopes from patients immunized with recombinant vaccinia-CEA vaccine. *J Natl Cancer Inst* 87(13):982-90 (1995)

Ullenhag et al., Induction of IgG subclass responses in colorectal caricinoma patients vaccinated with recombinant carcinoembryonic antigen. *Cancer Research,* 1364-1369 (2002)

Ulmer, J. B., Donnelly, J. J., Parker, S. E., Rhodes, G. H., Felgner, P. L., Dwaraki, V. J., Gromkowski, S. H., Deck, R. R., DeWitt, C. M., Friedman, A., Hawe, L. A., Leander, K. R., Martinez, D., Perry, H. C., Shiver, J. W., Montgomery, D. L. and Liu, M. A., Heterologous protection against influenza by injection of DNA encoding a viral protein. *Science* 259:1745-1749 (1993)

Urban, J. L. and Schreiber, H. Tumor antigens. *Annu Rev Immunol* 10:617-644 (1992)

Vaarala, M. H., Porvari, K., Kyllonen, A. & Vihko, P. Differentially expressed genes in two LNCaP prostate cancer cell lines reflecting changes during prostate cancer progression. *Lab Invest* 80:1259-1268 (2000)

van der Bruggen P, Bastin J, Gajewski T, Coulie P G, Boel P, De Smet C, Traversari C, Townsend A, Boon T. A peptide encoded by human gene MAGE-3 and presented by HLA-A2 induces cytolytic T lymphocytes that recognize tumor cells expressing MAGE-3. *Eur J Immunol* 24(12):3038-43 (1994)

Van Pel, A. and Boon, T. Protection against a nonimmunogenic mouse leukemia by an immunogenic variant obtained by mutagenesis. *Proc Natl Acad Sci US A* 79:4718-4722 (1982)

Vitiello, A., Marchesini, D., Furze, J., Sherman, L. A., Chestnut, R. W. (1991) Analysis of HLA restricted influenza specific cytotoxic T lymphocytes response in transgenic mice carrying a chimeric human-mouse class I major histocompatibility complex. *J Exp Med* 173:1007-1015 (1982)

Wentworth, P. A., Vitiello, A., Sidney, J., Keogh, E., Chesnut, R. W., Grey, H. and Sette, A. Differences and similarities in the A2.1-restricted cytotoxic T cell repertoire in humans and human leukocyte antigen-transgenic mice. *Eur J Immunol* 26:97-101 (1996)

Whitton, J. L., Sheng, N., Oldstone, M. B. and McKee, T. A., A "string-of-beads" vaccine, comprising linked minigenes, confers protection from lethal-dose virus challenge. *J Virol* 67:348-352 (1993)

Wolfel T, Van Pel A, Brichard V, Schneider J, Seliger B, Meyer zum Buschenfelde K H, Boon T. Two tyrosinase nonapeptides recognized on HLA-A2 melanomas by autologous cytolytic T lymphocytes. *Eur J Immunol* 24(3): 759-64 (1994)

Xu, L. L et all. PSGR, a novel prostate-specific gene with homology to a G protein-coupled receptor, is overexpressed in prostate cancer. *Cancer Res* 60:6568-6572 (2000)

Yip et al., Anti-ErbB-2 monoclonal antibodies and ErbB-2-directed vaccines. *Cancer Immunol Immunother,* 50:569-587 (2002)

Yu Z, Liu X, McCarty T M, Diamond D J, Ellenhorn J D. The use of transgenic mice to generate high affinity p53 specific cytolytic T cells. *J Surg Res* 69(2):337-43 (1997)

Zhang Q J, Gavioli R, Klein G, Masucci M G. An HLA-A11-specific motif in nonamer peptides derived from viral and cellular proteins. *Proc Natl Acad Sci USA* 90(6):2217-21 (1993)

Zhang, L. et al. Gene expression profiles in normal and cancer cells. *Science* 276:1268-1272 (1997)

Zhu, M. Z., Marshall, J., Cole, D., Schlom, J. & Tsang, K. Y. Specific cytolytic T-cell responses to human CEA from patients immunized with recombinant avipox-CEA vaccine. *Clin Cancer Res* 6:24-33 (2000)

What is claimed is:

1. An isolated tumor associated antigen (TAA) peptide of eight to ten amino acid residues, which is capable of promoting effective binding to a MHC class I molecule to elicit a CTL response and which is encoded by a polynucleotide overexpressed in human colon carcinoma cells, selected from the group consisting of the amino acid sequence of SEQ ID NO:27, SEQ ID NO:11; SEQ ID NO:25, SEQ ID NO:16, SEQ ID NO:20, SEQ ID NO:21 and SEQ ID NO:22.

2. The peptide of claim 1 which has the amino acid sequence of SEQ ID NO:27.

3. The peptide of claim 1 which has the amino acid sequence of SEQ ID NO:11.

4. The peptide of claim 1 which has the amino acid sequence of SEQ ID NO:25.

5. The peptide of claim 1, which has the amino acid sequence of SEQ ID NO:16.

6. The peptide of claim 1, which has the amino acid sequence of SEQ ID NO:20.

7. The peptide of claim 1, which has the amino acid sequence of SEQ ID NO:21.

8. The peptide of claim 1, which has the amino acid sequence of SEQ ID NO:22.

9. A composition, comprising a pharmaceutically acceptable carrier, excipient, diluent or auxiliary agent and at least one peptide of claim 1.

10. The composition of claim 9, further comprising a helper peptide.

11. The composition of claim 10, wherein said helper peptide contains a T helper epitope.

12. The composition of claim 9 which is a cell composition, wherein the pharmaceutically acceptable carrier is an antigen presenting cell which presents said at least one peptide.

13. The composition of claim 12, wherein said antigen presenting cell is selected from the group consisting of a dendritic cell, a macrophage, a B cell, and a fibroblast.

14. The composition of claim 13, wherein said antigen presenting cell is caused to present said at least one tumor associated antigen peptide by a method selected from the group consisting of:

(A) genetically modifying said antigen presenting cell with at least one polynucleotide encoding said at least one tumor associated antigen peptide such that said peptide or at least one polypeptide which comprises said peptide is expressed;

(B) loading said antigen presenting cell with at least one polynucleotide encoding said at least one tumor associated antigen peptide;

(C) loading said antigen presenting cell with said at least one tumor associated antigen peptide; and (D) loading said antigen presenting cell with at least one polypeptide comprising said at least one tumor associated antigen peptide.

15. An isolated polypeptide comprising the amino acid sequence of SEQ ID NO:61.

* * * * *

SEQUENCE LISTING

```
<160> NUMBER OF SEQ ID NOS: 61

<210> SEQ ID NO 1
<211> LENGTH: 26
<212> TYPE: DNA
<213> ORGANISM: Artificial Sequence
<220> FEATURE:
<223> OTHER INFORMATION: synthetic

<400> SEQUENCE: 1
ggaaactgtt gagaaacgg aactac                                         26

<210> SEQ ID NO 2
<211> LENGTH: 24
<212> TYPE: DNA
<213> ORGANISM: Artificial Sequence
<220> FEATURE:
<223> OTHER INFORMATION: synthetic

<400> SEQUENCE: 2
aatgccattg tagaaaagcg tgtg                                          24

<210> SEQ ID NO 3
<211> LENGTH: 32
<212> TYPE: DNA
<213> ORGANISM: Artificial Sequence
<220> FEATURE:
<223> OTHER INFORMATION: synthetic

<400> SEQUENCE: 3
```

```
ggtaagctta ccgccgctgg tcaccatgaa cc                                    32

<210> SEQ ID NO 4
<211> LENGTH: 37
<212> TYPE: DNA
<213> ORGANISM: Artificial Sequence
<220> FEATURE:
<223> OTHER INFORMATION: synthetic

<400> SEQUENCE: 4
agagctcgag gcctcaatga tgcctcctga tctatcg                               37

<210> SEQ ID NO 5
<211> LENGTH: 18
<212> TYPE: PRT
<213> ORGANISM: Artificial Sequence
<220> FEATURE:
<223> OTHER INFORMATION: synthetic

<400> SEQUENCE: 5

Tyr Leu Glu Glu Gln Lys Leu Ile Ser Glu Glu Asp Leu Gly Ser Ile
1               5                   10                  15

Asp Val

<210> SEQ ID NO 6
<211> LENGTH: 9
<212> TYPE: PRT
<213> ORGANISM: Homo sapiens

<400> SEQUENCE: 6

Val Leu Tyr Asp Glu Leu Lys Lys Val
1               5

<210> SEQ ID NO 7
<211> LENGTH: 9
<212> TYPE: PRT
<213> ORGANISM: Homo sapiens

<400> SEQUENCE: 7

Leu Leu Val Ile Ile Pro Val Leu Val
1               5

<210> SEQ ID NO 8
<211> LENGTH: 9
<212> TYPE: PRT
<213> ORGANISM: Homo sapiens

<400> SEQUENCE: 8

Val Gln Pro Gln Ser Pro Val Ala Val
1               5

<210> SEQ ID NO 9
<211> LENGTH: 9
<212> TYPE: PRT
<213> ORGANISM: Homo sapiens

<400> SEQUENCE: 9

Phe Glu Leu Ala Ala Glu Ser Asp Val
1               5

<210> SEQ ID NO 10
<211> LENGTH: 9
<212> TYPE: PRT
<213> ORGANISM: Homo sapiens
```

```
<400> SEQUENCE: 10

Gly Gln Gln Ser Thr Val Ser Asp Val
1               5

<210> SEQ ID NO 11
<211> LENGTH: 8
<212> TYPE: PRT
<213> ORGANISM: Homo sapiens

<400> SEQUENCE: 11

Glu Met Lys Glu Glu Gln Glu Val
1               5

<210> SEQ ID NO 12
<211> LENGTH: 9
<212> TYPE: PRT
<213> ORGANISM: Homo sapiens

<400> SEQUENCE: 12

Ile Gln Gln Tyr Gly His Gln Glu Val
1               5

<210> SEQ ID NO 13
<211> LENGTH: 9
<212> TYPE: PRT
<213> ORGANISM: Homo sapiens

<400> SEQUENCE: 13

Ala Leu Arg Gly His Ser His Phe Val
1               5

<210> SEQ ID NO 14
<211> LENGTH: 9
<212> TYPE: PRT
<213> ORGANISM: Homo sapiens

<400> SEQUENCE: 14

Val Ile Ala Thr Asn Ile Leu Leu Val
1               5

<210> SEQ ID NO 15
<211> LENGTH: 9
<212> TYPE: PRT
<213> ORGANISM: Homo sapiens

<400> SEQUENCE: 15

Thr Ile Leu Thr Ala Val Leu Leu Val
1               5

<210> SEQ ID NO 16
<211> LENGTH: 9
<212> TYPE: PRT
<213> ORGANISM: Homo sapiens

<400> SEQUENCE: 16

Ile Val Asp Asp Ile Thr Tyr Asn Val
1               5

<210> SEQ ID NO 17
<211> LENGTH: 9
<212> TYPE: PRT
<213> ORGANISM: Homo sapiens

<400> SEQUENCE: 17

Thr Leu Gln Leu Ser Arg Ala Pro Val
```

```
<210> SEQ ID NO 18
<211> LENGTH: 9
<212> TYPE: PRT
<213> ORGANISM: Homo sapiens

<400> SEQUENCE: 18

Ala Leu Pro Asp Glu Thr Glu Val Val
1               5

<210> SEQ ID NO 19
<211> LENGTH: 9
<212> TYPE: PRT
<213> ORGANISM: Homo sapiens

<400> SEQUENCE: 19

Ile Pro Met Gly Lys Ser Met Leu Val
1               5

<210> SEQ ID NO 20
<211> LENGTH: 9
<212> TYPE: PRT
<213> ORGANISM: Homo sapiens

<400> SEQUENCE: 20

Lys Ile Glu Asp Asn Asn Thr Leu Val
1               5

<210> SEQ ID NO 21
<211> LENGTH: 9
<212> TYPE: PRT
<213> ORGANISM: Homo sapiens

<400> SEQUENCE: 21

Met Leu Thr Ile Asn Gly Lys Ala Ile
1               5

<210> SEQ ID NO 22
<211> LENGTH: 9
<212> TYPE: PRT
<213> ORGANISM: Homo sapiens

<400> SEQUENCE: 22

Ser Ile Ala Glu Phe Phe Ser Asp Ile
1               5

<210> SEQ ID NO 23
<211> LENGTH: 9
<212> TYPE: PRT
<213> ORGANISM: Homo sapiens

<400> SEQUENCE: 23

Ala Leu Gly Phe Tyr Pro Ala Glu Ile
1               5

<210> SEQ ID NO 24
<211> LENGTH: 9
<212> TYPE: PRT
<213> ORGANISM: Homo sapiens

<400> SEQUENCE: 24

Trp Val Val Tyr Gly Val Phe Ser Ile
1               5
```

```
<210> SEQ ID NO 25
<211> LENGTH: 9
<212> TYPE: PRT
<213> ORGANISM: Homo sapiens

<400> SEQUENCE: 25

Leu Ile Leu Gly Ile Phe Met Thr Ile
1               5

<210> SEQ ID NO 26
<211> LENGTH: 9
<212> TYPE: PRT
<213> ORGANISM: Homo sapiens

<400> SEQUENCE: 26

Asp Leu Gln Glu Thr Leu Val Lys Ile
1               5

<210> SEQ ID NO 27
<211> LENGTH: 9
<212> TYPE: PRT
<213> ORGANISM: Homo sapiens

<400> SEQUENCE: 27

Lys Cys Leu Asn Ile Trp Ala Leu Ile
1               5

<210> SEQ ID NO 28
<211> LENGTH: 9
<212> TYPE: PRT
<213> ORGANISM: Homo sapiens

<400> SEQUENCE: 28

Thr Leu Asn Ala Trp Val Lys Val Val
1               5

<210> SEQ ID NO 29
<211> LENGTH: 9
<212> TYPE: PRT
<213> ORGANISM: Homo sapiens

<400> SEQUENCE: 29

Met Met Asn Asp Gln Leu Met Phe Leu
1               5

<210> SEQ ID NO 30
<211> LENGTH: 9
<212> TYPE: PRT
<213> ORGANISM: Homo sapiens

<400> SEQUENCE: 30

Ala Leu Phe Asp Ile Glu Ser Lys Val
1               5

<210> SEQ ID NO 31
<211> LENGTH: 9
<212> TYPE: PRT
<213> ORGANISM: Homo sapiens

<400> SEQUENCE: 31

Leu Leu His Glu Thr Asp Ser Ala Val
1               5

<210> SEQ ID NO 32
<211> LENGTH: 9
<212> TYPE: PRT
```

```
<213> ORGANISM: Homo sapiens

<400> SEQUENCE: 32

Val Leu Ala Gly Gly Phe Phe Leu Leu
1               5

<210> SEQ ID NO 33
<211> LENGTH: 9
<212> TYPE: PRT
<213> ORGANISM: Homo sapiens

<400> SEQUENCE: 33

Leu Val Leu Ala Gly Gly Phe Phe Leu
1               5

<210> SEQ ID NO 34
<211> LENGTH: 9
<212> TYPE: PRT
<213> ORGANISM: Homo sapiens

<400> SEQUENCE: 34

Phe Leu Thr Leu Ser Val Thr Trp Ile
1               5

<210> SEQ ID NO 35
<211> LENGTH: 9
<212> TYPE: PRT
<213> ORGANISM: Homo sapiens

<400> SEQUENCE: 35

Lys Leu Gln Cys Val Asp Leu His Val
1               5

<210> SEQ ID NO 36
<211> LENGTH: 9
<212> TYPE: PRT
<213> ORGANISM: Homo sapiens

<400> SEQUENCE: 36

Gly Val Leu Val His Pro Gln Trp Val
1               5

<210> SEQ ID NO 37
<211> LENGTH: 9
<212> TYPE: PRT
<213> ORGANISM: Homo sapiens

<400> SEQUENCE: 37

Val Leu Val His Pro Gln Trp Val Leu
1               5

<210> SEQ ID NO 38
<211> LENGTH: 9
<212> TYPE: PRT
<213> ORGANISM: Homo sapiens

<400> SEQUENCE: 38

Phe Met Leu Cys Ala Gly Arg Trp Thr
1               5

<210> SEQ ID NO 39
<211> LENGTH: 9
<212> TYPE: PRT
<213> ORGANISM: Homo sapiens

<400> SEQUENCE: 39
```

```
Gly Leu Leu Ser Phe Phe Phe Ala Val
1               5

<210> SEQ ID NO 40
<211> LENGTH: 9
<212> TYPE: PRT
<213> ORGANISM: Homo sapiens

<400> SEQUENCE: 40

Phe Leu Tyr Thr Leu Leu Arg Glu Val
1               5

<210> SEQ ID NO 41
<211> LENGTH: 9
<212> TYPE: PRT
<213> ORGANISM: Homo sapiens

<400> SEQUENCE: 41

Leu Leu Leu Gly Thr Ile His Ala Leu
1               5

<210> SEQ ID NO 42
<211> LENGTH: 9
<212> TYPE: PRT
<213> ORGANISM: Homo sapiens

<400> SEQUENCE: 42

Leu Ile Phe Lys Ser Ile Leu Phe Leu
1               5

<210> SEQ ID NO 43
<211> LENGTH: 9
<212> TYPE: PRT
<213> ORGANISM: Homo sapiens

<400> SEQUENCE: 43

Met Leu Thr Arg Lys Gln Phe Gly Leu
1               5

<210> SEQ ID NO 44
<211> LENGTH: 9
<212> TYPE: PRT
<213> ORGANISM: Homo sapiens

<400> SEQUENCE: 44

Phe Leu Phe Leu Leu Phe Phe Trp Leu
1               5

<210> SEQ ID NO 45
<211> LENGTH: 9
<212> TYPE: PRT
<213> ORGANISM: Homo sapiens

<400> SEQUENCE: 45

Val Leu Ala Lys Glu Leu Lys Phe Val
1               5

<210> SEQ ID NO 46
<211> LENGTH: 9
<212> TYPE: PRT
<213> ORGANISM: Homo sapiens

<400> SEQUENCE: 46

Ile Leu Leu Trp Gln Pro Ile Pro Val
1               5
```

<210> SEQ ID NO 47
<211> LENGTH: 9
<212> TYPE: PRT
<213> ORGANISM: Homo sapiens

<400> SEQUENCE: 47

Ser Leu Ser Leu Gly Phe Leu Phe Leu
1               5

<210> SEQ ID NO 48
<211> LENGTH: 9
<212> TYPE: PRT
<213> ORGANISM: Homo sapiens

<400> SEQUENCE: 48

Thr Leu Met Ser Ala Met Thr Asn Leu
1               5

<210> SEQ ID NO 49
<211> LENGTH: 9
<212> TYPE: PRT
<213> ORGANISM: Homo sapiens

<400> SEQUENCE: 49

Ile Leu Leu Val Met Gly Val Asp Val
1               5

<210> SEQ ID NO 50
<211> LENGTH: 9
<212> TYPE: PRT
<213> ORGANISM: Homo sapiens

<400> SEQUENCE: 50

Ser Leu Phe Phe Phe Pro Leu Pro Leu
1               5

<210> SEQ ID NO 51
<211> LENGTH: 9
<212> TYPE: PRT
<213> ORGANISM: Homo sapiens

<400> SEQUENCE: 51

Tyr Leu Phe Leu Cys Met Leu Ala Ala
1               5

<210> SEQ ID NO 52
<211> LENGTH: 9
<212> TYPE: PRT
<213> ORGANISM: Homo sapiens

<400> SEQUENCE: 52

Val Met Gly Val Asp Val Met Phe Ile
1               5

<210> SEQ ID NO 53
<211> LENGTH: 9
<212> TYPE: PRT
<213> ORGANISM: Homo sapiens

<400> SEQUENCE: 53

Val Met Gly Asp Ile Tyr Leu Leu Leu
1               5

<210> SEQ ID NO 54

```
<211> LENGTH: 9
<212> TYPE: PRT
<213> ORGANISM: Homo sapiens

<400> SEQUENCE: 54

Gly Leu Glu Lys Ala His Phe Trp Val
1               5

<210> SEQ ID NO 55
<211> LENGTH: 9
<212> TYPE: PRT
<213> ORGANISM: Homo sapiens

<400> SEQUENCE: 55

Val Leu Ala Met Phe Lys Ile Ser Cys
1               5

<210> SEQ ID NO 56
<211> LENGTH: 20
<212> TYPE: DNA
<213> ORGANISM: Homo sapiens

<400> SEQUENCE: 56
atgtcgtctg gtccctgttc                                                   20

<210> SEQ ID NO 57
<211> LENGTH: 20
<212> TYPE: DNA
<213> ORGANISM: Homo sapiens

<400> SEQUENCE: 57
gccattgtag aaaagcgtgt                                                   20

<210> SEQ ID NO 58
<211> LENGTH: 678
<212> TYPE: DNA
<213> ORGANISM: Homo sapiens
<220> FEATURE:
<221> NAME/KEY: CDS
<222> LOCATION: (31)..(429)

<400> SEQUENCE: 58
atcccggtaa cccgaccgcc gctggtcacc atg aac cac att gtg caa acc ttc      54
                                 Met Asn His Ile Val Gln Thr Phe
                                  1               5 tct cct gtc aac agc ggc cag cct ccc aac tac gag atg ctc aag gag      102
Ser Pro Val Asn Ser Gly Gln Pro Pro Asn Tyr Glu Met Leu Lys Glu
    10                  15                  20 gag cag gaa gtg gct atg ctg ggg gcg ccc cac aac cct gct ccc ccg      150
Glu Gln Glu Val Ala Met Leu Gly Ala Pro His Asn Pro Ala Pro Pro
25                  30                  35                  40 acg tcc acc gtg atc cac atc cgc agc gag acc tcc gtg cct gac cat      198
Thr Ser Thr Val Ile His Ile Arg Ser Glu Thr Ser Val Pro Asp His
                45                  50                  55 gtc gtc tgg tcc ctg ttc aac acc ctc ttc atg aac acc tgc tgc ctg      246
Val Val Trp Ser Leu Phe Asn Thr Leu Phe Met Asn Thr Cys Cys Leu
            60                  65                  70 ggc ttc ata gca ttc gcc tac tcc gtg aag tct agg gac agg aag atg      294
Gly Phe Ile Ala Phe Ala Tyr Ser Val Lys Ser Arg Asp Arg Lys Met
        75                  80                  85 gtt ggc gac gtg acc ggg gcc cag gcc tat gcc tcc acc gcc aag tgc      342
Val Gly Asp Val Thr Gly Ala Gln Ala Tyr Ala Ser Thr Ala Lys Cys
    90                  95                  100 ctg aac atc tgg gcc ctg att ttg ggc atc ttc atg acc att ctg ctc      390
```

```
Leu Asn Ile Trp Ala Leu Ile Leu Gly Ile Phe Met Thr Ile Leu Leu
            105                 110                 115                 120 gtc atc atc cca gtg ttg gtc gtc cag gcc cag cga tag atcaggaggc          439
Val Ile Ile Pro Val Leu Val Val Gln Ala Gln Arg
                125                 130 atcattgagg ccaggagctc tgcccgtgac ctgtatccca cgtactctat cttccattcc       499
tcgccctgcc cccagaggcc aggagctctg cccttgacct gtattccact tactccacct      559
tccattcctc gccctgtccc cacagccgag tcctgcatca gcccttatc ctcacacgct        619 tttctacaat ggcattcaat aaagtgtata tgtttctggt aaaaaaaaaa aaaaaaaa         678
```

<210> SEQ ID NO 59
<211> LENGTH: 132
<212> TYPE: PRT
<213> ORGANISM: Homo sapiens

<400> SEQUENCE: 59

```
Met Asn His Ile Val Gln Thr Phe Ser Pro Val Asn Ser Gly Gln Pro
1               5                   10                  15

Pro Asn Tyr Glu Met Leu Lys Glu Glu Gln Glu Val Ala Met Leu Gly
            20                  25                  30

Ala Pro His Asn Pro Ala Pro Pro Thr Ser Thr Val Ile His Ile Arg
        35                  40                  45

Ser Glu Thr Ser Val Pro Asp His Val Val Trp Ser Leu Phe Asn Thr
    50                  55                  60

Leu Phe Met Asn Thr Cys Cys Leu Gly Phe Ile Ala Phe Ala Tyr Ser
65                  70                  75                  80

Val Lys Ser Arg Asp Arg Lys Met Val Gly Asp Val Thr Gly Ala Gln
                85                  90                  95

Ala Tyr Ala Ser Thr Ala Lys Cys Leu Asn Ile Trp Ala Leu Ile Leu
            100                 105                 110

Gly Ile Phe Met Thr Ile Leu Leu Val Ile Ile Pro Val Leu Val Val
        115                 120                 125

Gln Ala Gln Arg
    130
```

<210> SEQ ID NO 60
<211> LENGTH: 396
<212> TYPE: DNA
<213> ORGANISM: Homo sapiens
<220> FEATURE:
<221> NAME/KEY: CDS
<222> LOCATION: (1)..(396)

<400> SEQUENCE: 60

```
atg aac cac att gtg caa acc ttc tct cct gtc aac agc ggc cag cct        48
Met Asn His Ile Val Gln Thr Phe Ser Pro Val Asn Ser Gly Gln Pro
1               5                   10                  15 ccc aac tac gag atg ctc aag gag gag cag gaa gtg gct atg ctg ggg        96
Pro Asn Tyr Glu Met Leu Lys Glu Glu Gln Glu Val Ala Met Leu Gly
            20                  25                  30 ggg ccc cac aac cct gct ccc ccg atg tcc acc gtg atc cac atc cgc       144
Gly Pro His Asn Pro Ala Pro Pro Met Ser Thr Val Ile His Ile Arg
        35                  40                  45 agc gag acc tcc gtg cct gac cat gtg gtc tgg tcc ctg ttc aac acc       192
Ser Glu Thr Ser Val Pro Asp His Val Val Trp Ser Leu Phe Asn Thr
    50                  55                  60 ctc ttc atg aac acc tgc tgc ctg ggc ttc ata gca ttc gcg tac tcc       240
Leu Phe Met Asn Thr Cys Cys Leu Gly Phe Ile Ala Phe Ala Tyr Ser
65                  70                  75                  80
```

-continued

```
gtg aag tct agg gac agg aag atg gtt ggc gac gtg acc ggg gcc cag      288
Val Lys Ser Arg Asp Arg Lys Met Val Gly Asp Val Thr Gly Ala Gln
            85                  90                  95 gcc tat gcc tcc acc gcc aag tgc ctg aac atc tgg gcc ctg att ttg      336
Ala Tyr Ala Ser Thr Ala Lys Cys Leu Asn Ile Trp Ala Leu Ile Leu
            100                 105                 110 ggc atc ttc atg acc att ctg ctc atc atc atc cca gtg ttg gtc gtc      384
Gly Ile Phe Met Thr Ile Leu Leu Ile Ile Ile Pro Val Leu Val Val
            115                 120                 125 cag gcc cag cga                                                       396
Gln Ala Gln Arg
    130

<210> SEQ ID NO 61
<211> LENGTH: 132
<212> TYPE: PRT
<213> ORGANISM: Homo sapiens

<400> SEQUENCE: 61

Met Asn His Ile Val Gln Thr Phe Ser Pro Val Asn Ser Gly Gln Pro
1               5                   10                  15

Pro Asn Tyr Glu Met Leu Lys Glu Glu Gln Glu Val Ala Met Leu Gly
            20                  25                  30

Gly Pro His Asn Pro Ala Pro Pro Met Ser Thr Val Ile His Ile Arg
        35                  40                  45

Ser Glu Thr Ser Val Pro Asp His Val Val Trp Ser Leu Phe Asn Thr
    50                  55                  60

Leu Phe Met Asn Thr Cys Cys Leu Gly Phe Ile Ala Phe Ala Tyr Ser
65                  70                  75                  80

Val Lys Ser Arg Asp Arg Lys Met Val Gly Asp Val Thr Gly Ala Gln
            85                  90                  95

Ala Tyr Ala Ser Thr Ala Lys Cys Leu Asn Ile Trp Ala Leu Ile Leu
            100                 105                 110

Gly Ile Phe Met Thr Ile Leu Leu Ile Ile Ile Pro Val Leu Val Val
            115                 120                 125

Gln Ala Gln Arg
    130
```